(12) United States Patent
Nitzel et al.

(10) Patent No.: US 10,206,993 B2
(45) Date of Patent: *Feb. 19, 2019

(54) PCV/MYCOPLASMA HYOPNEUMONIAE/LAWSONIA INTRACELLULARIS COMBINATION VACCINE

(71) Applicant: Zoetis Services LLC, Parsippany, NJ (US)

(72) Inventors: Gregory P. Nitzel, Paw Paw, MI (US); Jeffrey E. Galvin, Lincoln, NE (US); John Keith Garrett, North Wilkesboro, NC (US); James R. Kulawik, II, Lincoln, NE (US); Tracy L. Ricker, Portage, MI (US); Megan Marie Smutzer, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/480,973

(22) Filed: Apr. 6, 2017

(65) Prior Publication Data

US 2017/0216423 A1 Aug. 3, 2017

Related U.S. Application Data

(60) Continuation of application No. 14/712,426, filed on May 14, 2015, now Pat. No. 9,649,369, which is a (Continued)

(51) Int. Cl.
*A61K 39/12* (2006.01)
*C12N 7/00* (2006.01)
(Continued)

(52) U.S. Cl.
CPC .......... *A61K 39/12* (2013.01); *A61K 39/0241* (2013.01); *A61K 39/105* (2013.01);
(Continued)

(58) Field of Classification Search
None
See application file for complete search history.

(56) References Cited

U.S. PATENT DOCUMENTS 4,606,918 A 8/1986 Allison et al.
4,681,870 A 7/1987 Balint et al.
(Continued)

FOREIGN PATENT DOCUMENTS

EP 0283840 A2 3/1988
EP 0283085 A1 9/1988
(Continued)

OTHER PUBLICATIONS

Collins et al, "Isolation of Swine Infertility and Respiratory Syndrome Virus (Isolate ATCC VR-2332) in North America and Experimental Reproduction of the Disease in Gnotobiotic Pigs" Journal of Veterinary Diagnostic Investgation 1992, 4:117-126.
(Continued)

*Primary Examiner* — Shanon A. Foley
(74) *Attorney, Agent, or Firm* — Gloria K. Szakiel

(57) ABSTRACT

This invention provides a multivalent immunogenic composition including a soluble portion of a *Mycoplasma hyopneumoniae* (M.hyo) whole cell preparation; a porcine circovirus type 2 (PCV2) antigen; and a *Lawsonia intracellularis* antigen, wherein the soluble portion of the M.hyo preparation is substantially free of both (i) IgG and (ii) immunocomplexes comprised of antigen bound to immunoglobulin.

22 Claims, 10 Drawing Sheets

Specification includes a Sequence Listing.

Related U.S. Application Data division of application No. 13/850,329, filed on Mar. 26, 2013, now Pat. No. 9,125,885.

(60) Provisional application No. 61/620,175, filed on Apr. 4, 2012.

(51) Int. Cl.
*A61K 39/02* (2006.01)
*A61K 39/295* (2006.01)
*A61K 39/00* (2006.01)

(52) U.S. Cl.
CPC .............. *A61K 39/295* (2013.01); *C12N 7/00* (2013.01); *A61K 2039/521* (2013.01); *A61K 2039/5252* (2013.01); *A61K 2039/552* (2013.01); *A61K 2039/55566* (2013.01); *A61K 2039/70* (2013.01); *C12N 2750/10034* (2013.01)

(56) References Cited

U.S. PATENT DOCUMENTS

| | | | |
|---|---|---|---|
| 5,080,896 A | 1/1992 | Visser et al. | |
| 5,240,706 A | 8/1993 | Faulds et al. | |
| 5,252,328 A | 10/1993 | Faulds et al. | |
| 5,338,543 A | 8/1994 | Fitzgerald et al. | |
| 5,534,256 A | 7/1996 | Potter et al. | |
| 5,565,205 A | 10/1996 | Petersen et al. | |
| 5,620,691 A | 4/1997 | Wensvoort et al. | |
| 5,695,766 A | 12/1997 | Paul et al. | |
| 5,695,769 A | 12/1997 | Frantz et al. | |
| 5,788,962 A | 8/1998 | Wise et al. | |
| 5,846,735 A | 12/1998 | Stapleton et al. | |
| 6,110,467 A | 8/2000 | Paul et al. | |
| 6,113,916 A | 9/2000 | Bhogal et al. | |
| 6,162,435 A | 12/2000 | Minion et al. | |
| 6,193,971 B1 | 2/2001 | Hofmann et al. | |
| 6,251,397 B1 | 6/2001 | Paul et al. | |
| 6,251,404 B1 | 6/2001 | Paul et al. | |
| 6,268,199 B1 | 7/2001 | Meulenberg et al. | |
| 6,342,231 B1 | 1/2002 | Burkhardt et al. | |
| 6,380,376 B1 | 4/2002 | Paul et al. | |
| 6,500,662 B1 | 12/2002 | Calvert et al. | |
| 6,585,981 B1 | 7/2003 | Pijoan | |
| 6,592,873 B1 | 7/2003 | Paul et al. | |
| 6,753,417 B2 | 6/2004 | Hansen et al. | |
| 6,773,908 B1 | 8/2004 | Paul et al. | |
| 6,846,477 B2 | 1/2005 | Keich et al. | |
| 6,977,078 B2 | 12/2005 | Paul et al. | |
| 7,018,638 B2 | 3/2006 | Chu et al. | |
| 7,056,492 B2 | 6/2006 | Goudie et al. | |
| 7,074,894 B2 | 7/2006 | Walker et al. | |
| 7,169,394 B2 | 1/2007 | Chu et al. | |
| 7,223,854 B2 | 5/2007 | Paul et al. | |
| 7,264,802 B2 | 9/2007 | Paul et al. | |
| 7,264,957 B2 | 9/2007 | Paul et al. | |
| 7,279,166 B2 | 10/2007 | Minion et al. | |
| 7,419,806 B2 | 9/2008 | Minion et al. | |
| 7,517,976 B2 | 4/2009 | Paul et al. | |
| 7,575,752 B2 | 8/2009 | Meng et al. | |
| 7,622,124 B2 | 11/2009 | Chu et al. | |
| 7,959,927 B2 | 6/2011 | Chu et al. | |
| 8,008,001 B2 | 8/2011 | Roerink et al. | |
| 8,187,588 B2 | 5/2012 | Chu et al. | |
| 8,444,989 B1 | 5/2013 | Ohnesorge et al. | |
| 9,120,859 B2* | 9/2015 | Galvin | C07K 14/30 |
| 9,125,885 B2* | 9/2015 | Nitzel | A61K 39/295 |
| 9,125,886 B2* | 9/2015 | Nitzel | A61K 39/295 |
| 9,649,369 B2* | 5/2017 | Nitzel | A61K 39/295 |
| 9,650,600 B2* | 5/2017 | Galvin | C07K 14/30 |
| 9,650,601 B2* | 5/2017 | Nitzel | A61K 39/295 |
| 2002/0114817 A1 | 8/2002 | Liem et al. | |
| 2003/0092897 A1 | 5/2003 | Walker et al. | |
| 2005/0079185 A1 | 4/2005 | Parisot et al. | |
| 2006/0286123 A1 | 12/2006 | Fetzer et al. | |
| 2008/0279889 A1* | 11/2008 | Roof | A61K 39/12 424/204.1 |
| 2009/0092636 A1 | 4/2009 | Roof et al. | |
| 2009/0117152 A1 | 5/2009 | Chu et al. | |
| 2009/0317423 A1 | 12/2009 | Roof et al. | |
| 2012/0052514 A1 | 3/2012 | Allen et al. | |
| 2013/0183338 A1 | 7/2013 | Jacobs et al. | |
| 2013/0266602 A1 | 10/2013 | Nitzel et al. | |

FOREIGN PATENT DOCUMENTS

| | | |
|---|---|---|
| EP | 0315153 A2 | 5/1989 |
| EP | 0595436 A2 | 5/1994 |
| EP | 0325191 B1 | 9/1995 |
| EP | 2 275 132 A2 | 1/2011 |
| EP | 1 968 630 B1 | 1/2018 |
| GB | 2282811 | 4/1995 |
| WO | WO 1995/30437 | 11/1955 |
| WO | WO 1991/03157 | 3/1991 |
| WO | WO 1991/18627 | 12/1991 |
| WO | WO 1992/21375 | 12/1992 |
| WO | WO 1993/03760 | 3/1993 |
| WO | WO 1993/07898 | 4/1993 |
| WO | WO 1993/10216 | 5/1993 |
| WO | WO 1993/14196 | 7/1993 |
| WO | WO 1996/28472 A1 | 9/1996 |
| WO | WO 1996/40268 | 12/1996 |
| WO | WO 2002/10343 A2 | 2/2002 |
| WO | WO 2002/49666 A2 | 6/2002 |
| WO | WO 03003941 A2 | 1/2003 |
| WO | WO 2003/049703 A2 | 6/2003 |
| WO | WO 2004058142 A2 | 7/2004 |
| WO | WO 2007/116032 A1 | 10/2007 |
| WO | 2009/127684 A1 | 10/2009 |
| WO | WO 2009/126356 A2 | 10/2009 |
| WO | WO 2011/141443 A1 | 11/2011 |
| WO | 2012/025612 A1 | 3/2012 |
| WO | WO 2012/063212 A1 | 5/2012 |
| WO | 2013/152083 A2 | 10/2013 |
| WO | 2013/152086 A1 | 10/2013 |

OTHER PUBLICATIONS

Kwang, J. et al. "Cloning, Expression, and Sequence Analysis of the ORF4 Gene of the Porcine Reproductive and Respiratory Syndrome Virus MN-1b" Journal of Veterinary Diagnostic Investigation 1994, 6:293-296.

Mardassi, H. et al. "Molecular Analysis of the ORFs 3 to 7 of Porcine Reproductive and Respiratory Syndrome Virus, Quebec Reference Strain" Archives of Virology 1995, 140:1405-1418.

Meng, X.-J. et al. "Molecular Cloning and Nucleotide Sequencing of the 3'-Terminal Genomic RNA of the Porcine Reproductive and Respiratory Syndrome Virus" Journal of General Virology 1994, 75:1795-1801.

Wensvoort, G. et al. "Mystery Swine Disease in the Netherlands: the Isolation of Lelystad Virus" The Veterinary Quarterly 1991, 13:121-130.

Kim et al, "Identification and Mapping of an Immunogenic Region of Mycoplasma Hyopneumoniae p65 Surface Lipoprotein Expressed in *Escherichia coli* from a Cloned Genomic Fragment" Infection and Immunity 1990, 58:2637-2643.

Futo et al. "Molecular Cloning of a 46-Kiiodalton Surface Antigen (P46) Gene from Mycoplasma Hyopneumoniae: Direct Evidence of CGG Codon Usage for Arginine" Journal of Bacteriology 1995, 177:1915-1917.

Zhang et al. "Identification and Characterization of a Mycoplasma Hyopneumoniae Adhesin" Infection and Immunity 1995, 63: 1013-1029.

King et al. "Characterization of the Gene Encoding Mhp1 from Mycoplasma Hyopneumoniae and Examination of Mhp1's Vaccine Potential" Vaccine 1997, 15:25-35.

Okada et al. "Protective Effect of Vaccination with Culture Supernate of M.Hyopneumoniae Against Experimental Infection in Pigs" Journal of Veterinary Medicine 2000, 47:527-533.

(56) References Cited

OTHER PUBLICATIONS

Scarman et al. "Identification of Novel Species-Specific Antigens of Mycoplasma Hyopneumoniae by Preparative SDS-Page ELISA Profiling" Microbiology 1997, 143:663-673.

Strait et al. "Efficacy of a Mycoplasma Hyopneumoniae Bacterin in Pigs Challenged With Two Contemporary Pathogenic Isolates of M Hyopneumoniae" Journal of Swine Health and Production 2008, 16:200-206.

Alexander et al, "Adjuvants and their Modes of Action" Livestock Production Science 1995, 42:153-162.

Hunter et al. "The Adjuvant Activity of Nonionic Block Polymer Surfactants" The Journal of Immunologists 1981, 127:1244-1250.

Allison "Squalene and Squalane Emulsions as Adjuvants" Methods 1999, 19:87-93.

Goodwin et al. "Enzootic Pneumonia of Pigs: Immunization Attempts Inoculating Mycoplasma Suipneumoniae Antigen by Various Routes and with Different Adjuvants" British Veterinary Journal 1973. 129:456-464.

George et al. "Route-Related Variation in the Immunogenicity of Killed *Salmonella enteritidis* Vaccine: Role of Antigen Presenting Cells" Microbiol Immunol 1989, 33:479-488.

Byars et al. "Adjuvant Formulation for use in Vaccines to Elicit Both Cell-Mediated and Humoral Immunity" Vaccine 1987, 5:223-228.

Martinon et al. "Efficacy of a 'One Shot' Schedule of a Mycoplasma Hyopneumoniae Bacterin (Hyoresp)" Proceedings of the 15$^{th}$ IPVS Congress, Birmingham, England, Jul. 5-9, 1998, p. 284.

Reynaud et al. "Clinical Field Trial With Mycoplasma Hyopneumoniae Bacterin (Hyoresp)" Proceedings of the 15$^{th}$ IPVS Congress, Birmingham, England, Jul. 5-9, 1998 p. 150.

Charlier et al. "Comparative Efficacy of Stellamune Mycoplasma and Hyoresp in Pigs Against an Experimental Challenge with Mycoplasma Hyopneumoniae" The 16$^{th}$ International Pig Veterinary Society Congress, Melbourne, Australia Sep. 17-20, 2000, p. 501.

Djordjevic et al. "Serum and mucosal antibody responses and protection in pigs vaccinated against mycoplasma hyopneumoniae with vaccines containing a denatured membrane antigen pool and adjuvant", Australian Veterinary Journal, vol. 75 No. 7, pp. 504-511, Jul. 1, 1997.

Chen et al. "Evaluation of immune response to recombinant potential protective antigens of mycoplasma hyopneumoniae delivered as cocktail DNA and/or recombinant protein vaccines in mice". Vaccine, vol. 26 No. 34, pp. 4372-4378, Aug. 12, 2008.

Drexler et al. "Efficacy of combined porcine reproductive and respiratory syndrome virus and mycoplasma hyopneumoniae vaccination in piglets.", Veterinary Record, vol. 166 No. 3, pp. 70-74, Jan. 16, 2010.

Grau-Roma et al. "Recent advances in the epidemiology, diagnosis and control of diseases caused by porcine circovirus type 2", Veterinary Journal, vol. 187 No. 1 , Jan. 1, 2011.

Okada et al. "Cytological and immunological changes in bronchoalveolar lavage fluid and histological observation of lung lesions in pigs immunized with mycoplasma hyopneumoniae inactivated vaccine prepared from broth culture supernate", Vaccine, vol. 18, No. 25, pp. 2825-2831, Jun. 1, 2000.

Okada M.et al. "Evaluation of mycoplasma hyopneumoniate inactivated vaccine in pigs under field conditions", J. Vet. Med. Science, vol. 61 No. 10, pp. 1131-1135, Jun. 25, 1999.

Genzow Marika et al. "Concurrent vaccination of piglets with Ingelvac® PRRS MLV and with Ingelvac® M. hyo", Tieraerztliche Umschau, vol. 61 No. 12, pp. 649-652, Dec. 1, 2006.

Xin-Gang et al. "Baculovirus as a PRRSV and PCV2 bivalent vaccine vector: Baculovirus virions displaying simultaneously GP5 glycoprotein of PRRSV and capsid protein of PCV2", Journal of Virological Methods, vol. 179 No. 2, pp. 359-366, Nov. 28, 2011.

Ross "Characteristics of a protective activity of mycoplasma hyopneumoniae vaccine" American Journal of Veterinary Research, vol. 45 No. 10, pp. 1899-1905, Oct. 1984.

Sheldrake et al. "Evaluation of an enzyme-linked immunosorbent assay for the detection of Mycoplasma hyopneumoniae antibody in porcine serum" Australian Veterinary Journal vol. 69, No. 10, Oct. 1992.

Fort Dodge Australia (2000) TecnNote—Technical Update TF S04-00 (1) "Suvaxyn M. Hyo—How it works".

Zanh et al. (Journal of General Virology 2005: 86: 677-685).

Redgeld et al. (Nature Medicine 2002; 8 (7): 694-701).

Declaration of Gregory P. Nitzel from U.S. Appl. No. 13/850,318.

O'Dea, MA, Australia & New Zealand Standard Diagnostic Procedure, Jul. 2010 (http://www.agriculture.gov.au/SiteCollectionDocuments/animal/ahl/ANZSDP-Porcine-circovirus-infection.pdf), pp. 1-20.

Gillespie, J. et al., "Porcine Circovirus Type 2 and Porcine Circovirus-Associated Disease", J Vet Intern Med 2009; 23:1151-1163.

Allan, Gordon M. and Ellis, John A., "Porcine circoviruses: a review," J Vet Diagn Invest 12:3-14 (2000).

Freundt, E.A., "Culture Media for Classic Mycoplasmas," pp. 127-135 of Methods in Mycoplasmology, vol. I (Editors Razin and Tully).

Kricka, L.J., "Interferences in Immunoassay—Still a Threat", Clinical Chemistry 46, No. 8, 2000, pp. 1037-1038.

Selby, Colin, "Interference in immunoassay," Ann Clin Biochem 1999; 36: pp. 704-721.

Straw, B; Zimmerman, J.; D'Allaire, S.; Taylor, D. (eds), Diseases of Swine, (Wiley-Blackwell, 9th ed., 2006), Chapter 14.

APHIS info sheet (Jan. 2009), "PRRS Seroprevalence on U.S. Swine Operations," Veterinary Services; United States Department of Agriculture.

Bautista, Elida M. et al "Seroprevelence of PRRS virus in the United States," Swine Haan and Production—Nov. and Dec., 1993, 1: pp. 4-6.

Chen, Jia-Rong, et al., "Identification of the copper-zinc superoxide dismutase activity in Mycoplasma hyopneurrionae," Veterinary Microbiology 73 (2000) pp. 301-310.

Chen, Jia-Rong, et el., "Identification of a novel adhesin-like glycoprotein from Mycoplasma hyopneumoniae," Veterinary Microbiology 62 (1998) pp. 97-110.

Lam, K.M., "Serologic and immunologic studies on Mycopiesma hyopneumoniae pneumonia of swine," Iowa State University, Retrospective, Theses and Dissertations. 4178, 1970.

Border, Clement, "Phase Separation of Integral Membrane Proteins in Triton X-114 Solution", The Journal of Biological Chemistry, vol. 256, No. 4, Issue of Feb. 25 pp. 1604-1607,1981.

Porcine Respiratory Disease Complex—The Pig Site, Feb. 12, 2009, pp. 1-3. http://www.thepigsite.com/articles/2606/porcine-respiratory-disease.

Kaiser, Troy J. et al., "Mycoplasma Hyopneumoniae Efficacy and Field Safety Evaluation of a 3-Way Haemophilus Parasuis/Mycoplasma Hyopneumoniae Combination Bacterin," Allen D. Leman Swine Conference—Recent Research Reports, 31 (2008).

Quilitis, Michael Felipe E., "Serological response to PRRS vaccination using a mycoplasma bacterin (Mypravac® SUIS) as diluents for a live attenuated PRRSV vaccine Amervac®PRRS", Porcine Reproductive and Respiratory Syndrome (PRRS) Vaccination—Proceedings of the 21st IPVS Congress, Vancouver, Canada—Jul. 18-21, 2010. p. 235:541.

Hutchinson, Doug, "New Advancements in the Control of Erysipelas and Mycoplasma Pneumonia," M +Rhusigen™, Interview. (2005).

Responsible Use of Medicines in Agriculture Alliance (RUMA) Guidelines, "Responsible use of vaccines and vaccination in pig production," Nov. 2006, pp. 1-24.

\* cited by examiner

| Contrast | Mitigated Fraction | 95% confidence interval |
|---|---|---|
| T01 vs T02 | 41.2 | -5.9 to 76.5 |
| T01 vs T03 | 64.7 | 29.4 to 100 |
| T01 vs T04 | 76.5 | 41.2 to 100 |
| T01 vs T05 | 73.3 | 33.3 to 100 |
| T01 vs T06 | 62.5 | 25 to 100 |
| T01 vs T07 | 87.5 | 62.5 to 100 |
| T01 vs T08 | 88.2 | 64.7 to 100 |

Figure 10

| Preliminary Viricidal Activity | Difference from Water | | | |
| --- | --- | --- | --- | --- |
| | 100% rehyd. Lyophilized Titer | 90/10 Liq. (DMEM) 90/10 | 90/10 Liq. (Ultra) 90/10 | Avg Viricidal Activity |
| 20% SLCD | 0.8 | 0.7 | 2.0 | 1.3 |
| 0.2% Carbopol | 0.3 | -0.3 | 0.2 | -0.1 |
| 10% SP-Oil | 0.2 | 0.0 | 0.0 | 0.0 |
| 10% SP-Oil/0.2% Carbopol | 0.3 | -0.2 | 0.0 | -0.1 |
| 20% SLCD/10% SP-Oil | 1.0 | 0.3 | 0.7 | 0.5 |
| 20% SLCD/10% SP-Oil/0.2% Carbopol | 0.2 | 0.0 | 0.5 | 0.3 |
| 5% Amphigen (from 40% stock) | 1.0 | 0.7 | 1.5 | 1.1 |
| 2.5% Amphigen (from 40% stock) | NA | -0.2 | NA | -0.2 |
| 5% Amphigen (from 20% stock) | NA | 0.8 | NA | 0.8 |
| 2.5% Amphigen (from 20% stock) | NA | 0.2 | NA | 0.2 |
| 5% Amphigen (from 40% stock) | NA | 1.3 | NA | 1.3 |
| 2.5% Amphigen (from 40% stock) | NA | 0.8 | NA | 0.8 |
| | Indicates potential viricidal activity | | | |

SEQUENCE LISTING

<160> NUMBER OF SEQ ID NOS: 18

<210> SEQ ID NO 1
<211> LENGTH: 1260
<212> TYPE: DNA
<213> ORGANISM: Mycoplasma hyopneumoniae

<400> SEQUENCE: 1

```
atgaaaaaaa tgcttagaaa aaaattcttg tattcatcag ctatttatgc aacttcgctt      60
gcatcaatta ttgcatttgt tgcagcaggt tgtggacaga cagaatcagg ttcgacttct     120
gattctaaac cacaagccga gacgctaaaa cataaagtaa gtaatgattc tattcgaata     180
gcactaaccg atccggataa tcctcgatga attagtgctc aaaaagatat tatttcttat     240
gttgatgaaa cagaggcagc aacttcaaca attacaaaaa accaggatgc acagaataac     300
tgactcactc agcaagctaa tttaagccca gcaccaaaag gatttattat tgcccctgaa     360
aatggaagtg gagttggaac tgctgttaat acaattgctg ataaaggaat tccgattgtt     420
gcctatgatc gactaattac tggatctgat aaatatgatt ggtatgtttc ttttgataat     480
gaaaaagttg gcgaattaca aggtctttca cttgcagcgg gtctattagg aaaagaagat     540
ggtgcttttg attcaattga tcaaatgaat gaatatctaa aatcacatat gccccaagag     600
acaatttctt tttatacaat cgcgggttcc caagatgata taactcccca atatttttat     660
aatggtgcaa tgaaagtact aaagaatta atgaaaaatt cgggaaataa gataattgat     720
ttatctcctg aaggcgaaaa tgctgtttat gtcccaggat gaaattatgg aactgccggt     780
caaagaatcc aatctttcct aacaattaac aaagatccag caggtggtaa taaaatcaaa     840
gctgttggtt caaaaccagc ttctattttc aaaggatttc ttgccccaaa tgatggaatg     900
gccgarcaag caatcaccaa attaaaactt gaaggatttg atacccaaaa aatctttgta     960
actggtcaag attataatga taaagccaaa acttttatca aagacggcga tcaaaatatg    1020
acaatttata aacctgataa agttttagga aaagttgctg ttgaagttct tcgggtttta    1080
attgcaaaga aaaataaagc atccagatca gaagtcgaaa acgaactaaa agcaaaacta    1140
ccaaatattt catttaaata tgataatcaa acatataaag tgcaaggtaa aaatattaat    1200
acaattttag taagtccagt aattgttaca aaagctaatg ttgataatcc tgatgcctaa    1260
```

<210> SEQ ID NO 2
<211> LENGTH: 419
<212> TYPE: PRT
<213> ORGANISM: Mycoplasma hyopneumoniae

<400> SEQUENCE: 2

```
Met Lys Lys Met Leu Arg Lys Lys Phe Leu Tyr Ser Ser Ala Ile Tyr
1               5                   10                  15

Ala Thr Ser Leu Ala Ser Ile Ile Ala Phe Val Ala Ala Gly Cys Gly
            20                  25                  30

Gln Thr Glu Ser Gly Ser Thr Ser Asp Ser Lys Pro Gln Ala Glu Thr
        35                  40                  45

Leu Lys His Lys Val Ser Asn Asp Ser Ile Arg Ile Ala Leu Thr Asp
    50                  55                  60

Pro Asp Asn Pro Arg Trp Ile Ser Ala Gln Lys Asp Ile Ile Ser Tyr
65              70                  75                  80

Val Asp Glu Thr Glu Ala Ala Thr Ser Thr Ile Thr Lys Asn Gln Asp
            85                  90                  95

Ala Gln Asn Asn Trp Leu Thr Gln Gln Ala Asn Leu Ser Pro Ala Pro
            100                 105                 110

Lys Gly Phe Ile Ile Ala Pro Glu Asn Gly Ser Gly Val Gly Thr Ala
        115                 120                 125

Val Asn Thr Ile Ala Asp Lys Gly Ile Pro Ile Val Ala Tyr Asp Arg
    130                 135                 140

Leu Ile Thr Gly Ser Asp Lys Tyr Asp Trp Tyr Val Ser Phe Asp Asn
145                 150                 155                 160

Glu Lys Val Gly Glu Leu Gln Gly Leu Ser Leu Ala Ala Gly Leu Leu
                165                 170                 175

Gly Lys Glu Asp Gly Ala Phe Asp Ser Ile Asp Gln Met Asn Glu Tyr
            180                 185                 190

Leu Lys Ser His Met Pro Gln Glu Thr Ile Ser Phe Tyr Thr Ile Ala
        195                 200                 205

Gly Ser Gln Asp Asp Asn Asn Ser Gln Tyr Phe Tyr Asn Gly Ala Met
    210                 215                 220

Lys Val Leu Lys Glu Leu Met Lys Asn Ser Gly Asn Lys Ile Ile Asp
225                 230                 235                 240

Leu Ser Pro Glu Gly Glu Asn Ala Val Tyr Val Pro Gly Trp Asn Tyr
                245                 250                 255

Gly Thr Ala Gly Gln Arg Ile Gln Ser Phe Leu Thr Ile Asn Lys Asp
            260                 265                 270

Pro Ala Gly Gly Asn Lys Ile Lys Ala Val Gly Ser Lys Pro Ala Ser
        275                 280                 285

Ile Phe Lys Gly Phe Leu Ala Pro Asn Asp Gly Met Ala Glu Gln Ala
    290                 295                 300

Ile Thr Lys Leu Lys Leu Glu Gly Phe Asp Thr Gln Lys Ile Phe Val
305                 310                 315                 320

Thr Gly Gln Asp Tyr Asn Asp Lys Ala Lys Thr Phe Ile Lys Asp Gly
                325                 330                 335

Asp Gln Asn Met Thr Ile Tyr Lys Pro Asp Lys Val Leu Gly Lys Val
            340                 345                 350

Ala Val Glu Val Leu Arg Val Leu Ile Ala Lys Lys Asn Lys Ala Ser
        355                 360                 365

Arg Ser Glu Val Glu Asn Glu Leu Lys Ala Lys Leu Pro Asn Ile Ser
    370                 375                 380

Phe Lys Tyr Asp Asn Gln Thr Tyr Lys Val Gln Gly Lys Asn Ile Asn
385                 390                 395                 400

Thr Ile Leu Val Ser Pro Val Ile Val Thr Lys Ala Asn Val Asp Asn
```

Pro Asp Ala

<210> SEQ ID NO 3
<211> LENGTH: 3324
<212> TYPE: DNA
<213> ORGANISM: Mycoplasma hyopneumoniae

<400> SEQUENCE: 3
atgagtaaaa aatcaaaaac atttaaaatt ggtttgactg ccggaattgt tggtcttgga 60
gtttttggtc taactgtcgg acttagcagc ttggcaaaat acagatcaga aagtccacga 120
aagattgcaa atgattttgc cgcaaaagtt tcaacattag cttttagtcc ttatgctttt 180
gagactgatt ctgattataa aatagtcaaa aggtgactag ttgattctaa taacaatatt 240
agaaataaag aaaaagttat tgattccttt tccttttta ctaaaaacgg tgatcagtta 300
gaaaaaatta attttcaaga tcctgaatat accaaggcga agataacttt tgagattctt 360
gaaattatcc ctgatgatgt caatcaaaat tttaaggtaa aatttcaggc attacaaaaa 420
cttcataatg gtgatattgc caaatctgat atttatgagc aaacagttgc ttttgccaaa 480
cagtcaaatc ttttagttgc cgaatttaat ttttcgctta aaaaaattac cgaaaaatta 540
aatcaacaaa ttgaaaattt atcaacaaaa attacaaatt ttgctgatga aaaaacaagc 600
agccaaaaag atccctcaac tctaagagct attgacttcc aatacgattt aaatacagcg 660
cgaaatcctg aggatttaga tataaagctt gctaattatt ttccagtact taaaaattta 720
ataaacagac taaataatgc tcctgagaat aaattaccta ataatttggg taatattttt 780
gaatttagct ttgcaaaaga tagttcaact aatcaatatg taagtatcca gaaccaaatt 840
ccttcgctgt ttttaaaagc agatcttagt caaagtgccc gtgaaatttt agctagccca 900
gatgaagttc agccagttat taacattta agattaatga aaaaagataa ttcttcttat 960
tttctaaatt ttgaggattt tgttaataat ttaacactga aaaatatgca aaaagaagat 1020
ttaaatgcaa agggtcaaaa tctttctgcc tatgaatttc tagcagatat taaatctgga 1080
tttttccctg gagacaagag atccagtcat accaaggcag aaattagtaa tcttttaaat 1140
aaaaaagaaa atatttatga ctttggtaaa tacaatggaa aattcaacga ccgtcttaac 1200
tcgccaaatt tagaatatag cctagatgca gcaagcgcaa gtcttgataa aaaagataaa 1260
tcaatagttt taattcccta ccgccttgaa attaaagata aatttttgc cgatgattta 1320 tatccagata caaaagataa tattctcgta aaagaaggga ttcttaaatt aactggattt 1380
aaaaaaggct caaaaattga tctccctaat atcaatcagc aaatttttaa aaccgaatat 1440
ttaccatttt ttgaaaaagg taaagaagaa caagcaaaat tagactatgg taatatctta 1500
aatccatata atactcaact tgccaaagtt gaagttgaag ctcttttaa agggaataaa 1560 aaccaagaaa tctatcaagc acttgatgga aattatgcct atgaattcgg ggcctttaaa 1620
tccgtgctta attcctgaac aggaaaaatt cagcatcctg aaaaagctga tatccaaaga 1680
tttacaagac atttagaaca agttaaaatt ggttctaatt cagttttaaa tcaaccacaa 1740
acaacaaaag aacaagtaat ttcaagtctt aaaagtaata actttttaa aaatggacat 1800 caagttgcaa gttatttcca ggatttactc accaaggaca aattaacaat tttagagact 1860
ctttatgatc tagcaaaaaa atggggacta gaaactaaca gagcacaatt cccaaaaggg 1920
gttttccaat atacaaaaga tattttgca gaagcagata aattaaaatt tttggaattg 1980
aagaaaaagg atccttacaa tcagataaaa gaaattcacc aactttcctt taatatttta 2040

```
gcccgtaacg atgtaataaa atctgatgga ttttacggag ttttattatt gccccaaagt   2100
gtaaaaactg aattagaagg caaaaatgag gcgcaaattt ttgaagcgct taaaaagtat   2160
tctttaattg agaactcggc ttttaaaact actattttag ataaaaattt acttgaaggg   2220
actgatttta aaaccttcgg tgattttta aaagcatttt tccttaaagc agcccaattt   2280
aataattttg ctccttgagc aaaattagac gataatcttc agtattcatt tgaagctatc   2340
aaaaaagggg aaactacaaa agaaggtaaa agagaagaag tagataaaaa agttaaggaa   2400
ttggataata aaataaaagg tatattgcct cagcccccag cagcaaaacc agaagcagca   2460
aaaccagtag cggctaaacc agaaacaaca aaaccagtag cagctaaacc tgaagcagct   2520
aaacctgaag cagcaaaacc agtagcggct aaaccagaag cagcaaaacc agtagcggct   2580
aaaccagaag cagcaaaacc agtagcggct aaaccagaag cagcaaaacc agtagcggct   2640
aaaccagaag cagcaaaacc agttgctact aatactggct tttcacttac aaataaacca   2700
aaagaagact atttcccaat ggcttttagt tataaattag aatatactga cgaaaataaa   2760
ttaagcctaa aaacaccgga aattaatgta tttttagaac tagttcatca aagcgagtat   2820
gaagaacaag aaataataaa ggaactagat aaaactgttt taaatcttca atatcaattc   2880
caggaagtca aggtaactag tgaccaatat cagaaactta gccacccaat gatgaccgaa   2940
ggatcttcaa atcaaggtaa aaaaagcgaa ggaactccta accaaggtaa aaaagcagaa   3000
ggcgcgccta accaaggtaa aaaagccgaa ggaactccta accaagggaa aaaagcagag   3060
ggagcaccta gtcaacaaag cccaactacc gaattaacta attaccttcc tgacttaggt   3120
aaaaaaattg acgaaatcat taaaaaacaa ggtaaaaatt gaaaaacaga ggttgaacta   3180
atcgaggata atatcgctgg agatgctaaa ttgctatact ttatcctaag ggatgattca   3240
aaatccggtg atcctaaaaa atcaagtcta aaagttaaaa taacagtaaa acaaagtaat   3300
aataatcagg aaccagaatc taaa                                           3324
```

<210> SEQ ID NO 4
<211> LENGTH: 1108
<212> TYPE: PRT
<213> ORGANISM: Mycoplasma hyopneumoniae

<400> SEQUENCE: 4

```
Met Ser Lys Lys Ser Lys Thr Phe Lys Ile Gly Leu Thr Ala Gly Ile
1               5                   10                  15

Val Gly Leu Gly Val Phe Gly Leu Thr Val Gly Leu Ser Ser Leu Ala
            20                  25                  30

Lys Tyr Arg Ser Glu Ser Pro Arg Lys Ile Ala Asn Asp Phe Ala Ala
        35                  40                  45

Lys Val Ser Thr Leu Ala Phe Ser Pro Tyr Ala Phe Glu Thr Asp Ser
    50                  55                  60

Asp Tyr Lys Ile Val Lys Arg Trp Leu Val Asp Ser Asn Asn Asn Ile
65                  70                  75                  80

Arg Asn Lys Glu Lys Val Ile Asp Ser Phe Ser Phe Phe Thr Lys Asn
                85                  90                  95

Gly Asp Gln Leu Glu Lys Ile Asn Phe Gln Asp Pro Glu Tyr Thr Lys
            100                 105                 110

Ala Lys Ile Thr Phe Glu Ile Leu Glu Ile Ile Pro Asp Asp Val Asn
        115                 120                 125

Gln Asn Phe Lys Val Lys Phe Gln Ala Leu Gln Lys Leu His Asn Gly
    130                 135                 140
```

```
Asp Ile Ala Lys Ser Asp Ile Tyr Glu Gln Thr Val Ala Phe Ala Lys
145                 150                 155                 160

Gln Ser Asn Leu Leu Val Ala Glu Phe Asn Phe Ser Leu Lys Lys Ile
            165                 170                 175

Thr Glu Lys Leu Asn Gln Gln Ile Glu Asn Leu Ser Thr Lys Ile Thr
        180                 185                 190

Asn Phe Ala Asp Glu Lys Thr Ser Ser Gln Lys Asp Pro Ser Thr Leu
    195                 200                 205

Arg Ala Ile Asp Phe Gln Tyr Asp Leu Asn Thr Ala Arg Asn Pro Glu
210                 215                 220

Asp Leu Asp Ile Lys Leu Ala Asn Tyr Phe Pro Val Leu Lys Asn Leu
225                 230                 235                 240

Ile Asn Arg Leu Asn Asn Ala Pro Glu Asn Lys Leu Pro Asn Asn Leu
                245                 250                 255

Gly Asn Ile Phe Glu Phe Ser Phe Ala Lys Asp Ser Ser Thr Asn Gln
            260                 265                 270

Tyr Val Ser Ile Gln Asn Gln Ile Pro Ser Leu Phe Leu Lys Ala Asp
        275                 280                 285

Leu Ser Gln Ser Ala Arg Glu Ile Leu Ala Ser Pro Asp Glu Val Gln
    290                 295                 300

Pro Val Ile Asn Ile Leu Arg Leu Met Lys Lys Asp Asn Ser Ser Tyr
305                 310                 315                 320

Phe Leu Asn Phe Glu Asp Phe Val Asn Asn Leu Thr Leu Lys Asn Met
                325                 330                 335

Gln Lys Glu Asp Leu Asn Ala Lys Gly Gln Asn Leu Ser Ala Tyr Glu
            340                 345                 350

Phe Leu Ala Asp Ile Lys Ser Gly Phe Phe Pro Gly Asp Lys Arg Ser
        355                 360                 365

Ser His Thr Lys Ala Glu Ile Ser Asn Leu Leu Asn Lys Lys Glu Asn
    370                 375                 380

Ile Tyr Asp Phe Gly Lys Tyr Asn Gly Lys Phe Asn Asp Arg Leu Asn
385                 390                 395                 400

Ser Pro Asn Leu Glu Tyr Ser Leu Asp Ala Ala Ser Ala Ser Leu Asp
                405                 410                 415

Lys Lys Asp Lys Ser Ile Val Leu Ile Pro Tyr Arg Leu Glu Ile Lys
            420                 425                 430

Asp Lys Phe Phe Ala Asp Asp Leu Tyr Pro Asp Thr Lys Asp Asn Ile
        435                 440                 445

Leu Val Lys Glu Gly Ile Leu Lys Leu Thr Gly Phe Lys Lys Gly Ser
    450                 455                 460

Lys Ile Asp Leu Pro Asn Ile Asn Gln Gln Ile Phe Lys Thr Glu Tyr
465                 470                 475                 480

Leu Pro Phe Phe Glu Lys Gly Lys Glu Gln Ala Lys Leu Asp Tyr
                485                 490                 495

Gly Asn Ile Leu Asn Pro Tyr Asn Thr Gln Leu Ala Lys Val Glu Val
            500                 505                 510

Glu Ala Leu Phe Lys Gly Asn Lys Asn Gln Glu Ile Tyr Gln Ala Leu
        515                 520                 525

Asp Gly Asn Tyr Ala Tyr Glu Phe Gly Ala Phe Lys Ser Val Leu Asn
    530                 535                 540

Ser Trp Thr Gly Lys Ile Gln His Pro Glu Lys Ala Asp Ile Gln Arg
545                 550                 555                 560
```

```
Phe Thr Arg His Leu Glu Gln Val Lys Ile Gly Ser Asn Ser Val Leu
                565                 570                 575

Asn Gln Pro Gln Thr Thr Lys Glu Gln Val Ile Ser Ser Leu Lys Ser
            580                 585                 590

Asn Asn Phe Phe Lys Asn Gly His Gln Val Ala Ser Tyr Phe Gln Asp
        595                 600                 605

Leu Leu Thr Lys Asp Lys Leu Thr Ile Leu Glu Thr Leu Tyr Asp Leu
    610                 615                 620

Ala Lys Lys Trp Gly Leu Glu Thr Asn Arg Ala Gln Phe Pro Lys Gly
625                 630                 635                 640

Val Phe Gln Tyr Thr Lys Asp Ile Phe Ala Glu Ala Asp Lys Leu Lys
                645                 650                 655

Phe Leu Glu Leu Lys Lys Lys Asp Pro Tyr Asn Gln Ile Lys Glu Ile
            660                 665                 670

His Gln Leu Ser Phe Asn Ile Leu Ala Arg Asn Asp Val Ile Lys Ser
        675                 680                 685

Asp Gly Phe Tyr Gly Val Leu Leu Pro Gln Ser Val Lys Thr Glu
    690                 695                 700

Leu Glu Gly Lys Asn Glu Ala Gln Ile Phe Glu Ala Leu Lys Lys Tyr
705                 710                 715                 720

Ser Leu Ile Glu Asn Ser Ala Phe Lys Thr Thr Ile Leu Asp Lys Asn
                725                 730                 735

Leu Leu Glu Gly Thr Asp Phe Lys Thr Phe Gly Asp Phe Leu Lys Ala
            740                 745                 750

Phe Phe Leu Lys Ala Ala Gln Phe Asn Asn Phe Ala Pro Trp Ala Lys
        755                 760                 765

Leu Asp Asp Asn Leu Gln Tyr Ser Phe Glu Ala Ile Lys Lys Gly Glu
    770                 775                 780

Thr Thr Lys Glu Gly Lys Arg Glu Glu Val Asp Lys Lys Val Lys Glu
785                 790                 795                 800

Leu Asp Asn Lys Ile Lys Gly Ile Leu Pro Gln Pro Ala Ala Lys
                805                 810                 815

Pro Glu Ala Ala Lys Pro Val Ala Ala Lys Pro Glu Thr Thr Lys Pro
            820                 825                 830

Val Ala Ala Lys Pro Glu Ala Ala Lys Pro Glu Ala Ala Lys Pro Val
        835                 840                 845

Ala Ala Lys Pro Glu Ala Ala Lys Pro Val Ala Ala Lys Pro Glu Ala
    850                 855                 860

Ala Lys Pro Val Ala Ala Lys Pro Glu Ala Ala Lys Pro Val Ala Ala
865                 870                 875                 880

Lys Pro Glu Ala Ala Lys Pro Val Ala Thr Asn Thr Gly Phe Ser Leu
                885                 890                 895

Thr Asn Lys Pro Lys Glu Asp Tyr Phe Pro Met Ala Phe Ser Tyr Lys
            900                 905                 910

Leu Glu Tyr Thr Asp Glu Asn Lys Leu Ser Leu Lys Thr Pro Glu Ile
        915                 920                 925

Asn Val Phe Leu Glu Leu Val His Gln Ser Glu Tyr Glu Glu Gln Glu
    930                 935                 940

Ile Ile Lys Glu Leu Asp Lys Thr Val Leu Asn Leu Gln Tyr Gln Phe
945                 950                 955                 960

Gln Glu Val Lys Val Thr Ser Asp Gln Tyr Gln Lys Leu Ser His Pro
                965                 970                 975

Met Met Thr Glu Gly Ser Ser Asn Gln Gly Lys Lys Ser Glu Gly Thr
```

```
                980             985             990
Pro Asn Gln Gly Lys Lys Ala Glu Gly Ala Pro Asn Gln Gly Lys Lys
        995                 1000                1005

Ala Glu Gly Thr Pro Asn Gln Gly Lys Lys Ala Glu Gly Ala Pro
    1010                1015                1020

Ser Gln Gln Ser Pro Thr Thr Glu Leu Thr Asn Tyr Leu Pro Asp
    1025                1030                1035

Leu Gly Lys Lys Ile Asp Glu Ile Ile Lys Lys Gln Gly Lys Asn
    1040                1045                1050

Trp Lys Thr Glu Val Glu Leu Ile Glu Asp Asn Ile Ala Gly Asp
    1055                1060                1065

Ala Lys Leu Leu Tyr Phe Ile Leu Arg Asp Asp Ser Lys Ser Gly
    1070                1075                1080

Asp Pro Lys Lys Ser Ser Leu Lys Val Lys Ile Thr Val Lys Gln
    1085                1090                1095

Ser Asn Asn Asn Gln Glu Pro Glu Ser Lys
    1100                1105

<210> SEQ ID NO 5
<211> LENGTH: 1773
<212> TYPE: DNA
<213> ORGANISM: Porcine circovirus

<400> SEQUENCE: 5
```

| | | | |
|---|---|---|---|
| ggtacctccg tggattgttc tccagcagtc ttccaaaatt gcaaagtagt aatcctccga | 60 |
| tagagagctt ctacagctgg gacagcagtt gaggagtacc attcctgggg ggcctgattg | 120 |
| ctggtaatca aaatactgcg ggccaaaaaa ggaacagtac ccctttagt ctctacagtc | 180 |
| aatggatacc ggtcacacag tctcagtaga tcatcccaag gtaaccagcc ataaaaatca | 240 |
| tccaaaacaa caacttcttc tccatgatat ccatcccacc acttatttct actaggcttc | 300 |
| cagtaggtgt ccctaggctc agcaaaatta cgggcccact ggctcttccc acaaccgggc | 360 |
| gggcccacta tgacgtgtac agctgtcttc caatcacgct gctgcatctt cccgctcact | 420 |
| ttcaaaagtt cagccagccc gcggaaattt ctcacatacg ttacaggaaa ctgctcggct | 480 |
| acagtcacca agaccccgt ctccaaaagg gtactcacag cagtagacag gtcgctgcgc | 540 |
| ttcccctggt ccgcggagc tccacactcg ataagtatgt ggccttcttt actgcagtat | 600 |
| tctttattct gctggtcggt tcctttcgct ttctcgatgt ggcagcgggc accaaaatac | 660 |
| cacttcacct tgttaaaagt ctgcttctta gcaaaattcg caaaccctg gaggtgagga | 720 |
| gttctaccct cttccaaacc ttcctcgcca caaacaaaat aatcaaaaag ggagattgga | 780 |
| agctcccgta ttttgttttt ctcctcctcg aaggattat aagggtgaa cacccacctc | 840 |
| ttatggggtt gcgggccgct tttcttgctt ggcattttca ctgacgctgc cgaggtgctg | 900 |
| ccgctgccga gtgcgctgg taatactaca gcagcgcact tcttcactt ttataggatg | 960 |
| acgtatccaa ggaggcgtta ccgcagaaga agacaccgcc cccgcagcca tcttggccag | 1020 |
| atcctccgcc gccgccctg gctcgtccac cccgccacc gctaccgttg agaaggaaa | 1080 |
| aatggcatct tcaacacccg cctctcccgc accttcggat atactgtcaa ggctaccaca | 1140 |
| gtcagaacgc cctcctgggc ggtggacatg atgagattta atattgacga ctttgttccc | 1200 |
| ccgggagggg ggaccaacaa aatctctata cctttgaat actacagaat aagaaaggtt | 1260 |
| aaggttgaat tctggccctg ctcccccatc acccagggtg atagggggagt gggctccact | 1320 |
| gctgttattc tagatgataa ctttgtaaca aaggccacag ccctaaccta tgacccatat | 1380 |

```
gtaaactact cctcccgcca tacaatcccc caaccctcct cctaccactc ccgttacttc    1440
acacccaaac ctgttcttga ctccaccatt gattacttcc aaccaaataa caaaaggaat    1500
cagctttgga tgaggctaca aacctctaga aatgtggacc acgtaggcct cggcactgcg    1560
ttcgaaaaca gtatatacga ccaggactac aatatccgtg taaccatgta tgtacaattc    1620
agagaattta atcttaaaga ccccccactt aaaccctaaa tgaataaaaa taaaaaccat    1680
tacgatgtga taacaaaaaa gactcagtaa tttattttat atgggaaaag gcacagggt     1740 gggtccactg cttcaaatcg gccttcgggt acc                                 1773
```

<210> SEQ ID NO 6
<211> LENGTH: 702
<212> TYPE: DNA
<213> ORGANISM: Porcine circovirus

<400> SEQUENCE: 6

```
atgacgtatc caaggaggcg ttaccgcaga agaagacacc gcccccgcag ccatcttggc      60
cagatcctcc gccgccgccc ctggctcgtc caccccgcc accgctaccg ttggagaagg     120
aaaaatggca tcttcaacac ccgcctctcc cgcaccttcg gatatactgt caaggctacc    180
acagtcagaa cgccctcctg gcggtggac atgatgagat taatattga cgactttgtt     240 ccccgggag gggggaccaa caaaatctct atacccttg aatactacag aataagaaag     300
gttaaggttg aattctggcc ctgctccccc atcacccagg gtgatagggg agtgggctcc    360
actgctgtta ttctagatga taactttgta acaaaggcca cagccctaac ctatgaccca    420
tatgtaaact actcctcccg ccatacaatc ccccaacccct ctcctacca ctcccgttac    480 ttcacacccca aacctgttct tgactccacc attgattact ccaaccaaat aacaaaagg    540 aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
ttcagagaat taatcttaa agaccccccca cttaaaccct aa                       702
```

<210> SEQ ID NO 7
<211> LENGTH: 233
<212> TYPE: PRT
<213> ORGANISM: Porcine circovirus

<400> SEQUENCE: 7

```
Met Thr Tyr Pro Arg Arg Arg Tyr Arg Arg Arg His Arg Pro Arg
1               5                   10                  15

```
Phe Val Thr Lys Ala Thr Ala Leu Thr Tyr Asp Pro Tyr Val Asn Tyr
            130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
                195                 200                 205

Gln Asp Tyr Asn Ile Arg Val Thr Met Tyr Val Gln Phe Arg Glu Phe
210                 215                 220

Asn Leu Lys Asp Pro Pro Leu Lys Pro
225                 230

<210> SEQ ID NO 8
<211> LENGTH: 1767
<212> TYPE: DNA
<213> ORGANISM: Porcine circovirus

<400> SEQUENCE: 8
ggtacctccg tggattgttc tccagcagtc ttccaaaatt gcaaagtagt aatcctccga      60
tagagagctt ctacagctgg dacagcagtt gaggagtacc attcctgggg ggcctgattg     120
ctggtaatca aaatactgcg ggccaaaaaa ggaacagtac ccccttttagt ctctacagtc    180 aatggatacc ggtcacacag tctcagtaga tcatcccaag gtaaccagcc ataaaaatca    240
tccaaaacaa caacttcttc tccatgatat ccatcccacc acttattttct actaggcttc    300 cagtaggtgt cgctaggctc agcaaaatta cgggcccact ggctcttccc acaaccgggc    360
gggcccacta tgacgtgtac agctgtcttc caatcacgct gctgcatctt cccgctcact    420
ttcaaaagtt cagccagccc gcggaaattt ctcacatacg ttacagggaa ctgctcggct    480
acagtcacca agaccccgt ctccaaaagg gtactcacag cagtagacag gtcgctgcgc    540
ttcccctggt tccgcggagc tccacactcg ataagtatgt ggccttcttt actgcagtat    600
tctttattct gctggtcggt tccttttcgct ttctcgatgt ggcagcgggc accaaaatac    660
cacttcacct tgttaaaagt ctgcttctta gcaaaattcg caaaccctg gaggtgagga    720 gttctaccct cttccaaacc ttcctctccg caaacaaat aatcaaaaag ggagattgga    780
agctcccgta ttttgttttt ctcctcctcg gaaggattat aagggtgaa cacccacctc    840 ttatggggtt gcgggccgct tttcctgctt ggcatttttca ctgacgctgc cgaggtgctg    900
ccgctgccga agtgcgctgg taatactaca gcagcgcact tctttcactt ttataggatg    960
acgtatccaa ggaggcgtta ccgcagaaga agacaccgcc cccgcagcca tcttggccag   1020
atcctccgcc gccgccctg gctcgtccac cccgccacc gctaccgttg gagaaggaaa   1080
aatggcatct tcaacacccg cctctcccgc accttcggat atactgtcaa ggctaccaca   1140
gtcagaacgc cctcctggc ggtggacatg atgagattta atattgacga ctttgttccc   1200 ccggagggg ggaccaacaa atctctata ccctttgaat actacagaat aagaaaggtt   1260
aaggttgaat tctggccctg ctccccccatc acccagggtg ataggggagt gggctccact   1320
gctgttattc tagatgataa ctttgtaaca aaggccacag ccctaacccta tgacccatat   1380 gtaaactact cctcccgcca tacaatcgcc caacccttct cctaccactc ccgttacttc   1440
acacccaaac ctgttcttga ctccaccatt gattacttcc aaccaaataa caaaggaat   1500
```

```
cagctttgga tgaggctaca aacctctaga aatgtggacc acgtaggcct cggcactgcg    1560
ttcgaaaaca gtatatacga ccaggactac aatatccgtg taaccatgta tgtacaattc    1620
agagaattta atcttaaaga ccccccactt aaaccctaaa tgaataaaaa taaaaaccat    1680
tacgatgtga taacaaaaaa gactcagtaa tttattttat atgggaaaag gcacagggt     1740 gggtccactg cttcaaatcg gccttcg                                         1767

<210> SEQ ID NO 9
<211> LENGTH: 702
<212> TYPE: DNA
<213> ORGANISM: Porcine circovirus

<400> SEQUENCE: 9
atgacgtatc caaggaggcg ttaccgcaga agaagacacc gcccccgcag ccatcttggc      60
cagatcctcc gccgccgccc ctggctcgtc caccccccgcc accgctaccg ttggagaagg    120
aaaaatggca tcttcaacac ccgcctctcc cgcaccttcg gatatactgt caaggctacc    180
acagtcagaa cgccctcctg gcggtggac atgatgagat taatattga cgactttgtt      240 cccccgggag gggggaccaa caaaatctct atacccttgt aatactacag aataagaaag    300
gttaaggttg aattctggcc ctgctccccc atcccccagg gtgatagggg agtgggctcc    360
actgctgtta ttctagatga taactttgta acaaaggcca cagccctaac ctatgaccca    420
tatgtaaact actcctcccg ccatacaatc gcccaaccct ctcctacca ctcccgttac     480 ttcacaccca aacctgttct tgactccacc attgattact ccaaccaaa taacaaaagg     540 aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
ttcagagaat taatcttaa agacccccca cttaaaccct aa                        702

<210> SEQ ID NO 10
<211> LENGTH: 233
<212> TYPE: PRT
<213> ORGANISM: Porcine circovirus

<400> SEQUENCE: 10

Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Ala Gln Pro Phe Ser Tyr His Ser Arg Tyr
145                 150                 155                 160
```

```
Phe Thr Pro Lys Pro Val Leu Asp Ser Thr Ile Asp Tyr Phe Gln Pro
            165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
            195                 200                 205

Gln Asp Tyr Asn Ile Arg Val Thr Met Tyr Val Gln Phe Arg Glu Phe
            210                 215                 220

Asn Leu Lys Asp Pro Pro Leu Lys Pro
225                 230

<210> SEQ ID NO 11
<211> LENGTH: 233
<212> TYPE: PRT
<213> ORGANISM: Porcine circovirus

<400> SEQUENCE: 11

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
            50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
            130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
            165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
            195                 200                 205

Gln Asp Tyr Asn Ile Arg Val Thr Met Tyr Val Gln Phe Arg Glu Phe
            210                 215                 220

Asn Leu Lys Asp Pro Pro Leu Lys Pro
225                 230

<210> SEQ ID NO 12
<211> LENGTH: 713
<212> TYPE: DNA
<213> ORGANISM: Porcine circovirus

<400> SEQUENCE: 12
cagctatgac gtatccaagg aggcgttacc gcagaagaag acaccgcccc cgcagccatc    60
```

```
ttggccagat cctccgccgc cgcccctggc tcgtccaccc ccgccaccgc taccgttgga      120
gaaggaaaaa tggcatcttc aacacccgcc tctcccgcac cttcggatat actgtggaga      180
aggaaaaatg gcatcttcaa cacccgcctc tcccgcacct tcggatatac tgtgacgact      240 tgttccccc gggagggggg accaacaaaa tctctatacc ctttgaatac tacagaataa      300
gaaaggttaa ggttgaattc tggccctgct cccccatcac ccagggtgat aggggagtgg      360
gctccactgc tgttattcta gatgataact ttgtaacaaa ggccacagcc ctaacctatg      420
acccatatgt aaactactcc tcccgccata caatcccca accttctcc taccactccc      480 gttacttcac acccaaacct gttcttgact ccactattga ttacttccaa ccaaataaca      540
aaaggaatca gctttggctg aggctacaaa cctctagaaa tgtggaccac gtaggcctcg      600
gcactgcgtt cgaaaacagt aaatacgacc aggactacaa tatccgtgta accatgtatg      660
tacaattcag agaatttaat cttaaagacc ccccacttaa accctaaatg aat            713
```

<210> SEQ ID NO 13
<211> LENGTH: 233
<212> TYPE: PRT
<213> ORGANISM: Porcine circovirus

<400> SEQUENCE: 13

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
        50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230
```

<210> SEQ ID NO 14
<211> LENGTH: 713
<212> TYPE: DNA

<213> ORGANISM: Porcine circovirus

<400> SEQUENCE: 14

```
ccgccatgac gtatccaagg aggcgttacc gcagaagaag acaccgcccc cgcagccatc      60
ttggccagat cctcc 225          230

<210> SEQ ID NO 16
<211> LENGTH: 15450
<212> TYPE: DNA
<213> ORGANISM: Porcine reproductive and respiratory syndrome virus

<400> SEQUENCE: 16

| | | | | | |
|---|---|---|---|---|---|
| atgacgtata | ggtgttggct | ctatgccacg | gcatttgtat | tgtcaggagc | tgtggccatt | 60 |
| ggcacagccc | aaaacttgct | gcacggaaaa | cgcccttctg | tgacagcctt | cttcagggga | 120 |
| gcttaggggt | ctgtccctag | caccttgctt | ctggagttgc | actgctttac | ggtctctcca | 180 |
| cccctttaac | catgtctggg | atacttgatc | ggtgcacgtg | cacccccaat | gccagggtgt | 240 |
| ttatggcgga | gggccaagtc | tactgcacac | gatgtctcag | tgcacggtct | ctccttcctc | 300 |
| tgaatctcca | agttcctgag | cttggggtgc | tgggcctatt | ttataggccc | gaagagccac | 360 |
| tccggtggac | gttgccacgt | gcattcccca | ctgtcgagtg | ctcccctgcc | ggggcctgct | 420 |
| ggctttctgc | gatctttcca | attgcacgaa | tgaccagtgg | aaacctgaac | ttcaacaaa | 480 |
| gaatggtgcg | ggttgcagct | gagatttaca | gagccggcca | actcaccccc | tgcagttttga | 540 |
| aggctctaca | agtttatgaa | cggggttgtc | gctggtaccc | cattgtcgga | cctgtccctg | 600 |
| gagtggccgt | ttacgccaac | tccctacatg | tgagtgacaa | acctttcccg | ggagcaactc | 660 |
| atgtgttaac | caacctaccg | ctcccgcaga | ggcccaagcc | tgaagacttt | tgcccttttg | 720 |
| agtgtgctat | ggctaacgtc | tatgacattg | gccataacgc | cgtcatgtat | gtggccagag | 780 |
| ggaaagtctc | ctgggcccct | cgtggcgggg | atgaagtgaa | atttgaaacc | gtccccgaag | 840 |
| agttgaagtt | gattgcgaac | cgactccaca | tctccttccc | gccccaccac | gcagtggaca | 900 |
| tgtctgagtt | tgccttcata | gcccctggga | gtggtgtctc | cttgcgggtc | gagcaccaac | 960 |
| acggctgcct | tcccgctgat | actgtccctg | atgggaactg | ctggtggtac | ttgtttgact | 1020 |
| tgctccccacc | ggaagttcag | aataaagaaa | ttcgccgtgc | taaccaattt | ggctatcaaa | 1080 |
| ccaagcatgg | tgtccatggc | aagtacctac | agcggaggct | gcaagttaat | ggtctccgag | 1140 |
| cagtgactga | tacagatgga | cctattgtcg | tacagtactt | ctctgttagg | agagttgga | 1200 |
| tccgccactt | cagactggcg | gaagaaccta | gcctccctgg | gtttgaagac | tcctcagaa | 1260 |
| taagggtaga | gcctaatacg | tcgccaatgg | gtggcaaggg | tgaaaaaatc | ttccggtttg | 1320 |
| gcagtcacaa | gtggtacggt | gctggaaaga | gagcaaggag | agcacgctct | ggtgcgactg | 1380 |
| ccacggtcgc | tcaccgcgct | ttgcccgctc | gcgaagccca | gcaggccaag | aagctcgagg | 1440 |
| ttgccagcgc | caacagggct | gagcatctca | agtactattc | cccgcctgcc | gacgggaact | 1500 |
| gtggttggca | ctgcatttcc | gccattacca | accggatggt | gaattccaaa | tttgaaacca | 1560 |
| ctcttcccga | gagagtgaga | ccttcagatg | actgggctac | tgacgaggat | cttgtgaata | 1620 |
| ccatccaaat | cctcaggctc | cccgcggcct | tggacaggaa | cggtgcttgt | gctggcgcca | 1680 |
| agtacgtgct | caagctggaa | ggtgagcact | ggaccgtctc | tgtgaccccc | gggatgaccc | 1740 |
| cttctttgct | ccccccttgaa | tgtgttcagg | ttgttgtga | gcataagagc | ggtcttggtt | 1800 |
| tcccagacgt | ggtcgaagtt | tccggatttg | accctgcctg | tcttgaccga | cttgctgaga | 1860 |
| taatgcactt | gcctagcagt | gtcatcccag | ctgctctggc | cgagatgtcc | gacgacttca | 1920 |
| atcgtctggc | ttccccggcc | gccactgtgt | ggactgtttc | gcaattcttt | gcccgccaca | 1980 |
| gaggaggaga | gcatcctgac | caggtgtgct | tagggaaaat | tatcaacctt | tgtcaggtga | 2040 |
| ttgaggaatg | ctgctgttcc | cggaacaaag | ccaaccgggc | taccccggaa | gaggttgcgg | 2100 |

```
caaaagttga ccagtacctc cgtggtgcag caagccttgg agaatgcttg gccaagcttg    2160
agagggctcg cccgccgagc gcgacggaca cctcctttga ttggaatgtt gtgcttcctg    2220
gggttgagac ggcgaatcag acaaccaaac agctccatgt caaccagtgc cgcgctctgg    2280
ttcctgtcgt gactcaagag cctttggaca gagactcggt ccctctgacc gccttctcgc    2340
tgtccaattg ctactaccct gcacaaggtg acgaggtccg tcaccgtgag aggctaaact    2400
ccttgctctc taagttggag ggggttgttc gtgaggaata tgggctcacg ccaactggac    2460
ctggcccgcg acccgcactg ccgaacgggc tcgacgagct taaagaccag atggaggagg    2520
atctgctgaa attagtcaac gcccaggcaa cttcagaaat gatggcctgg gcagccgagc    2580
aggttgatct aaaagcttgg gtcaaaaatt acccacggtg acaccgcca cccctccac    2640 caagagttca gcctcgaaaa acgaagtctg tcaagagctt gctagagaac aagcctgtcc    2700
ctgctccgcg caggaaggtc agatctgatt gtggcagccc gattttgatg ggcgacaatg    2760
ttcctaacgg ttgggaagat tcgactgttg gtggtcccct tgatctttcg gcaccatccg    2820
agccgatgac acctctgagt gagcctgtac ttatttccag gccagtgaca tctttgagtg    2880
tgccggcccc agttcctgca ccgcgtagag ctgtgtcccg accgatgacg ccctcgagtg    2940
agccaatttt tgtgtctgca ctgcgacaca aatttcagca ggtggaaaaa gcaaatctgg    3000
cggcagcagc gccgatgtgc caggacgaac ccttagattt gtctgcatcc tcacagactg    3060
aatatgaggc ttccccccta acaccaccgc agaacgtggg cattctggag gtaaggggc     3120 aagaagctga ggaagttctg agtgaaatct cggatattct gaatgatacc aaccctgcac    3180
ctgtgtcatc aagcagctcc ctgtcaagtg ttaagatcac acgcccaaaa tactcagctc    3240
aagccattat cgactcgggc gggccctgca gtgggcacct ccaaagggaa aaagaagcat    3300
gcctccgcat catgcgtgaa gcttgtgatg cggccaagct tagtgaccct gccacgcagg    3360
aatggctttc tcgcatgtgg gatagggtgg acatgctgac ttggcgcaac acgtctgctt    3420
accaggcgtt tcgcaccta gatggcaggt ttgggtttct cccaaagatg atactcgaga    3480
cgccgccgcc ctaccgtgt gggttttgtga tgttgcctca caccctgca ccttccgtga     3540 gtgcagagag cgaccttacc attggttcag tcgccactga agatattcca cgcatcctcg    3600
ggaaaataga aaataccggt gagatgatca accagggacc cttggcatcc tctgaggaag    3660
aaccggtata caaccaacct gccaaagact cccggatatc gtcgcggggg tctgacgaga    3720
gcacagcagc tccgtccgcg ggtacaggtg gcgccggctt atttactgat ttgccacctt    3780
cagacggcgt agatgcggac ggtgggggc cgttgcagac ggtaagaaag aaagctgaaa    3840
ggctcttcga ccaattgagc cgtcaggttt taacctcgt ctcccatctc cctgttttct     3900
tctcacacct cttcaaatct gacagtggtt attctccggg tgattggggt tttgcagctt    3960
ttactctatt ttgcctcttt ttgtgttaca gctacccatt cttcggtttc gttcccctct    4020
tgggtgtatt ttctgggtct tctcggcgtg tgcgcatggg ggttttttggc tgctggctgg    4080 cttttgctgt tggcctgttc aagcctgtgt ccgacccagt cggcactgct tgtgagtttg    4140
actcgccaga gtgcaggaac gtccttcatt cttttgagct tctcaaacct tgggaccctg    4200
ttcgcagcct tgttgtgggc cccgtcgtc tcggtcttgc cattcttggc aagttactgg      4260
gcggggcacg ctacatctgg cattttttgc ttaggcttgg cattgttgca gattgtatct    4320
tggctggagc ttatgtgctt tctcaaggta ggtgtaaaaa gtgctgggga tcttgtataa    4380
gaactgctcc taatgaaatc gccttcaacg tgttcccttt tacacgtgcg accaggtcgt    4440
```

-continued

```
cactcatcga cctgtgcgat cggttttgtg cgccaacagg catggacccc attttcctcg    4500
ccactgggtg gcgtgggtgc tggaccggcc gaagtcccat tgagcaaccc tctgaaaaac    4560
ccatcgcgtt cgcccagttg gatgaaaaga ggattacggc tagaactgtg gtcgctcagc    4620
cttatgatcc taatcaagcc gtgaagtgct tgcgggtgtt acaggcgggt ggggcgatgg    4680
tggccgaggc agtcccaaaa gtggccaaag tttctgctat tccattccga gcccctttt     4740 ttcccaccgg agtgaaagtt gatcccgagt gcaggatcgt ggttacccc gatacttta     4800 ctacagccct ccggtctggt tactctacca caaacctcgt ccttggtgtg ggggactttg    4860
cccagctgaa tggactaaag atcaggcaaa tttccaagcc ttcggggagga ggcccacacc   4920 tcattgctgc cctgcatgtt gcctgctcga tggcgttgca catgcttgct ggggtttatg    4980
taacttcagt ggggtcttgc ggtgccggca ccaacgatcc atggtgcact aatccgtttg    5040
ccgttcctgg ctacggacca ggctctctct gcacgtccag attgtgcatc tcccaacatg    5100
gccttaccct gcccttgaca gcacttgtgg cgggattcgg tcttcaggaa atcgccttgg    5160
tcgttttgat tttcgtttcc atcggaggca tggctcatag gttgagttgt aaggctgata    5220
tgctgtgcat tttacttgca atcgccagct atgtttgggt accccttacc tggttgcttt    5280
gtgtgttccc ttgttggttg cgctggttct cttttgcaccc ccttaccatc ctatggttgg    5340
tgttttcttt gatttctgta aatatgcctt cgggaatctt ggccgtggtg ttattggttt     5400
ctctttggct tttgggacgt tatactaaca ttgctggtct tgtcaccccc tatgatattc    5460
atcattacac cagtggcccc cgcggtgttg ccgccttggc taccgcacca gatggaacct    5520
acttggctgc cgtccgccgc gctgcgttga ctggtcgcac catgctgttc accccgtctc    5580
agcttgggtc ccttcttgag ggcgctttca gaactcgaaa gccctcactg aacaccgtca    5640
atgtggttgg gtcctccatg ggctctggtg gagtgttcac catcgacggg aaaattaggt    5700
gcgtgactgc cgcacatgtc cttacgggta attcggctag ggtttccgga gtcggcttca    5760
atcaaatgct tgactttgat gtgaaagggg acttcgccat agctgattgc ccgaattggc    5820
aaggagctgc tcccaagacc caattctgcg aggacggatg gactggccgt gcctattggc    5880
tgacatcctc tggcgtcgaa cccgtgtta ttgggaatgg attcgccttc tgcttcaccg     5940
cgtgcggcga ttccgggtcc ccagtgatca ccgaagctgg tgagattgtc ggcgttcaca    6000
caggatcaaa taacaagga ggtggcatcg tcacgcgccc ttcaggccag ttttgtaacg     6060
tggcacccat caagctgagc gaattaagtg aattctttgc tggacccaag gtcccgctcg    6120
gtgatgtgaa ggttggcagc cacataatta agacacgtg cgaagtacct tcagatcttt     6180
gcgccttgct tgctgccaaa cctgaactgg agggaggcct ctccaccgtc aacttctgt     6240 gtgtgttttt cctactgtgg agaatgatgg acatgcctg gacgcccttg gttgctgtgg    6300
ggtttttcat tctgaatgag gttctcccag ctgtcctggt tcggagtgtt ttctccttg     6360 ggatgtttgt gctatcttgg ctcacaccat ggtctgcgca agttctgatg atcaggcttc    6420
taacagcagc tcttaacagg aacagatggt cacttgcctt ttacagcctt ggtgcggtga    6480
ccggttttgt cgcagatctt gcggtaactc aagggcaccc gttgcaggca gtaatgaatt    6540
tgagcaccta tgccttcctg cctcggatga tggttgtgac ctcaccagtc ccagtgattg    6600
cgtgtggtgt tgtgcaccta cttgccatca ttttgtactt gttcaagtac cgcggcctgc    6660
acaatgttct tgttggtgat ggagcgtttt ctgcagcttt cttcttgcga tactttgccg    6720
agggaaagtt gagggaaggg gtgtcgcaat cctgcggaat gaatcatgag tcattgactg    6780
gtgccctcgc tatgagactc aatgacgagg acttggactt ccttacgaaa tggactgatt    6840
```

```
ttaagtgctt tgtttctgcg tccaacatga ggaatgcagc aggccaattc atcgaggctg    6900
cctatgcaaa agcacttaga attgaacttg cccagttggt gcaggttgat aaggttcgag    6960
gtactttggc caagcttgag gcttttgctg ataccgtggc accccaactc tcgcccggtg    7020
acattgttgt tgctcttggc catacgcctg ttggcagcat cttcgaccta aaggttggtg    7080
gtaccaagca tactctccaa gtcattgaga ccagagtcct tgccgggtcc aaaatgaccg    7140
tggcgcgcgt cgttgaccca accccacgc ccccacccgc accgtgccc atccccctcc      7200 caccgaaagt tctagagaat ggtcccaacg cctgggggga tggggaccgt ttgaataaga    7260
agaagaggcg taggatggaa accgtcggca tctttgtcat gggtgggaag aagtaccaga    7320
aattttggga caagaattcc ggtgatgtgt ttacgagga ggtccatgac aacacagatg      7380
cgtgggagtg cctcagagtt ggtgaccctg ccgactttaa ccctgagaag ggaactctgt    7440
gtgggcatac tactattgaa gataaggatt acaaagtcta cgcctcccca tctggcaaga    7500
agttcctggt ccccgtcaac ccagagagcg gaagagccca tgggaagct gcaaagcttt      7560 ccgtggagca ggcccttggc atgatgaatg tcgacggtga actgacggcc aaagaagtgg    7620
agaaactgaa aagaataatt gacaaacttc agggccttac taaggagcag tgtttaaact    7680
gctagccgcc agcggcttga cccgctgtgg tcgcggcggc ttggttgtta ctgagacagc    7740
ggtaaaaata gtcaaatttc acaaccggac tttcaccta gggcctgtga atttaaaagt      7800
ggccagtgag gttgagctga agacgcggt cgagcacaac caacacccgg ttgcaagacc     7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact ttgaggccga ggccaccaaa gaggaaattg cgctcagtgc    8040
gcaaataata caggcttgtg acattaggcg cggtgacgca cctgaaattg gtctccctta    8100
caagctgtac cctgttaggg gcaacccga gcgggtaaaa ggagttttac agaatacaag    8160
gtttggagac ataccttaca aaaccccag tgacactggg agcccagtgc acgcggctgc    8220
ctgcctcacg cccaatgcca ctccggtgac tgatgggcgc tccgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccacgtggg taagtgcccg cccgttcatc ggccttccac    8520
ttaccctgcc aagaattcta tggctggaat aaatgggaac aggtttccaa ccaaggacat    8580
tcagagcgtc cccgaaatcg acgttctgtg cgcacaggcc gtgcgagaaa actggcaaac    8640 tgttaccct tgtaccctca agaaacagta ttgtgggaag aagaagacta ggacaatact     8700
cggcaccaat aatttcattg cgttggccca ccgggcagcg ttgagtggtg tcacccaggg    8760
cttcatgaaa aaggcgttta actcgcccat cgccctcggg aaaacaaat ttaaggagct     8820 acagactccg atcttaggca ggtgccttga agctgatctt gcatcctgtg atcgatccac    8880
acctgcaatt gtccgctggt ttgccgccaa ccttctttat gaacttgcct gtgctgaaga    8940
gcacctaccg tcgtacgtgc tgaactgctg ccatgaccta ttggtcacgc agtccggcgc    9000
agtgactaag aggggtggcc tgtcgtctgg cgacccgatc acttctgtgt ctaacaccat    9060
ttacagcttg gtgatatatg cacagcacat ggtgctagt tactttaaaa gtggtcaccc      9120
tcatggcctt ctgttcctac aagaccagct gaagttcgag gacatgctca aagtccaacc    9180
```

-continued

```
cctgatcgtc tattcggacg acctcgtgct gtatgccgaa tctcccacca tgccgaacta    9240
ccactggtgg gtcgaacatc tgaatttgat gctgggtttt cagacggacc caaagaagac    9300
agccataacg gactcgccat catttctagg ctgtaggata ataaatggac gccagctagt    9360
ccccaaccgt gacaggatcc tcgcggccct cgcttaccat atgaaggcaa acaatgtttc    9420
tgaatactac gccgcggcgg ctgcaatact catggacagc tgtgcttgtt tagagtatga    9480
tcctgaatgt tttgaagagc ttgtggttgg gatagcgcat tgcgcccgca aggacggcta    9540
cagctttccc ggcccgccgt tcttcttgtc catgtgggaa aaactcagat ccaatcatga    9600
ggggaagaag tccagaatgt gcgggtattg cggggccctg ctccgtacg ccactgcctg     9660 tggcctcgac gtctgtattt accacaccca cttccaccag cattgtccag tcacaatctg    9720
gtgtggccac ccggctggtt ctggttcttg tagtgagtgc aaaccccccc tagggaaagg    9780
cacaagccct ctagatgagg tgttagaaca agtcccgtat aagcctccac ggactgtaat    9840
catgcatgtg gagcagggtc tcacccctct tgacccaggc agataccaga ctcgccgcgg    9900
attagtctcc gttaggcgtg gcatcagagg aaatgaagtt gacctaccag acggtgatta    9960
tgctagcacc gccctactcc ccacttgtaa agagatcaac atggtcgctg tcgcctctaa   10020
tgtgttgcgc agcaggttca tcatcggtcc gcccggtgct gggaaaacat actggctcct   10080
tcagcaggtc caggatggtg atgtcattta cacccgact caccagacca tgctcgacat    10140
gattagggct ttggggacgt gccggttcaa cgtcccagca ggtgcaacgc tgcaattccc   10200 tgcccctcc cgtaccggcc cgtgggttcg catcctagcc ggcggttggt gtcctggtaa     10260
gaattccttc ttggatgaag cagcgtattg taatcacctt gatgtcttga ggctccttag   10320
caaaaccacc ctcacctgtc tgggagactt caaacaactc cacccagtgg ttttgattc    10380 tcattgctat gttttgaca tcatgcctca gacccgttg aagaccatct ggagattcgg     10440
acagaacatc tgtgatgcca tccaaccaga ttacagggac aaacttgtgt ccatggtcaa   10500 cacaaccgt gtaaccacg tggaaaaacc tgtcaagtat gggcaagtcc tcaccccta     10560 ccacagggac cgagaggacg gcgccatcac aattgactcc agtcaaggcg ccacatttga   10620
tgtggtcaca ctgcatttgc ccactaaaga ttcactcaac aggcaaagag cccttgttgc   10680
tatcaccagg gcaagacatg ctatctttgt gtatgaccca cacaggcaat gcagagcat    10740 gtttgatctt cctgcgaagg gcacacccgt caacctcgca gtgcaccgtg atgagcagct   10800
gatcgtactg gatagaaata taaagaatg cacagttgct caggctctag caacggaga    10860 taaatttagg gccaccgaca agcgcgttgt agattctctc cgcgccattt gtgctgatct   10920
ggaagggtcg agctctccgc tccccaaggt cgcacacaac ttgggatttt atttctcacc   10980
tgatttgaca cagtttgcta aactcccggt agaccttgca ccccactggc ccgtggtgac   11040
aacccagaac aatgaaaagt ggccggatcg gctggttgcc agccttcgcc ctgtccataa   11100
gtatagccgt gcgtgcattg gtgccggcta tatggtgggc cctcggtgt ttctaggcac    11160 ccctgggtc gtgtcatact acctcacaaa atttgtcaag gcgaggctc aagtgcttcc     11220 ggagacagtc ttcagcaccg gccgaattga ggtggattgc cgggagtatc ttgatgacag   11280
ggagcgagaa gttgctgagt ccctcccaca tgccttcatt ggcgacgtca aggcaccac    11340 cgttggggga tgtcatcatg tcacctccaa ataccttccg cgcttccttc caaggaatc    11400 agtcgcggta gtcgggggttt cgagccccgg gaaagccgca aaagcagtgt gcacattgac   11460
ggatgtgtac ctcccagacc ttgaggccta cctccaccca gagactcagt ccaagtgctg   11520
gaaagttatg ttggacttca aggaagttcg actgatggtc tggaaagaca agacggccta   11580
```

```
tttccaactt gaaggccgct atttcacctg gtatcagctt gcaagctacg cctcgtacat    11640
ccgtgttcct gtcaactcca cggtgtatct ggacccctgc atgggccctg ccctttgcaa    11700
cagaagagtt gtcgggtcca cccattgggg agctgacctc gcagtcaccc cttatgatta    11760
cggtgctaaa atcatcttgt ctagcgctta ccatggtgaa atgcctcctg gatacaagat    11820
tctggcgtgc gcggagttct cgctcgacga cccagtcaag tacaaacaca cctggggttt    11880
tgaatcggat acagcgtatc tgtatgagtt caccggaaac ggtgaggact gggaggatta    11940
caatgatgcg tttcgtgcgc gccagaaagg gaaaatttat aaggccactg ctaccagcat    12000
gaagttttat tttcccccgg gccccgtcat tgaaccaact ttaggcctga attgaaatga    12060
aatggggtct atacaaagcc tcttcgacaa aattggccag cttttttgtgg atgctttcac    12120
ggaattttg gtgtccattg ttgatatcat catattttg gccatttgt ttggcttcac       12180
catcgccggt tggctggtgg tcttttgcat cagattggtt tgctccgcgg tattccgtgc    12240
gcgccctgcc attcaccctg agcaattaca gaagatccta tgaggccttt ctttctcagt    12300
gccgggtgga cattcccacc tgggggtaa acacccttt ggggatgttt tggcaccata     12360
aggtgtcaac cctgattgat gaaatggtgt cgcgtcgaat gtaccgcgtc atggataaag    12420
cagggcaagc tgcctggaaa caggtggtga gcgaggctac gctgtctcgc attagtagtc    12480
tggatgtggt ggctcatttt caacatcttg ccgccattga agccgagacc tgtaaatatt    12540
tggcttctcg actgcccatg ctacacaacc tgcgcatgac agggtcaaat gtaaccatag    12600
tgtataatag cactttaaat caggtgtttg ctattttttcc aacccctggt tcccggccaa    12660
agcttcatga ttttcagcaa tggctaatag ctgtacattc ctccatattt tcctctgttg    12720
cagcttcttg tactcttttt gttgtgctgt ggttgcgggt tccaatgcta cgtactgttt    12780
ttggtttccg ctggttaggg gcaattttttc tttcgaactc atggtgaatt acacggtgtg    12840
tccaccttgc ctcacccgac aagcagccgc tgaggtcctt gaacccggta ggtctctttg    12900
gtgcaggata gggcatgacc gatgtgggga ggacgatcac gacgaactgg ggttcatggt    12960
tccgcctggc ctctccagcg aaagccactt gaccagtgtt tacgcctggt tggcgttcct    13020
gtccttcagc tacacggccc agttccatcc cgagatattt gggataggga acgtgagtga    13080
agtttatgtt gacatcaagc accaattcat ctgcgccgtt catgacgggc agaacaccac    13140
cttgcctcgc catgacaata tttcagccgt atttcagacc tactatcaac atcaggtcga    13200
cggcggcaat tggtttcacc tagaatggct gcgtcccttc tttttcctctt ggttggtttt    13260
aaatgtttcg tggtttctca ggcgttcgcc tgcaagccat gtttcagttc gagtctttca    13320
gacatcaaaa ccaacactac cgcagcatca ggctttgttg tcctccagga catcagctgc    13380
cttaggcatg gcgactcgtc ctttccgacg attcgcaaaa gctctcaatg ccgcacggcg    13440
ataggacac ctgtgtatat caccatcaca gccaatgtga cagatgagaa ttacttacat     13500
tcttctgatc tcctcatgct ttcttcttgc cttttctatg cttctgagat gagtgaaaag    13560
ggattcaagg tggtatttgg caatgtgtca ggcatcgtgg ctgtgtgtgt caactttacc    13620
agctacgtcc aacatgtcaa agagtttact caacgctcct tggtggtcga tcatgtgcgg    13680
ctgcttcatt tcatgacacc tgagaccatg aggtgggcaa ccgttttagc ctgtctttttt    13740
gccatcctac tggcaatttg aatgttcaag tatgttgggg aaatgcttga ccgcgggctg    13800
ttgctcgcga ttgcttttctt tgtggtgtat cgtgccgttc tggtttgctg tgctcggcaa    13860
cgccaacagc agcagcagct ctcatttcca gttgatttat aacttgacgc tatgtgagct    13920
```

```
gaatggcaca gattggctgg cagaaaaatt tgattgggcg gtggagactt ttgtcatctt    13980
tcccgtgttg actcacattg tttcctattg tgcactcacc accagccatt tccttgacac    14040
agttggtctg gttactgtgt ccaccgccgg gttttatcac gggcggtatg tcttgagtag    14100
catctacgcg gtctgtgctc tggctgcgtt gatttgcttc gttattaggc ttgcgaagaa    14160
ctgcatgtcc tggcgctact cttgtaccag atataccaac ttccttctgg acactaaggg    14220
cagactctat cgttggcggt cgcccgttat catagaaaaa aggggtaagg ttgaggtcga    14280
aggtcatctg atcgacctca aaagagttgt gcttgatggt tccgtggcaa ccccctttaac   14340 cagagtttca gcggaacaat ggggtcgtct ctagacgact tttgccatga tagcactgct    14400
ccacaaaagg tgcttttggc gttttccatt acctacacgc cagtaatgat atatgctcta    14460
aaggtaagtc gcggccgact gctagggctt ctgcaccttt tgatcttttct gaattgtgct   14520 tttaccttcg ggtacatgac attcgcgcac tttcagagca caaatagggt cgcgctcgct    14580
atgggagcag tagttgcact tctttgggg gtgtactcag cctatagaaac ctggaaattc    14640 atcacctcca gatgccgttt tgtgcttgcta ggccgcaagt acattctggc ccctgcccac   14700
cacgtcgaaa gtgccgcggg ctttcatccg attgcggcaa atgataacca cgcatttgtc    14760
gtccggcgtc ccggctccat tacgcttaac ggcacattgg tgcccgggtt gaaaagcctc    14820
gtgttgggtg gcagaaaagc tgttaaacag ggagtggtaa accttgtcaa atatgccaaa    14880
taacaacggc aagcagcaaa agaaaaagaa ggggaatggc cagccagtca accagctgtg    14940
ccagatgctg ggtaaaatca tcgcccagca aaaccagtcc agaggcaagg gaccgggcaa    15000
gaaaagtaag aagaaaaacc cggagaagcc ccatttccct ctagcgaccg aagatgacgt    15060
caggcatcac ttcacccctg gtgagcggca attgtgtctg tcgtcgatcc agactgcctt    15120
taaccagggc gctggaactt gtaccctgtc agattcaggg aggataagtt acactgtgga    15180
gtttagtttg ccgacgcatc atactgtgcg cctgatccgc gtcacagcat caccctcagc    15240
atgatgggct ggcattcttt aggcacctca gtgtcagaat tggaagaatg tgtggtggat    15300
ggcactgatt gacattgtgc ctctaagtca cctattcaat tagggcgacc gtgtgggggt    15360
aaaatttaat tggcgagaac catgcggccg caattaaaaa aaaaaaaaaa aaaaaaaaa    15420 aaaaaaaaaa aaaaaaaaaa aaaaaaaaa                                      15450
```

<210> SEQ ID NO 17
<211> LENGTH: 2352
<212> TYPE: DNA
<213> ORGANISM: Porcine reproductive and respiratory syndrome virus

<400> SEQUENCE: 17

```
cctatcattg aaccaacttt aggcctgaat tgaaatgaaa tggggtctat gcaaagcctt      60
tttgacaaaa ttggccaact tttcgtggat gctttcacgg agttcttggt gtccattgtt     120
gatatcatta tatttttggc catttttgttt ggcttcacca tcgccggttg gctggtggtc     180
ttttgcatca gattggtttg ctccgcgata ctccgtgcgc ccctgccat tcactctgag      240 caattacaga agatcctatg aggcctttct ttctcagtgc caggtggaca ttcccacctg     300
gggaattaaa catcccttgg ggatgctttg caccataag gtgtcaaccc tgattgatga     360
aatggtgtcg cgtcgaatgt accgcatcat ggaaaaagca ggacaggctg cctggaaaca     420
ggtggtgagc gaggctacgc tgtctcgcat tagtagtttg gatgtggtgg ctcactttca     480
gcatcttgcc gccattgaag ccgagacctg taaatatttg gcctctcggc tgcccatgct     540
acacaacctg cgcatgacag ggtcaaatgt aaccatagtg tataatagta ctttgaatca     600
```

```
ggtgcttgct attttcccaa cccctggttc ccggccaaag cttcatgatt ttcagcaatg      660
gctaatagct gtacattcct ctatattttc ctctgttgca gcttcttgta ctcttttttgt     720 tgtgctgtgg ttgcgggttc caatgctacg tattgctttt ggtttccgct ggttaggggc      780
aattttcttt tcgaactcac agtgaactac acggtgtgtc caccttgcct cacccggcaa      840
gcagccacag aggcctacga acctggcagg tctctttggt gcaggatagg gtatgatcgc      900 tgtgggagg acgatcatga tgaactaggg tttgtggtgc cgtctggcct ctccagcgaa       960
ggccacttga ccagtgttta cgcctggttg gcgttcctgt ctttcagtta cacagcccag     1020
ttccatcctg agatattcgg gatagggaat gtgagtcaag tttatgttga catcaggcat     1080
caattcattt gcgccgttca cgacgggcag aacgccactt gcctcgcca tgacaatatt      1140 tcagccgtgt tccagactta ttaccaacat caagtcgacg gcggcaattg gtttcaccta    1200
gaatggctgc gtcccttctt ttcctcttgg ttggttttaa atgtctcttg gtttctcagg    1260
cgttcgcctg caagccatgt ttcagttcga gtcttgcaga cattaagacc aacaccaccg    1320
cagcggcagg ctttgctgtc ctccaagaca tcagttgcct taggtatcgc aactcggcct    1380
ctgaggcgtt tcgcaaaatc cctcagtgtc gtacggcgat agggacaccc atgtatatta    1440
ctgtcacagc caatgtaacc gatgagaatt atttgcattc ctctgacctt ctcatgcttt    1500
cttcttgcct tttctacgct tctgagatga gtgaaaaggg atttaaagtg gtatttggca    1560
atgtgtcagg catcgtggct gtgtgcgtca actttaccag ctacgtccaa catgtcaagg    1620
aatttaccca cgctccttg gtagtcgacc atgtgcggct gctccatttc atgacacctg     1680
agaccatgag gtgggcaact gttttagcct gtctttttgc cattctgttg gccatttgaa    1740
tgtttaagta tgttggggaa atgcttgacc gcgggctatt gctcgtcatt gcttttttttg   1800 tggtgtatcg tgccgtcttg gtttgttgcg ctcgccagcg ccaacagcag caacagctct    1860
catttacagt tgatttataa cttgacgcta tgtgagctga atggcacaga ttggttagct    1920
ggtgaatttg actgggcagt ggagtgtttt gtcattttc ctgtgttgac tcacattgtc     1980
tcctatggtg ccctcaccac cagccatttc cttgacacag tcggtctggt cactgtgtct    2040
accgccggct tttcccacgg gcggtatgtt ctgagtagca tctacgcggt ctgtgccctg    2100
gctgcgttga tttgcttcgt cattaggttt acgaagaatt gcatgtcctg gcgctactca    2160
tgtaccagat ataccaactt tcttctggac actaagggca gactctatcg ttggcggtcg    2220
cctgtcatca tagagaaaag gggtaaagtt gaggtcgaag gtcatctgat cgacctcaag    2280
agagttgtgc ttgatggttc cgcggcaacc cctataacca agtttcagc ggagcaatgg     2340 ggtcgtcctt ag                                                        2352
```

<210> SEQ ID NO 18
<211> LENGTH: 886
<212> TYPE: DNA
<213> ORGANISM: Porcine reproductive and respiratory syndrome virus

<400> SEQUENCE: 18

```
atggggtcgt ccttagatga cttctgccat gatagcacgg ctccacaaaa ggtgcttttg      60
gcgttctcta ttacctacac gccagtgatg atatatgccc taaaagtaag tcgcggccga    120
ctgctagggc ttctgcacct tttgatcttc ctaaattgtg ctttcacctt cgggtacatg    180
acattcgtgc actttcagag cacaaacaag gtcgcgctca ctatgggagc agtagttgca    240
ctcctttggg gggtgtactc agccatagaa acctggaaat tcatcacctc cagatgccgt    300
```

-continued

```
ttgtgcttgc taggccgcaa gtacattttg gcccctgccc accacgttga aagtgccgca    360
ggctttcatc cgatagcggc aaatgataac cacgcatttg tcgtccggcg tcccggctcc    420
actacggtta acggcacatt ggtgcccggg ttgaaaagcc tcgtgttggg tggcagaaaa    480
gctgtcaaac agggagtggt aaaccttgtt aaatatgcca aataacaacg gcaagcagca    540
gaagaaaaag aaggggatg gccagccagt caatcagctg tgccagatgc tgggtaagat     600
catcgctcag caaaccagt ccagaggcaa gggaccggga aagaaaaaca agaagaaaaa     660
cccggagaag ccccattttc ctctagcgac tgaagatgat gtcagacatc acttcacctc    720
tggtgagcgg caattgtgtc tgtcgtcaat ccagacagcc tttaatcaag gcgctggaac    780
ttgtaccctg tcagattcag ggaggataag ttacactgtg gagtttagtt tgccgacgca    840
tcatactgtg cgcctgatcc gcgtcacagc gtcaccctca gcatga                   886
```

PCV/MYCOPLASMA HYOPNEUMONIAE/LAWSONIA INTRACELLULARIS COMBINATION VACCINE

CROSS-REFERENCE TO RELATED APPLICATIONS

This application is a continuation of U.S. application Ser. No. 14/712,426, filed May 14, 2015 (now U.S. Pat. No. 9,649,369), which is a divisional of U.S. application Ser. No. 13/850,329, filed Mar. 26, 2013, now U.S. Pat. No. 9,125,885, which claims the benefit of U.S. Provisional Application No. 61/620,175, filed Apr. 4, 2012, the contents each of which are incorporated herein by reference in their entirety.

FIELD OF THE INVENTION

The present invention relates to porcine circovirus, *Mycoplasma hyopneumoniae* (*M. hyopneumoniae* or M.hyo), and other microorganisms that can cause disease in pigs. More particularly, the invention relates to a multivalent immunogenic composition including a soluble portion of an M.hyo whole cell preparation, a PCV2 antigen, and a *Lawsonia intracellularis* antigen and its use in a vaccine for protecting pigs against enzootic pneumonia, Post-weaning Multisystemic Wasting Syndrome (PMWS), and disease caused by *Lawsonia intracellularis*.

BACKGROUND OF THE INVENTION

Enzootic pneumonia in swine, also called mycoplasmal pneumonia, is caused by M.hyo. The disease is a chronic, non-fatal disease affecting pigs of all ages. Infected pigs show only mild symptoms of coughs and fever, but the disease has significant economic impact due to reduced feed efficiency and reduced weight gain. Enzootic pneumonia is transmitted from pig to pig through the nasal passages by airborne organisms expelled from the lungs of infected pigs. The primary infection by M.hyo may be followed by secondary infection by other *mycoplasma* species (*Mycoplasma hyorhinis* and *Mycoplasma flocculare*) as well as other bacterial pathogens.

M.hyo is a small, prokaryotic microbe capable of a free living existence, although it is often found in association with eukaryotic cells because it has absolute requirements for exogenous sterols and fatty acids. These requirements generally necessitate growth in serum-containing media. M.hyo is bounded by a cell membrane, but not a cell wall.

The physical association of mycoplasmas with the host cell surface is the basis for the development and persistence of enzootic pneumonia. M.hyo infects the respiratory tract of swine, colonizing the trachea, bronchi, and bronchioles. The *mycoplasma* produces a ciliostatic factor which causes the cilia lining the respiratory passages to stop beating. Eventually, the cilia degenerate, leaving the pig prone to infection by secondary pathogens. Characteristic lesions of purple to gray areas of consolidation are observed in infected animals. Surveys of slaughtered animals revealed lesions in 30 to 80% of swine. Results from 37 herds in 13 states indicated that 99% of the herds had hogs with pneumonia lesions typical of enzootic pneumonia. Therefore, the need for effective preventative and treatment measures are great.

Antibiotics such as tiamulin, trimethoprim, tetracyclines and lincomycin have some benefit, but are expensive and require prolonged use. Additionally, antibiotics have not been shown to effectively eliminate spread or reinfection of M.hyo. Prevention by maintaining pathogen-free herds is sometimes possible but reintroduction of M.hyo often occurs. Due to the serious economic consequences of swine pneumonia, vaccines against M.hyo have been sought. Vaccines containing preparations of mycoplasmal organisms grown in serum-containing medium have been marketed, but raise concerns regarding adverse reactions induced by serum components (such as immunocomplexes or non-immunogenic specific proteins) present in the immunizing material. Other attempts to provide M. hyo vaccines have been successful, but the disease remains widespread.

M.hyo and porcine circovirus type 2 (PCV2) are the two most prevalent pathogens that are encountered in the pig industry. Swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia. M.hyo is associated with enzootic pneumonia and has also been implicated as one of the major co-factors in the development of Porcine Circovirus Associated Disease (PC-VAD).

Porcine reproductive and respiratory syndrome (PRRS) is caused by an arterivirus, which has a particular affinity for the macrophages particularly those found in the lung (alveolar macrophages). These macrophages ingest and remove invading bacteria and viruses, but not in the case of the PRRS virus (PRRSV). In the case of the PRRS virus, it multiplies inside the macrophages producing more virus and kills the macrophages. Once PRRSV has entered a herd, it tends to remain present and active indefinitely. Up to 40% of the macrophages are destroyed, which allows bacteria and other viruses to proliferate and do damage. A common example of this is the noticeable increase in severity of enzootic pneumonia in grower/finisher units when they become infected with PRRS virus. More than half of weaning-age PRRS virus-negative pigs become infected before going to market.

What is needed is a PCV2/M.hyo combination vaccine against both PCV2 and *mycoplasma* infection in swine. Preferably, this multivalent vaccine will be compatible with other porcine antigens, such as PRRS virus antigen. It would be highly desirable to provide a ready-to-use in one bottle, single-dose PCV2/M.hyo combination vaccine.

SUMMARY OF THE INVENTION

The present invention provides a multivalent immunogenic composition comprising a soluble portion of a *Mycoplasma hyopneumoniae* (M.hyo) whole cell preparation; a porcine circovirus type 2 (PCV2) antigen; and a *Lawsonia intracellularis* antigen, wherein the soluble portion of the M.hyo preparation comprises M.hyo-specific soluble protein antigens and is separated from insoluble cellular material and substantially free of both (i) IgG and (ii) immunocomplexes comprised of antigen bound to immunoglobulin. In one aspect, the soluble portion of the M.hyo whole cell preparation has been treated with protein-A or protein-G prior to being added to the immunogenic composition.

In another embodiment, the soluble portion of the M.hyo preparation includes two or more M.hyo protein antigens, as well as heterologous proteins from the M.hyo culture fluid.

In some embodiments, the immunogenic composition of the present invention further includes at least one additional antigen that is protective against a microorganism that can cause disease in pigs.

In one embodiment, the microorganism includes bacteria, viruses, or protozoans. In another embodiment, the microorganism is selected from, but is not limited to, the following: porcine reproductive and respiratory syndrome virus (PRRSV), porcine parvovirus (PPV), *Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplasma hyorhinis, Mycoplasma hyosynoviae,* leptospira bacteria, swine influenza virus (SIV), *Escherichia coli* antigen, *Brachyspira hyodysenteriae,* porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) and a pathogen causative of Swine Transmissable Gastroenteritis, or combinations thereof.

In one embodiment, the composition elicits a protective immune response in a pig against M.hyo, PCV2, and *Lawsonia intracellularis.*

In one embodiment, the PCV2 antigen is in the form of a chimeric type-1-type 2 circovirus, the chimeric virus including an inactivated recombinant porcine circovirus type 1 expressing the porcine circovirus type 2 ORF2 protein. In another embodiment, the PCV2 antigen is in the form of a recombinant ORF2 protein. In still another embodiment, the recombinant ORF2 protein is expressed from a baculovirus vector.

In some embodiments, the composition of the present invention further includes an adjuvant. In one embodiment, the adjuvant is selected from, but is not limited to, the following: an oil-in-water adjuvant, a polymer and water adjuvant, a water-in-oil adjuvant, an aluminum hydroxide adjuvant, a vitamin E adjuvant and combinations thereof. In another embodiment, the composition of the present invention further includes a pharmaceutically acceptable carrier.

In one embodiment, the composition elicits a protective immune response against M.hyo, PCV2, and *Lawsonia intracellularis* when administered as a single dose administration.

The present invention also provides a method of immunizing a pig against M.hyo, PCV2, and *Lawsonia intracellularis.* This method includes administering to the pig an immunogenic composition including a PCV2 antigen, a *Lawsonia intracellularis* antigen, and a soluble portion of an M.hyo whole cell preparation, wherein the soluble portion of the M.hyo preparation comprises M.hyo-specific soluble protein antigens and is separated from insoluble cellular material and substantially free of both (i) IgG and (ii) immunocomplexes comprised of antigen bound to immunoglobulin. In one embodiment, the soluble portion of the M.hyo preparation of the administered composition includes two or more M.hyo protein antigens, as well as heterologous proteins from the M.hyo culture fluid.

In one embodiment of the method of the present invention, the composition is administered intramuscularly, intradermally, transdermally, or subcutaneously. In another embodiment of the method of this invention, the composition is administered in a single dose or in multiple doses. In one specific embodiment of the method of this invention, the composition is administered as two doses.

In a further embodiment of the method of the present invention, the composition is administered in conjunction with at least one additional antigen that is protective against a microorganism that can cause disease in pigs, such as one or more of the microorganisms described above. Such other antigens can be given concurrently with the M.hyo composition (i.e., as separate single vaccines) or combined in a ready-to-use vaccine.

In a further embodiment, the composition is administered to pigs having maternally derived antibodies against at least one of M.hyo and PCV2.

In one embodiment, the composition is administered to pigs at 3 weeks of age or older.

The present invention further provides a kit. This kit includes a bottle comprising an immunogenic composition. This immunogenic composition includes the soluble portion of a *Mycoplasma hyopneumoniae* (M.hyo) whole cell preparation, a PCV2 antigen, and a *Lawsonia intracellularis* antigen, wherein the soluble portion of the M.hyo preparation comprises M.hyo-specific soluble protein antigens and is separated from insoluble cellular material and substantially free of both (i) IgG and (ii) antigen/immunoglobulin immunocomplexes. In one embodiment, the kit further includes an instruction manual containing information to administer the immunogenic composition.

Additionally, the present invention provides a method for preparing an immunogenic composition according to this invention. This method includes i) culturing M.hyo in a suitable media over periods ranging from 18-144 hours; ii) subsequently inactivating the M. hyo culture; iii) harvesting the inactivated culture fluid, wherein the inactivated culture fluid comprises an M.hyo whole cell preparation comprising both a soluble liquid fraction and insoluble cellular material; iv) separating the soluble liquid fraction from the insoluble cellular material; v) substantially removing both IgG and antigen/immunoglobulin immunocomplexes from the separated soluble liquid fraction to form a soluble portion of the M.hyo whole cell preparation; and vi) subsequently combining the soluble portion of the M.hyo whole cell preparation with a PCV2 antigen and a *Lawsonia intracellularis* antigen.

BRIEF DESCRIPTION OF THE DRAWINGS

FIG. 10 is a table showing the adjuvant evaluation for virucidal activity against PRRS virus.

BRIEF DESCRIPTION OF THE SEQUENCES

Figure 1:
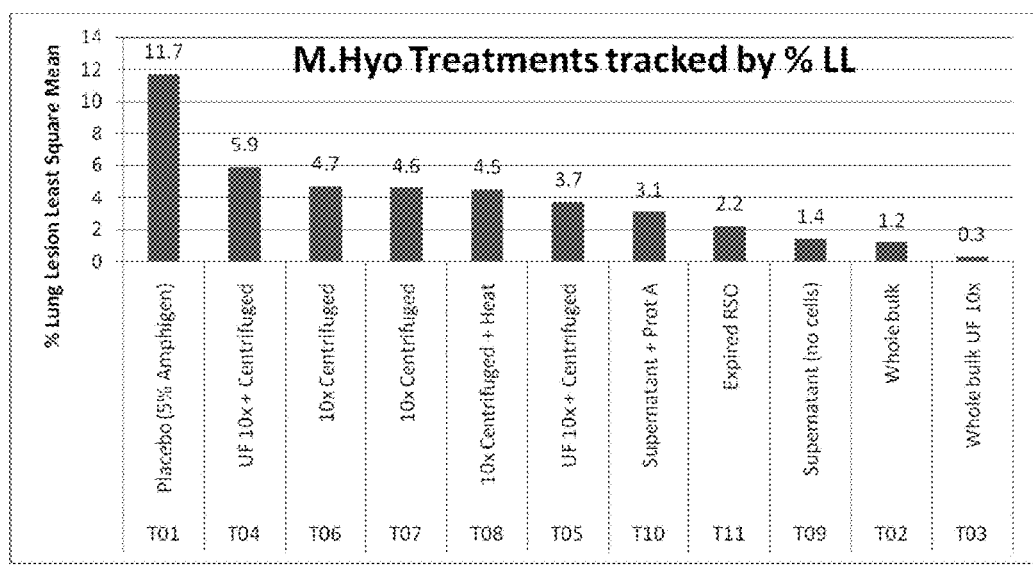
FIG. 1 is a graph showing the efficacy of M.hyo monovalent vaccines prepared with M.hyo antigens from different treatments (T02-T10 described in Example 3) vs. a placebo (T01). The results are presented as % Lung Lesion Least Square Mean values.
Figure 2:
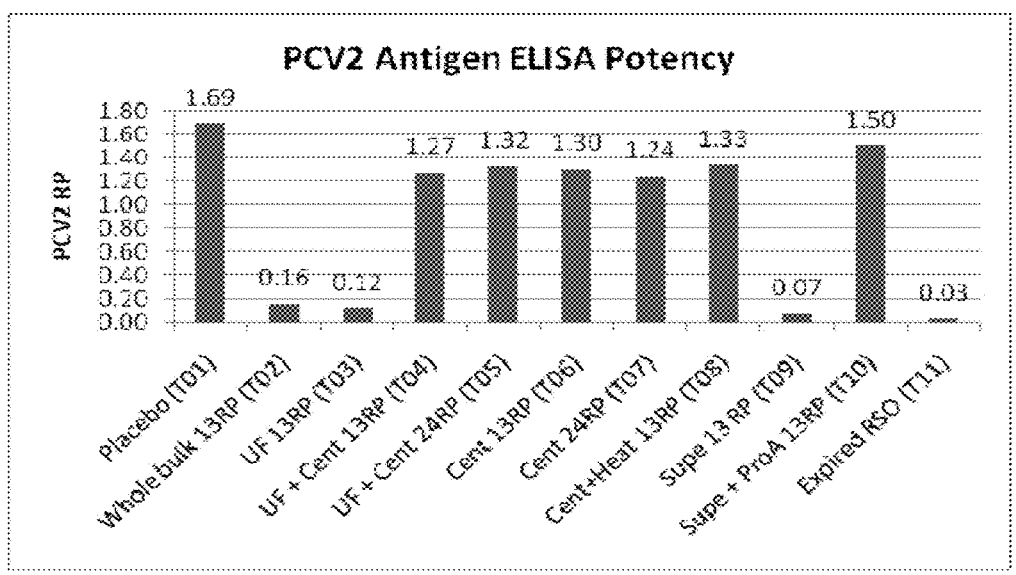
FIG. 2 is a graph showing the PCV2 antigen potency results (PCV2 antigen ELISA) of M.hyo vaccines in combination with killed PCV Type1-Type2 chimeric virus. The chimeric virus was included in the compositions at an initial level of about 1.6≤RP. The status of each sample is expressed as relative potency (RP).

SEQ ID NO: 1 is one embodiment of a nucleotide sequence encoding p46 from the P-5722 strain of M.hyo;

SEQ ID NO: 2 is one embodiment of an amino acid sequence corresponding to p46 from the P-5722 strain of M.hyo;

SEQ ID NO: 3 is one embodiment of a nucleotide sequence encoding p97 from the P-5722 strain of M.hyo;

SEQ ID NO: 4 is one embodiment of an amino acid sequence corresponding to p97 from the P-5722 strain of M.hyo;

SEQ ID NO: 5 is one embodiment of a genomic sequence encoding a chimeric PCV1-2 virus;

SEQ ID NO: 6 is one embodiment of a nucleotide sequence corresponding to ORF2 of a porcine circovirus;

SEQ ID NO: 7 is one embodiment of an amino acid sequence corresponding to the ORF2 polypeptide of a porcine circovirus;

SEQ ID NO: 8 is one embodiment of a genomic sequence encoding a chimeric PCV1-2 virus;

SEQ ID NO: 9 is one embodiment of a nucleotide sequence corresponding to ORF2 of a porcine circovirus;

SEQ ID NO: 10 is one embodiment of an amino acid sequence corresponding to the ORF2 polypeptide of a porcine circovirus;

SEQ ID NO: 11 is one embodiment of an amino acid sequence corresponding to the ORF2 polypeptide of a porcine circovirus;

SEQ ID NO: 12 is one embodiment of a nucleotide sequence encoding the amino acid sequence of SEQ ID NO: 11;

SEQ ID NO: 13 is one embodiment of an amino acid sequence corresponding to the ORF2 polypeptide of a porcine circovirus;

SEQ ID NO: 14 is one embodiment of a nucleotide sequence encoding the amino acid sequence of SEQ ID NO: 13;

SEQ ID NO: 15 is one embodiment of an amino acid sequence corresponding to the ORF2 polypeptide of a porcine circovirus;

SEQ ID NO: 16 is one embodiment of a genomic sequence of a non-virulent form of the North American PRRS virus isolate designated P129; and SEQ ID NO: 17 is one embodiment of a nucleotide sequence corresponding to ORF2 to ORFS of the PRRS virus isolate designated ISU-55.

SEQ ID NO: 18 is one embodiment of a nucleotide sequence corresponding to ORF6 and ORF7 of the PRRS virus isolate designated ISU-55.

DETAILED DESCRIPTION OF THE INVENTION

The present invention provides an immunogenic composition including a soluble portion of an M.hyo whole cell preparation, wherein the soluble portion of the M.hyo preparation is substantially free of both (i) IgG and (ii) antigen-bound immunocomplexes. Applicants have surprisingly discovered that the insoluble fraction of the M.hyo whole cell preparation is non-immunogenic. In contrast, the IgG-free M.hyo soluble preparation is immunogenic and can be effectively combined with antigens from other pathogens, such as PCV2 and *Lawsonia intracellularis*, without analytical or immunological interference between the antigens. This makes the M.hyo soluble preparation of this invention an effective platform for multivalent vaccines, including one-bottle, ready-to-use formulations. Applicants have also surprisingly discovered that removing the immunoglobulin and the insoluble cell debris enhances the safety of the immunogenic composition.

The present invention particularly provides a multivalent composition including a soluble portion of an M.hyo whole cell preparation; a porcine circovirus type 2 (PCV2) antigen; and a *Lawsonia intracellularis* antigen, wherein the soluble portion of the M.hyo preparation is substantially free of both (i) IgG and (ii) immunocomplexes comprised of antigen bound to immunocomplexes.

As used in the specification and claims, the singular form "a", "an" and "the" include plural references unless the context clearly dictates otherwise. For example, the term "a protein antigen" includes a plurality of protein antigens, including mixtures thereof.

As used herein, the term "comprising" is intended to mean that the compositions and methods include the recited elements, but do not exclude other elements.

As defined herein, a soluble portion of an M.hyo whole cell preparation refers to a soluble liquid fraction of an M.hyo whole cell preparation after separation of the insoluble material and substantial removal of IgG and antigen-bound immunocomplexes. The M.hyo soluble portion may alternatively be referred to herein as the supernatant fraction, culture supernatant and the like. It includes M.hyo-expressed soluble proteins (M.hyo protein antigens) that have been separated or isolated from insoluble proteins, whole bacteria, and other insoluble M.hyo cellular material by conventional means, such as centrifugation, filtration, or precipitation. In addition to including M.hyo-specific soluble proteins, the soluble portion of the M.hyo whole cell preparation also includes heterologous proteins, such as those contained in the culture medium used for M.hyo fermentation.

The term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten).

As defined herein, an "immunogenic or immunological composition", refers to a composition of matter that comprises at least one antigen which elicits an immunological response in the host of a cellular and or antibody-mediated immune response to the composition or vaccine of interest.

The term "immune response" as used herein refers to a response elicited in an animal. An immune response may refer to cellular immunity (CMI); humoral immunity or may involve both. The present invention also contemplates a response limited to a part of the immune system. Usually, an "immunological response" includes, but is not limited to, one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "immunogenicity" means capable of producing an immune response in a host animal against an antigen or antigens. This immune response forms the basis of the protective immunity elicited by a vaccine against a specific infectious organism.

An "adjuvant" as used herein means a composition comprised of one or more substances that enhances the immune response to an antigen(s). The mechanism of how an adjuvant operates is not entirely known. Some adjuvants are believed to enhance the immune response by slowly releasing the antigen, while other adjuvants are strongly immunogenic in their own right and are believed to function synergistically.

As used herein, the term "multivalent" means a vaccine containing more than one antigen whether from the same species (i.e., different isolates of *Mycoplasma hyopneumoniae*), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

The term "pig" or "piglet" as used herein means an animal of porcine origin, while "sow" refers to a female of reproductive age and capability. A "gilt" is a female pig who has never been pregnant.

As used herein, the term "virulent" means an isolate that retains its ability to be infectious in an animal host.

"Inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal or formalin), sonication, radiation, heat or any other convention means sufficient to prevent replication or growth of the organism while maintaining its immunogenicity.

The term "variant" as used herein refers to a polypeptide or a nucleic acid sequence encoding a polypeptide, that has one or more conservative amino acid variations or other minor modifications such that the corresponding polypeptide has substantially equivalent function when compared to the wild-type polypeptide.

"Conservative variation" denotes the replacement of an amino acid residue by another biologically similar residue, or the replacement of a nucleotide in a nucleic acid sequence such that the encoded amino acid residue does not change or is another biologically similar residue. Examples of conservative variations include the substitution of one hydrophobic residue, such as isoleucine, valine, leucine or methionine for another hydrophobic residue, or the substitution of one polar residue, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

"North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec LAF-exp91 strain of PRRS virus (Mardassi, H. et al., 1995, Arch. Virol. 140:1405-1418); and North American PRRS virus isolate VR 2385 (Meng, X. -J et al., 1994, J. Gen. Virol. 75:1795-1801). Additional examples of North American PRRS virus strains are described herein. Genetic characteristics refer to genomic nucleotide sequence similarity and amino acid sequence similarity shared by North American PRRS virus strains. Chinese PRRS virus strains generally evidence about 80-93% nucleotide sequence similarity with North American strains.

"European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus". Further examples of European PRRS virus strains are described herein.

A genetically modified virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of lung lesions, etc.

An "Infectious clone" is an isolated or cloned genome of the disease agent (e.g. viruses) that can be specifically and purposefully modified in the laboratory and then used to re-create the live genetically modified organism. A live genetically modified virus produced from the infectious clone can be employed in a live viral vaccine. Alternatively, inactivated virus vaccines can be prepared by treating the live virus derived from the infectious clone with inactivating agents such as formalin or hydrophobic solvents, acids, etc., by irradiation with ultraviolet light or X-rays, by heating, etc.

All currently available M.hyo and M.hyo combination vaccines are made from killed whole cell *mycoplasma* preparations (bacterins). In contrast, the present invention employs a soluble portion of a *Mycoplasma hyopneumoniae* (M.hyo) whole cell preparation for combination with the PCV2 antigen and a *Lawsonia intracellularis* antigen, wherein the soluble portion of the M.hyo preparation is substantially free of both (i) IgG and (ii) immunocomplexes comprised of antigen bound to immunoglobulin.

M.hyo has absolute requirements for exogenous sterols and fatty acids. These requirements generally necessitate growth of M.hyo in serum-containing media, such as porcine serum. Separation of the insoluble material from the soluble portion of the M.hyo whole cell preparation (e.g., by centrifugation, filtration, or precipitation) does not remove the porcine IgG or immune complexes. In one embodiment of the present invention, the M.hyo soluble portion is treated with protein-A or protein-G in order to substantially remove the IgG and immune complexes contained in the culture supernatant. In this embodiment, it is understood that protein A treatment occurs post-M.hyo fermentation. This is alternatively referred to herein as downstream protein A treatment. In another embodiment, upstream protein A treatment of the growth media (i.e., before M.hyo fermentation) can be employed. Protein A binds to the Fc portion of IgG. Protein G binds preferentially to the Fc portion of IgG, but can also bind to the Fab region. Methods for purifying/removing total IgG from crude protein mixtures, such as tissue culture supernatant, serum and ascites fluid are known in the art.

In some embodiments, the soluble portion of the M.hyo preparation includes at least one M.hyo protein antigen. In other embodiments, the soluble portion of the M.hyo preparation includes two or more M.hyo protein antigens.

In one embodiment, the M.hyo supernatant fraction includes one or more of the following M.hyo specific protein antigens: M.hyo proteins of approximately 46 kD (p46), 64 kD (p64) and 97 kD (p9'7) molecular weights. In another embodiment, the supernatant fraction at least includes the p46, p64 and p97 M.hyo protein antigens. The M.hyo protein of approximately 64 kD (p64) may be alternatively referred to herein as the p65 surface antigen from M.hyo described by Kim et al. [Infect. Immun. 58(8):2637-2643 (1990)], as well as in U.S. Pat. No. 5,788,962.

Futo et al. described the cloning and characterization of a 46 kD surface protein from M.hyo, which can be employed in the compositions of this invention [J. Bact 177: 1915-1917 (1995)]. In one embodiment, the M.hyo culture supernatant includes the p46 whose corresponding nucleotide and amino acid sequences from the P-5722 strain are set forth in SEQ ID NOs: 1 and 2, respectively. It is further contemplated that variants of such p46 sequences can be employed in the compositions of the present invention, as described below.

Zhang et al. described and characterized a p97 adhesin protein of M.hyo [Infect. Immun. 63: 1013-1019, 1995]. Additionally, King et al. described a 124 kD protein termed Mhpl from the P-5722 strain of M.hyo and presented data suggesting that Mhpl and p97 are the same protein [Vaccine 15:25-35 (1997)]. Such p97 proteins can be employed in the compositions of this invention. In one embodiment, the M.hyo culture supernatant includes the p97 whose corresponding nucleotide and amino acid sequences from the P-5722 strain are set forth in SEQ ID NOs: 3and 4, respectively. It is further contemplated that variants of such p97sequences can be employed in the compositions of the present invention, as described below.

The M.hyo culture supernatant may include further M.hyo specific protein antigens such as, but not limited to, proteins of approximately 41 kD (p41), 42 kD (p42), 89 kD (p89), and 65 kD (p65). See, Okada et al., 2000, J. Vet. Med. B 47:527-533 and Kim et al., 1990, Infect. Immun. 58(8): 2637-2643. In addition, the M.hyo culture supernatant can include M.hyo specific protein antigens of approximately 102 kD (p102) and 216 kD (p216). See, U.S. Pat. Nos. 6,162,435 and 7,419,806 to Minnion et al.

Any M.hyo strain may be used as a starting material to produce the soluble portion of the M.hyo preparation of the compositions of the present invention. Suitable strains of M.hyo may be obtained from commercial or academic sources, including depositories such as the American Type Culture Collection (ATCC) (Manassas, Va.) and the NRRL Culture Collection (Agricultural Research Service, U.S. Department of Agriculture, Peoria, Ill.). The ATCC alone lists the following six strains of M.hyo for sale: M.hyo ATCC 25095, M.hyo ATCC 25617, M.hyo ATCC 25934, M.hyo ATCC 27714, M.hyo ATCC 27715, and M.hyo ATCC 25934D. A preferred strain of M.hyo for use in the embodiments of this invention is identified as strain P-5722-3, ATCC #55052, deposited on May 30, 1990 pursuant to the accessibility rules required by the U.S. Patent and Trademark Office. In view of the widespread dissemination of the disease, strains may also be obtained by recovering M.hyo from lung secretions or tissue from swine infected with known strains causing mycoplasmal pneumonia in swine.

It is understood by those of skill in the art that variants of the M.hyo sequences can be employed in the compositions of the present invention. Such variants could vary by as much as 10-20% in sequence identity and still retain the antigenic characteristics that render it useful in immunogenic compositions. Preferably, the M.hyo variants have at least 80%, preferably at least 85%, more preferably at least 90%, even more preferably at least 95% sequence identify with the full-length genomic sequence of the wild-type M.hyo strain. The antigenic characteristics of an immunological composition can be, for example, estimated by the challenge experiment as provided in the Examples. Moreover, the antigenic characteristic of a modified M.hyo antigen is still retained when the modified antigen confers at least 70%, preferably 80%, more preferably 90% of the protective immunity as compared to the wild-type M.hyo protein.

In one embodiment, M.hyo soluble p46 antigen is included in the compositions of the invention at a final concentration of about 1.5 μg/ml to about 10 μg/ml, preferably at about 2 μg/ml to about 6 μg/ml. It is noted that p46 is the protein used for the M.hyo potency test (see example section below). In another embodiment, the M.hyo antigen can be included in the compositions at a final amount of about 5.5% to about 35% of the M.hyo whole culture protein A-treated supernatant.

The M.hyo soluble preparation of the present invention is both safe and efficacious against M.hyo and is suitable for single dose administration. In addition, Applicants have surprisingly discovered that the M.hyo soluble preparation can be effectively combined with antigens from other pathogens, including PCV2, without immunological interference between the antigens. This makes the M.hyo soluble preparation an effective platform for multivalent vaccines, including the PCV2/M.hyo/*Lawsonia intracellularis* combination vaccine of this invention. The PCV2 antigen may be given concurrently with the M.hyo composition (i.e., as separate single vaccines), but is preferably combined in a ready-to-use, one-bottle vaccine.

In one embodiment, the immunogenic PCV2/M.hyo compositions of the present invention include at least one additional antigen. In one embodiment, the at least one additional antigen is protective against a microorganism that can cause disease in pigs. In some embodiments, the at least one additional antigen component is protective against bacteria, viruses, or protozoans that are known to infect pigs. Examples of such microorganisms include, but are not limited to, the following: porcine reproductive and respiratory syndrome virus (PRRSV), porcine parvovirus (PPV), *Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplasma hyorhinis, Mycoplasma hyosynoviae,* leptospira bacteria, *Lawsonia intracellularis,* swine influenza virus (SIV), *Escherichia coli* antigen, *Brachyspira hyodysenteriae,* porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) and a pathogen causative of Swine Transmis sable Gastroenteritis, or combinations thereof.

In one embodiment, a PCV2/M.hyo combination vaccine according to the present invention is provided as a single-dose, ready-to-use in one bottle vaccine. Such a ready-to-use combination vaccine requires no mixing of separate vaccines, so there is no risk of contamination or additional labor associated with mixing and no requirement to use the mixture within a few hours. Also, a one-bottle PCV2/M.hyo combination vaccine cuts waste and refrigerator storage space in half. Furthermore, one-dose administration eliminates the labor associated with administering a second dose to the animal. It is noted that although PCV2/M.hyo combination vaccines currently exist, they are provided as either a two-dose, ready-to-use vaccine (Circumvent®PCVM) or as a single-dose, 2-bottle vaccine which requires the simultaneous administration of separate vaccines (e.g., Ingelvac CircoFLEX® and Ingelvac MycoFLEX®). Preferably, the PCV2/M.hyo combination according to the present invention would be compatible with other antigens, such as PRRS virus antigen, such that all antigens can be administered in a single-dose.

In some embodiments, the PCV2 antigen component of a PCV2/M.hyo combination vaccine is in the form of a chimeric type-1-type 2 circovirus. The chimeric virus includes an inactivated recombinant porcine circovirus type 1 expressing the porcine circovirus type 2 ORF2 protein. Chimeric porcine circoviruses and methods for their preparation are described in WO 03/049703 A2, and also in U.S. Pat. Nos. 7,279,166 and 7,575,752, which are incorporated herein by reference in their entirety.

In one embodiment, the full-length DNA sequence of the genome of the chimeric PCV1-2 virus corresponds to SEQ ID NO: 5. or variants thereof, as described below. In another embodiment, the immunogenic ORF2 capsid gene of the chimeric PCV1-2 virus corresponds to SEQ ID NO: 6. In a further embodiment, the amino acid sequence of the immunogenic ORF2 protein expressed by the chimeric PCV1-2 virus corresponds to SEQ ID NO: 7.

In yet another embodiment, the full-length DNA sequence of the genome of the chimeric PCV1-2 virus corresponds to SEQ ID NO: 8. In one embodiment, the immunogenic ORF2 capsid gene of the chimeric PCV1-2 virus corresponds to SEQ ID NO: 9. In a further embodiment, the amino acid sequence of the immunogenic ORF2 protein expressed by the chimeric PCV1-2 virus corresponds to SEQ ID NO: 10.

However, the PCV2 ORF2 DNA and protein of the chimeric PCV1-2 virus are not limited to the sequences described above since PCV2 ORF2 DNA and protein is a highly conserved domain within PCV2 isolates.

In some embodiments, the PCV2 antigen component of an M.hyo/PCV2 combination vaccine is in the form of a recombinant ORF2 protein. In one embodiment, the recombinant ORF2 protein is expressed from a baculovirus vector. Alternatively, other known expression vectors can be used, such as including, but not limited to, parapox vectors.

In one embodiment, the recombinant PCV2 ORF2 protein is that of SEQ ID NO: 11, which is encoded by SEQ ID NO: 12 (GenBank Accession No. AF086834). In another embodiment, the recombinant ORF2 protein is that of SEQ ID NO: 13, which is encoded by SEQ ID NO: 14. In yet another embodiment, the recombinant ORF2 protein corresponds to SEQ ID NO: 15. In still another embodiment, the recombinant PCV2 ORF2 protein corresponds to SEQ ID NO: 7. In a still further embodiment, the recombinant PCV2 ORF2 protein corresponds to SEQ ID NO: 10.

However, the present invention is not limited to the particular ORF2 DNA and protein sequences described above. Since PCV2 ORF2 DNA and protein is a highly conserved domain within PCV2 isolates, any PCV2 ORF2 is highly likely to be effective as the source of the PCV2 ORF2 DNA and/or polypeptide as used in the chimeric PCV1-2 virus or in the recombinant PCV2 protein.

An example of a suitable PCV2 isolate from which the PCV2 ORF2 DNA and protein sequences can be derived is PCV2 isolate number 40895 (deposited in the ATCC on Dec. 7, 2001 and assigned ATCC Patent Deposit Designation PTA-3914). The genomic (nucleotide) sequence of the PCV2 isolate number 40895 is available under GenBank accession number AF264042. Other examples of suitable PCV2 isolates from which the PCV2 ORF2 DNA and protein sequences can be derived include, but are not limited to, the following: Imp.999, Imp.1010-Stoon, Imp.1011-

48121, and Imp.1011-48285. The GenBank accession numbers of the genomic sequences corresponding to these PCV2 isolates are AF055391, AF055392, AF055393 and AF055394, respectively.

In some forms, immunogenic portions of PCV2 ORF2 protein are used as the antigenic component in the composition. For example, truncated and/or substituted forms or fragments of PCV2 ORF2 protein may be employed in the compositions of the present invention.

It is understood by those of skill in the art that variants of the PCV2 sequences can be employed in the compositions of the present invention. Such variants could vary by as much as 10-20% in sequence identity and still retain the antigenic characteristics that render it useful in immunogenic compositions. Preferably, the PCV2 variants have at least 80%, preferably at least 85%, more preferably at least 90%, even more preferably at least 95% sequence identify with the full-length genomic sequence of the wild-type PCV2 isolate. The antigenic characteristics of an immunological composition can be, for example, estimated by the challenge experiment as provided in the Examples. Moreover, the antigenic characteristic of a modified PCV2 antigen is still retained when the modified antigen confers at least 70%, preferably 80%, more preferably 90% of the protective immunity as compared to the wild-type PCV2 ORF2 protein.

The PCV2 antigen component is provided in the immunogenic composition at an antigen inclusion level effective for inducing the desired immune response, namely reducing the incidence of or lessening the severity of clinical signs resulting from PCV2 infection.

In one embodiment, a chimeric PCV1-2 virus is included in the compositions of the invention at a level of at least $1.0 \leq RP \leq 5.0$, wherein RP is the Relative Potency unit determined by ELISA antigen quantification (in vitro potency test) compared to a reference vaccine. In another embodiment, a chimeric PCV1-2 virus is included in the composition of the invention at a final concentration of about 0.5% to about 5% of 20-times (20×) concentrated bulk PCV1-2 antigen.

In another embodiment, the PCV2 ORF2 recombinant protein is included in the compositions of the invention at a level of at least 0.2 μg antigen/ml of the final immunogenic composition (μg/ml). In a further embodiment, the PCV2 ORF2 recombinant protein inclusion level is from about 0.2 to about 400 μg/ml. In yet another embodiment, the PCV2 ORF2 recombinant protein inclusion level is from about 0.3 to about 200 μg/ml. In a still further embodiment, the PCV2 ORF2 recombinant protein inclusion level is from about 0.35 to about 100 μg/ml. In still another embodiment, the PCV2 ORF2 recombinant protein inclusion level is from about 0.4 to about 50 μg/ml.

In one embodiment, an immunogenic composition of the present invention includes the inventive combination of at least one M.hyo soluble antigen (e.g., two or more) and a porcine circovirus type 2 (PCV2) antigen, as well as a PRRS virus antigen. In another embodiment, the composition elicits a protective immune response in a pig against M.hyo, PCV2 and PRRS virus.

In one embodiment, a PCV2/M.hyo/PRRS combination vaccine is provided as a single-dose, 2-bottle vaccine. For example, in some embodiments, a PCV2/M.hyo combination is provided as a stable liquid composition in a first bottle and a PRRS virus is provided in a lyophilized state in a second bottle. In some embodiments, additional porcine antigens can be added to either the first or the second bottle.

In one embodiment, the PRRS virus component is provided as a lyophilized, genetically modified live virus. Prior to administration, the PCV2/M.hyo liquid from a first bottle can be used to re-hydrate the PRRS virus in a second bottle so that all three antigens can be administered to the animal in a single-dose. It is noted that although PCV2/M.hyo/PRRS combination vaccines currently exist, they are provided as a single-dose, 3-bottle vaccine which requires the simultaneous administration of three separate vaccines (e.g., Ingelvac CircoFLEX®, Ingelvac MycoFLEX® and Ingelvac®PRRS MLV). The PRRS etiological agent was isolated for the first time in The Netherlands, and named as Lelystad virus. This virus was described in WO 92/21375 (Stichting Centraal Diegeneeskundig Instituut). An isolate of the European PRRS virus was deposited in the Institut Pasteur of Paris, number 1-1102. The North American type was isolated almost simultaneously with the isolation of the European type virus, and is described in WO-93/03760 (Collins et al.) An isolate of the North American type virus was deposited in the American Type Culture Collection (ATCC), number VR-2332.

Different strains have been isolated from both the European and North American virus types. WO 93/07898 (Akzo) describes a European strain, and vaccines derived from it, deposited in CNCM (Institut Pasteur), number 1-1140. Also, WO 93/14196 (Rhone-Merieux) describes a new strain isolated in France, deposited in CNCM (Institut Pasteur), number 1-1153. Furthermore, EP0595436 B1(Solvay) describes a new North American type strain, more virulent than the one initially described, and vaccines thereof. This strain has been deposited in ATCC, but the deposit number is not detailed in the patent application. In addition, ES2074950 BA (Cyanamid Iberica) and its counterpart GB2282811 B2 describe a so-called "Spanish strain", that is different from other European and North American strains. This "Spanish strain" has been deposited in European Animal Cell Culture Collection (EACCC), number V93070108.

Suitable PRRS virus antigens for use in the PCV2/M.hyo/PRRS compositions of the present invention include North American PRRS virus isolates, Chinese PRRS virus strains, and European PRRS virus strains, as well as genetically modified versions of such isolates/strains. In one embodiment, the PRRS virus antigen component employed in the compositions according to the present invention is a North American PRRS virus.

In some embodiments, the PRRS virus antigen component employed in the compositions of this invention is the North American PRRS virus isolate designated P129 or a live, genetically modified version thereof. Preferably, the genetically modified PRRS virus is unable to produce a pathogenic infection yet is able to elicit an effective immunoprotective response against infection by the wild-type PRRS virus.

A genetically modified PRRS virus for use in the compositions of the invention can be produced from an infectious clone. The preparation of an infectious cDNA clone of the North American PRRS virus isolate designated P129 is described in U.S. Pat. No. 6,500,662 which is hereby incorporated fully by reference. The sequence of P129 cDNA is disclosed in Genbank Accession Number AF494042 and in U.S. Pat. No. 6,500,662.

In one embodiment, the nucleotide sequence of a non-virulent form of P129 for use in the compositions of the present invention is represented by SEQ ID NO: 16. However, the present invention is not limited to this sequence. This sequence and the sequences of other non-virulent forms of P129 are described in International Application No.

PCT/IB2011/055003, filed Nov. 9, 2011, the contents of which (including any US National Stage filings based on this International Application) are incorporated herein by reference in their entirety. Preferably, the PRRS virus is modified to prevent down regulation of interferon-mediated function.

In other embodiments, the PRRS virus antigen component employed in the compositions of the invention is the PRRS virus isolate designated ISU-55. The ISU-55 isolate was deposited in the American Type Culture Collection (ATCC), under the accession number VR2430. The nucleotide sequence of the ORF2 to ORF5 genes of the ISU-55 isolate is represented by SEQ ID NO:17. The nucleotide sequence of the ORF6 and ORF7 genes of the ISU-55 isolate is represented by SEQ ID NO: 18.

Another suitable North American PRRS virus isolate which can be used in the compositions is ISU-12, which was deposited in the ATCC under the accession numbers VR2385 [3×plaque purified] and VR2386 [non-plaque purified]. Still other suitable North American PRRS virus isolates which can be employed in the compositions of this invention are the following: ISU-51, ISU-3927, ISU-1894, ISU-22 and ISU-79, which were deposited in the ATCC under the accession numbers VR2498, VR2431, VR2475, VR2429 and VR2474, respectively. Genetically modified versions of any of these ISU isolates can be employed in the compositions of this invention. These ISU isolates and the ISU-55 isolate are described in detail in the following U.S. patents to Paul, et al: U.S. Pat. Nos. 5,695,766, 6,110,467, 6,251,397, 6,251,404, 6,380,376, 6,592,873, 6,773,908, 6,977,078, 7,223,854, 7,264,802, 7,264,957, and 7,517,976, all of which are incorporated herein by reference in their entirety.

In still other embodiments, the PRRS virus antigen component employed in the compositions according to the present invention is the North American type deposited in the American Type Culture Collection (ATCC), number VR-2332 or a genetically modified version thereof. For example, the PRRS virus can be a modified live virus based on the isolate identified as ATCC VR2332, which is employed in INGELVAC® PRRS ATP and INGELVAC® PRRS MLV, from Boehringer Ingelheim Vetmedica, Inc.

In still other embodiments, the PRRS virus antigen component employed in the compositions of the present invention is a European PRRS virus isolate or Lelystad virus or a genetically modified version thereof. An example of a suitable PRRS virus strain is identified as deposit No. 1-1102, described above. Nucleotide and amino acid sequences corresponding to the 1-1102 deposit are described in U.S. Pat. No. 5,620,691 to Wensvoort et al, which is hereby fully incorporated herein by reference. The preparation of an infectious clone of a European PRRS virus isolate or Lelystad virus is described in U.S. Pat. No. 6,268,199 which is hereby fully incorporated herein by reference.

Other examples of suitable PRRS virus isolates include, but are not limited to, those described above. Also, live, genetically modified versions of the PRRS virus isolates can be employed in the compositions of the present invention. An infectious clone can be used to re-create such live genetically modified organisms.

It is understood by those of skill in the art that variants of the PRRS virus sequences can be employed in the compositions of the present invention. Such variants could vary by as much as 10-20% in sequence identity and still retain the antigenic characteristics that render it useful in immunogenic compositions. Preferably, the PRRS virus variants have at least 80%, preferably at least 85%, more preferably at least 90%, even more preferably at least 95% sequence identify with the full-length genomic sequence of the wild-type PPRS virus isolate. The antigenic characteristics of an immunological composition can be, for example, estimated by challenge experiments. Moreover, the antigenic characteristic of a modified PRRS virus antigen is still retained when the modified antigen confers at least 70%, preferably 80%, more preferably 90% of the protective immunity as compared to the wild-type PRRS virus antigen.

In one embodiment, the PRRS virus antigen component is a genetically modified, live virus which is included in the compositions of the invention at a level of at least $2.1 \leq TCID_{50} \leq 5.2$, wherein $TOD_{50}$ is the tissue culture infectious dose 50% determined by antigen quantification (in vitro potency test).

The PCV2 antigen component of the PCV2/M.hyo/PRRS compositions of the invention can be in the form of a chimeric type-1-type 2 circovirus, the chimeric virus including an inactivated recombinant porcine circovirus type 1 expressing the porcine circovirus type 2 ORF2 protein. In another embodiment, the PCV2 antigen component of the PCV2/M.hyo/PRRS compositions of the invention is in the form of a recombinant ORF2 protein.

Suitable PCV2 antigens for use in the PCV2/M.hyo/PRRS compositions can be derived from any of the PCV2 isolates described above, as well as other PCV2 isolates. Suitable PCV2 antigens to be employed in the compositions of the invention include, but are not limited to, the PCV2 sequences described above and variants thereof.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Types of suitable adjuvants for use in the compositions of the present invention include the following: an oil-in-water adjuvant, a polymer and water adjuvant, a water-in-oil adjuvant, an aluminum hydroxide adjuvant, a vitamin E adjuvant and combinations thereof. Some specific examples of adjuvants include, but are not limited to, complete Freund's adjuvant, incomplete Freund's adjuvant, *Corynebacterium parvum, Bacillus* Calmette Guerin, aluminum hydroxide gel, glucan, dextran sulfate, iron oxide, sodium alginate, Bacto-Adjuvant, certain synthetic polymers such as poly amino acids and co-polymers of amino acids, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant (N,N-dioctadecyl-N',N'—bis(2-hydroxyethyl)-propanediamine), "REGRESSIN" (Vetrepharm, Athens, Ga.), paraffin oil, RIBI adjuvant system (Ribi Inc., Hamilton, Mont.), muramyl dipeptide and the like.

Non-limiting examples of oil-in-water emulsions useful in the vaccine of the invention include modified SEAM62 and SEAM ½ formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM ½ is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol.

Another example of an adjuvant useful in the compositions of the invention is SP-oil. As used in the specification and claims, the term "SP oil" designates an oil emulsion comprising a polyoxyethylene-polyoxypropylene block copolymer, squalane, polyoxyethylene sorbitan monooleate and a buffered salt solution. Polyoxyethylene-polyoxypropylene block copolymers are surfactants that aid in suspending solid and liquid components. These surfactants are commercially available as polymers under the trade name Pluronic®. The preferred surfactant is poloxamer 401 which is commercially available under the trade name Pluronic® L-121. In general, the SP oil emulsion is an immunostimulating adjuvant mixture which will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution. In one embodiment, the SP-oil emulsion is present in the final composition in v/v amounts of about 1% to 25%, preferably about 2% to 15%, more preferably about 5% to 12% v/v.

Yet another example of a suitable adjuvant for use in the compositions of the invention is AMPHIGEN™ adjuvant which consists of de-oiled lecithin dissolved in an oil, usually light liquid paraffin.

Other examples of adjuvants useful in the compositions of the invention are the following proprietary adjuvants: Microsol Diluvac Forte® duel emulsion adjuvant system, Emunade adjuvant, and Xsolve adjuvant. Both the Emunade and Xsolve adjuvants are emulsions of light mineral oil in water, but Emunade also contains alhydrogel, and d,1-α-tocopheryl acetate is part of the XSolve adjuvant. A still further example of a suitable adjuvant for use in the compositions of the invention is ImpranFLEX™ adjuvant (a water-in-oil adjuvant). A still further example of a suitable adjuvant is a Carbomer (Carbopol®) based adjuvant. Preferred Carbopol® adjuvants include Carbopol® 934 polymer and Carbopol®941 polymer.

In one embodiment, the adjuvant or adjuvant mixture is added in an amount of about 100 µg to about 10 mg per dose. In another embodiment, the adjuvant/adjuvant mixture is added in an amount of about 200 µg to about 5 mg per dose. In yet another embodiment, the adjuvant/adjuvant mixture is added in an amount of about 300 µg to about 1 mg/dose.

The adjuvant or adjuvant mixture is typically present in the vaccine composition of the invention in v/v amounts of about 1% to 25%, preferably about 2% to 15%, more preferably about 5% to 12% v/v.

Other "immunomodulators" that can be included in the vaccine include, e.g., one or more interleukins, interferons, or other known cytokines. In one embodiment, the adjuvant may be a cyclodextrin derivative or a polyanionic polymer, such as those described in U.S. Pat. Nos. 6,165,995 and 6,610,310, respectively.

A further aspect relates to a method for preparing an immunogenic composition according to the present invention. This method comprises i) culturing M.hyo in a suitable media over periods ranging from 18-144 hours; ii) subsequently inactivating the M. hyo culture; iii) harvesting the inactivated culture fluid, wherein the inactivated culture fluid comprises an M.hyo whole cell preparation comprising both a soluble liquid fraction and insoluble cellular material; iv) separating the soluble liquid fraction from the insoluble cellular material; v) substantially removing both IgG and antigen/immunoglobulin immunocomplexes from the separated soluble liquid fraction to form a soluble portion of the M.hyo whole cell preparation; and vi) subsequently combining the soluble portion of the M.hyo whole cell preparation with a PCV2 antigen and a *Lawsonia intracellularis* antigen.

An example of a suitable media for culturing M.hyo is PPLO Broth (*Mycoplasma* Broth Base), which when supplemented with nutritive enrichments, is used for isolating and cultivating *Mycoplasma*.

In some embodiments, the culture of M.hyo is grown until late log phase growth, after which the culture is inactivated. In some other embodiments, the culture is inactivated by raising the pH (e.g., to about 7.8). This occurs by exposing the production culture to an inactivation agent, such as binary ethylenimine (BEI). The BEI is generated in situ during incubation of L-bromoethylamine hydrobromide (BEA) in the production culture. Subsequently, the pH of the inactivated culture is neutralized, such as by adding an equivalent amount of an agent that neutralizes the inactivation agent within the solution. In some embodiments, the inactivation agent is BEI and the neutralization agent is sodium thiosulfate. In one embodiment, the pH of the inactivated culture is adjusted to about 7.4 by adding sodium thiosulfate.

In some embodiments, the soluble liquid fraction of the M.hyo whole cell preparation is separated from the insoluble cellular material using conventional methods. In one embodiment, this separation is by a filtration step. In another embodiment, this separation is by a centrifugation step. In yet another embodiment, the separation is by a precipitation step.

In one embodiment, the soluble liquid fraction of an inactivated, neutralized M.hyo whole cell preparation is treated with Protein A resin to substantially remove both the IgG and antigen/immunoglobulin immunocomplexes therein. In other embodiments, Protein G resin can be used to substantially remove both the IgG and antigen/immunoglobulin immunocomplexes contained in the soluble liquid fraction. Methods for removing both IgG and antigen/immunoglobulin immunocomplexes with either Protein A or Protein G resins are well known in the art.

According to a further aspect, the method for preparing a multivalent immunogenic composition according to the present invention comprises preparing the soluble M.hyo antigen as described above and mixing this with a PCV2 antigen, a suitable adjuvant, and one or more pharmaceutically-acceptable carriers. This method also includes adding at least one additional porcine antigen, specifically a *Lawsonia intracellularis* antigen and optionally includes adding still further porcine antigens, such as, but not limited to, PRRS virus antigen as described above.

A further aspect of the present invention relates to a kit. A "kit" refers to a plurality of components which are grouped together. In one embodiment, a kit according to the present invention includes a bottle (or other suitable receptacle) comprising an immunogenic composition. This immunogenic composition includes both a PCV2 antigen and the soluble portion of a *Mycoplasma hyopneumoniae* (M.hyo) whole cell preparation, as well as a *Lawsonia intracellularis* antigen, wherein the soluble portion of the M.hyo preparation is substantially free of both (i) IgG and (ii) antigen/immunoglobulin immunocomplexes. Optionally, the kit can further include an instruction manual. The instruction manual includes the information to administer the immunogenic composition.

In some embodiments, the PCV2/M.hyo combination in the bottle of the kit is provided as a ready-to-use liquid composition. In other embodiments, the kit includes a second bottle comprising PRRS virus antigen. In some embodiments, the PRRS virus antigen is in the form of a genetically modified, live virus which is provided in a lyophilized state. In such instances, the instruction manual will include the directions for re-hydrating the PRRS virus component with the liquid contents from bottle containing the PCV2/M.hyo combination. The instruction manual will also include the information to administer the resultant PCV2/M.hyo/PRRS trivalent formulation(s).

In some embodiments, an immunogenic composition according to this invention is administered to pigs having maternally derived antibodies against M.hyo. In other embodiments, an immunogenic composition of the present invention is administered to pigs having maternally derived antibodies against both M.hyo and PCV2.

In some embodiments, a multivalent immunogenic composition according to the present invention is administered to a piglet aged 3 weeks or older. However, it is contemplated that a multivalent vaccine composition according to the invention may also be used to re-vaccinate gilts pre-breeding. As is known in the art, a gilt is a female pig that has never been pregnant. Vaccinated gilts will pass maternally derived antibodies onto their suckling newborns via colostrum.

It is further contemplated that a multivalent vaccine according to the invention can be used to annually re-vaccinate breeding herds. Preferably, a multivalent vaccine according to the present invention is administered to pigs (e.g., piglets or gilts) in one dose. In one embodiment, a multivalent vaccine according to the present invention does not require mixing of separate monovalent vaccines prior to administration, i.e., it is provided as a ready-to-use PCV2/M.hyo formulation contained in one bottle. In another embodiment, a multivalent formulation requires mixing of a divalent vaccine according to the present invention contained in a first bottle with a monovalent vaccine contained in a second bottle. In one embodiment, the monovalent vaccine contained in the second bottle includes PRRS virus antigen. Optionally, additional antigens can be added to either of these bottles.

In some embodiments, the onset of immunity is from 2-3 weeks post-vaccination with a multivalent vaccine composition according to the present invention. In other embodiments, the duration of immunity is about 17-23 weeks post-vaccination with a multivalent vaccine composition according to the present invention.

The following examples set forth preferred materials and procedures in accordance with the present invention. However, it is to be understood that these examples are provided by way of illustration only, and nothing therein should be deemed a limitation upon the overall scope of the invention.

EXAMPLES

Example 1

*Mycoplasma* Hyopneumoniae Production Methods for PCV2 Combinable M.hyo Antigen

M.hyo Fermentation and Inactivation

Media for seed scale and antigen production was prepared as follows. Porcine heart derived Pleuropenumonia-like Organism (PPLO) Broth (BD Biosciences catalog No. 21498) was made per manufacturer's directions (i.e., 21 g/L) and yeast extract solution was made at 21 g/L in USP. Yeast extract solution was then added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. The medium was inoculated with a 10% v:v of a log phase culture of *M. hyopeumoniae* (strain P-5722-3). The culture was held at 37° C. and pH and dO were maintained at 7.0 and 25%, respectively. At late log phase growth, the culture was inactivated by binary ethylenimine (BEI), an aziridine compound, produced from 2-bromoethylamine hydrobromide. Specifically, the inactivation occurred by raising the pH to 7.8 by adding 2-bromoethylaminehydrobromide (BEA) to a final concentration of 4 mM and incubating for 24 hours. The BEI was neutralized by addition of sodium thiosulfate at a 1:1 molar ratio followed by additional 24 hour incubation. The inactivated culture fluid was held at 2-8° C. until further processing.

Example 2

Chimeric Porcine Circovirus (cPCV)1-2 Production Methods

The cPCV1-2 was constructed by cloning the immunogenic capsid gene of the pathogenic porcine circovirus type 2 (PCV2) into the genomic backbone of the nonpathogenic porcine circovirus type 1 (PCV1). The procedure for construction of the chimeric DNA clone is described, for example, in U.S. Pat. No. 7,279,166, which is incorporated herein by reference in its entirety. An infectious stock of the chimeric virus was acquired from Dr. X. J. Meng, Virginia Polytechnic Institute and State University, Blacksburg, Va., and was used to infect Porcine Kidney (PK)-15 cells grown in Minimum Essential Medium (MEM) supplemented with 0.05% lactalbumin hydrolysate (LAH), 30 μg/mL gentamicin sulfate, and 5% fetal bovine serum. The resulting cPCV1-2 infected PK-15 cells were further expanded by serial passing four more times using the same growth medium except with 2-3% fetal bovine serum. The fifth passage was frozen, thawed and filtered, and the resulting lysates were used to prepare a pre-master seed and subsequent master seed.

The medium which was used for producing virus seeds was the same as that used in producing virus stock. For the growth medium, MEM, OptiMEM, or equivalent is the basal medium which can be used for planting the PK-15 cell line for outgrowth. The growth medium can be supplemented with up to 10% bovine serum, up to 0.5% lactalbumin hydrolysate, up to 0.5% bovine serum albumin, and up to 30 μg/mL gentamicin. For the virus propagation medium, MEM, OptiMEM, or equivalent is used. The virus propagation medium can be supplemented with up to 0.5% lactalbumin hydrolysate, up to 2% bovine serum, up to 0.5% bovine serum albumin, and up to 30 μg/mL gentamicin. Up to 5 g/L glucose and up to 5 mmol/L L-glutamine can be added to the growth medium and/or the virus propagation medium as required to sustain the cells.

The cPCV1-2 master seed virus are added to a cell suspension of PK-15 cells and adsorbed for up to 3 hours. Seed virus is diluted in growth basal medium to provide a multiplicity of infection (MOI) of 0.1-0.0001.

Cultures of PK-15 cells are initially inoculated with working seed virus at the time of cell planting, or when cells reach approximately 20% to 50% confluency. This initial passage may be referred as "One-Step Infection Method" for the production of antigen stock, or may be further used for serial passages. For serial passages, the cPCV1-2 infected PK-15 cells are further expanded up to passage 7 by serial splits at the ratio of 1:5-20 for virus propagation. Culture medium containing an infected cell suspension from the previous passage serves as seed material for the next passage. The cPCV1-2 infected cells are incubated for three (3) to 14 days for each passage at 36±2° C. when cells reach ≥90% confluency. The cPCV1-2 virus causes observable cytopathic changes during viral replication. At harvest, rounding of cells and considerable floating debris is observed. Cultures are also observed for visual evidence of bacterial or fungal contamination. The incubation time between harvests for the cPCV antigen is provided in Table 1 below:

TABLE 1

Minimum and Maximum Times for Harvesting cPCV Antigen

| Method | Minimum/ MaximumTime | Temperature Range |
|---|---|---|
| One-Step Infection | 5 to 16 days | 36 ± 2° C. |
| Serial Passage (MSV + 3 to MSV + 7) | 16 to 36 Days | 36 ± 2° C. |

The cPCV1-2 culture fluids are harvested into sterile vessels and are sampled for mycoplasma testing using known methods. Multiple harvests may be conducted from roller bottles, bioreactors and perfusion vessels.

Prior to inactivation of the harvested cPCV1-2 virus, one or more antigen lots may be concentrated (e.g., up to 60×) by ultrafiltration. The concentrates may be washed with balanced salt solution to reduce serum proteins.

The method of inactivation, attenuation, or detoxification of the cPCV1-2 virus will now be described. After cPCV antigen concentration, Beta-propiolactone (BPL) is added to the pooled cPCV1-2 viral material to obtain an approximate concentration of 0.2% v/v. The pooled viral fluids are then agitated for a minimum of 15 minutes and then the inactivating bulk antigen fluids are transferred to a second sterile vessel. The transferred antigen fluids are maintained at 2-7° C., with constant agitation, for a minimum of 24 hours. After a minimum of 24 hours, a second addition of 0.2% v/v of BPL is added to the pooled suspension. The contents are subsequently agitated, transferred to a third vessel, and maintained at 2-7° C., with constant agitation, for an additional time of not less than 84 hours. In general, the total inactivation time is not less than 108 hours and not more than 120 hours. The inactivation method is summarized in Table 2 below.

TABLE 2

Inactivation Method

| Inactivant | Final Concentration | Temp. Range | Time-Hours (Min/Max) |
|---|---|---|---|
| Beta-propiolactone (BPL) | 0.4% v/v(2 × 0.2% v/v additions) | 2-7° C. (w/Agitation) | 108-120 |

The inactivation is terminated by the addition of a final concentration of not more than 0.1M solution of sodium thiosulfate. The pH of the inactivated antigen stock is adjusted to about 6.8 using NaOH or HCl. Following inactivation, a representative sample is taken from the pool and tested for completion of inactivation. The inactivated cPCV1-2 antigen product is standardized to a meet a target of greater than 1.0 RP as measured via potency ELISA.

Example 3

Down Stream Processing of M. hyo Antigens and Analytical Testing of these Processed Antigens Down Stream Processing of M.hyo Antigens:

Inactivated fermentation fluid (prepared as described above in Example 1) was treated for each indicated group as follows. These processed M.hyo antigens were employed in Example 4 below.

T02: (Whole Bulk) not processed.

T03: (10× UF concentrated) Concentrated via tangential flow filtration via a 100 KDa molecular weight cutoff membrane (hollow fiber). Final volume reduction was equal to 10×.

T04 & T05: (10× UF concentrated & centrifuged) Concentrated *mycoplasma* cells (from T03) were collected and washed one time with PBS via centrifugation at ~20,000×g (Sorvall model RCSB).

T06 & T07: (10× centrifuged) Inactivated fermentation fluid was centrifuged at ~20,000×g (Sorvall RCSB) and washed one time by resuspending the cells in PBS followed by an additional centrifugation. Final volume reduction was equal to 10×.

T08: (10× centrifuged & Heated) *Mycoplasma* cells were concentrated and washed per T06 and heated to 65° C. for 10 minutes.

T09: (Cell-free supernatant) Supernatant collected from the first centrifugation as described for T06 was filter sterilized through a 0.2 micron filter (Nalgene).

T10: (Cell-free supernatant-Protein-A treated) Sterile supernatant (prepared per T09) was mixed with Protein A resin (Protein A Sepharose, Pharmacia Inc) at a 10:1 volume ratio for 4 hours. Resin was removed sterile filtration and filtered fluid was stored at 2-8° C. This process uses post-fermentation "downstream" protein A treatment to remove antibodies and immunocomplexes. Although the present invention does not preclude upstream protein A treatment, the present inventors have found that in the case of M.hyo, upstream protein A treatment of the growth media led to p46 results which were lower and inconsistent as compared to untreated media (data not shown).

Analytical Testing of M.hyo Downstream Processed Antigens

The downstream processed M.hyo antigens preparations (prepared as described above) were tested for the recovery of M.hyo specific p46 antigen, and the presence of PCV2 antibody. In addition, these M.hyo antigen preparations were tested for the presence of Torque Teno Virus (TTV), including genotype 1 (g1TTV) and genotype 2 (g2TTV). The results are presented below in Table 3.

TABLE 3

Characterization of M.hyo Downstream Processed Antigens

| Treatment | Bulk M.Hyo p46 RU/mL | PCV2 ab S/P ratio | qPCR DNA g1TTV | qPCR DNA g2TTV |
|---|---|---|---|---|
| Whole bulk | 809 | 0.248 | 1.00E+03 | 1.78E+03 |
| 10× UF concentrated | 6666 | 0.819 | 1.00E+03 | 9.94E+03 |

TABLE 3-continued

Characterization of M.hyo Downstream Processed Antigens

| Treatment | Bulk M.Hyo p46 RU/mL | PCV2 ab S/P ratio | qPCR DNA g1TTV | qPCR DNA g2TTV |
|---|---|---|---|---|
| 10× UF conc. + Centrifuge | 614 | 0.019 | 0 | 0 |
| 10× Centrifuged | 763 | −0.015 | 1.90E+02 | 1.91E+02 |
| 10× Centrifuged + Heated | 690 | −0.012 | 0 | 2.07E+02 |
| Cell-free supe | 719 | 0.242 | 4.20E+02 | 3.23E+03 |
| Cell-free supe (Prot A) | 826 | −0.014 | 0 | 2.06E+03 |

With reference to Table 3 above, recovery of the M.hyo-specific p46 antigen was demonstrated for each of the M.hyo downstream processed antigen preparations. In addition, the following treatments successfully removed PCV2 antibody: 10× UF concentrated & centrifuged, 10× centrifuged, 10× centrifuged & heated and Cell-free supernatant (Protein-A treated). With respect to TTV, the following treatments successfully removed g1TTV: 10× UF concentrated & centrifuged, 10× centrifuged & heated, and Cell-free supernatant (Protein-A treated). Only the treatment designated 10× UF concentrated & centrifuged removed g2TTV. Torque teno virus isolates, including genotypes 1 and 2 are described in US20110150913, which is incorporated herein by reference in its entirety.

Since it is known in the art that Protein A binds IgG, it is understood by those of ordinary skill in the art that not only PCV2 antibody, but other swine antibodies, including PRRS antibody, HPS antibody, and SIV antibody will be effectively removed by the Protein-A treatment. This makes the Cell-free Protein-A treated M.hyo supernatant of this invention compatible not only with PCV2 antigen, but also with other porcine antigens due to the lack of immunological interference between the antigens. Additionally, the removal of the non-protective cell debris and removal of the immunoglobulin and antigen/immunoglobulin complexes is reasonably expected to make a safer vaccine.

Example 4

Preparation of M.hyo Experimental Vaccine Formulations

All experimental M.hyo vaccines were formulated with a final concentration of 5% Amphigen adjuvant. In addition, all vaccines were standardized with a p46 ELISA and preserved with thimerosol. The experimental vaccine formulations were prepared with M.hyo antigens processed according to treatments T02-T10 above. In addition, Treatment T01 corresponded to a placebo (no M.hyo antigen, only 5% Amphigen adjuvant) whereas Treatment T11 is a positive control corresponding to an expired bacterin-based M.hyo vaccine (RespiSure-ONE®, Pfizer Animal Health). These formulations are described in Table 4 below.

TABLE 4

M.hyo Experimental Vaccine Formulations

| Treatment | IVP Serial* | Target p46 units/ds | M Hyo antigen (mL) | Adjuvant (mL) | Formulation Vol. (mL) |
|---|---|---|---|---|---|
| T01 | 123639 (Placebo) | 5% Amphigen only, No Antigen | | | |
| T02 | L100211A | 452 | 279.36 | 250 | 1000 |
| T03 | L100211B | 452 | 6.78 | 50 | 200 |
| T04 | L100211C | 452 | 73.62 | 50 | 200 |
| T05 | L100211D | 816 | 132.90 | 50 | 200 |
| T06 | L100211E | 452 | 59.24 | 50 | 200 |
| T07 | L100211F | 816 | 106.95 | 50 | 200 |
| T08 | L100211G | 452 | 65.51 | 50 | 200 |
| T09 | L100211H | 452 | 62.87 | 50 | 200 |
| T10 | L100211J | 452 | 54.72 | 50 | 200 |
| T11 | A827870 | Expired "RespiSure" vaccine | | | |

*Investigational Veterinary Product (IVP) Serial

Example 5

Evaluation of the in Vivo Efficacy of M.hyo Vaccines with M.hyo Antigens from Different Downstream Processes This study was conducted to evaluate the in vivo efficacy of Mycoplasma hyopneumoniae (M hyo) vaccines with M hyo antigens from different downstream processes (DSP). Pigs at 3 weeks of age were intramuscularly inoculated with a single dose of the different vaccine formulations described in Table 4 above. Sixteen animals were included in each of the treatment groups. Animals were challenged 21 days after vaccination with a virulent M.hyo field isolate. Animals were necropsied 28 days after challenge and the lungs were removed and scored for consolidation consistent with M.hyo infection. The primary criterion for protection against M.hyo challenge was lung consolidation scores. It is generally accepted that there is a relationship between the size of the lung lesions caused by enzootic pneumonia and an adverse effect on growth rate. Table 5 below contains the lung lesion scores for the respective treatment groups. Statistical significance was determined by a Mixed Model Analysis of lung scores for each group.

TABLE 5

Lung Lesion Results

| Treatment | Description | p46 RP Target/ Observed | % Lung Lesions Back Transformed LS Means | Range % Lung with Lesions | Contrast | p-value | Significant |
|---|---|---|---|---|---|---|---|
| T01 | Placebo (5% Amphigen) | N/A | 11.7 | 1.2-44.3 | N/A | N/A | N/A |
| T02 | Whole bulk | 13/15.6 | 1.2 | 0.1-18.5 | T01 vs 02 | 0 | Yes |
| T03 | Whole bulk UF 10× | 13/11.9 | 0.3 | 0.0-2.8 | T01 vs 03 | 0 | Yes |

TABLE 5-continued

Lung Lesion Results

| Treatment | Description | p46 RP Target/ Observed | % Lung Lesions Back Transformed LS Means | Range % Lung with Lesions | Contrast | p-value | Significant |
|---|---|---|---|---|---|---|---|
| T04 | UF 10× + Centrifuged | 13/28.1 | 5.9 | 0.0-40.5 | T01 vs 04 | 0.1589 | No |
| T05 | UF 10× + Centrifuged | 24/48.2 | 3.7 | 0.0-42.3 | T01 vs T05 | 0.0309 | Yes |
| T06 | 10× Centrifuged | 13/30.4 | 4.7 | 0.0-23.6 | T01 vs 06 | 0.0388 | Yes |
| T07 | 10× Centrifuged | 24/57.4 | 4.6 | 0.3-37.3 | T01 vs T07 | 0.0323 | Yes |
| T08 | 10× Centrifuged + Heat | 13/17.7 | 4.5 | 0.3-21.7 | T01 vs T08 | 0.

containing fluids were passed through the Protein A resin at a flow rate of 100 cm/hr. The flow through was collected and sterilized via 0.2 μM filter.

T05: This is a positive control corresponding to a Fostera PCV-like formulation (no M.hyo antigen). The level of the chimeric virus in this Fostera PCV-like formulation was approximately at Minimum Immunizing Dose (MID) formulation levels. The chimeric virus was included in the PCV2/M.hyo experimental vaccines at similar formulation levels.

All experimental PCV2/M.hyo vaccines were formulated with different adjuvant formulations. The experimental vaccine formulations were prepared with M.hyo antigens processed according to treatments T02-T04 above. In addition, Treatment T01 corresponded to a placebo (sterile saline).

All vaccines were standardized with a p46 ELISA and preserved with thimerosol.

These experimental formulations are described in Table 6 below, wherein the symbol * indicates the M hyo antigen from global M hyo seed, Protein A treated supernatant and the symbol ** indicates Investigational Veterinary Product (IVP) serial.

TABLE 6

PCV2/M.hyo Experimental Vaccine Formulations Used for PCV2 Efficacy Study

| Treatment | IVP Serial** | PCV1-2 Ag | M Hyo* Ag | Adjuvant | Other |
|---|---|---|---|---|---|
| T01 | 87-244-DK (Placebo) | | NA | | Sterile Saline |
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | L0611RK04 | | NA | 20% SLCD | |

Pigs at 3 weeks of age were intramuscularly inoculated with a single dose of the different vaccine formulations described in Table 6 above. Sixteen animals were included in each of the treatment groups. Animals were challenged 21 days after vaccination with a virulent PCV2 field isolate.

Figure 3:
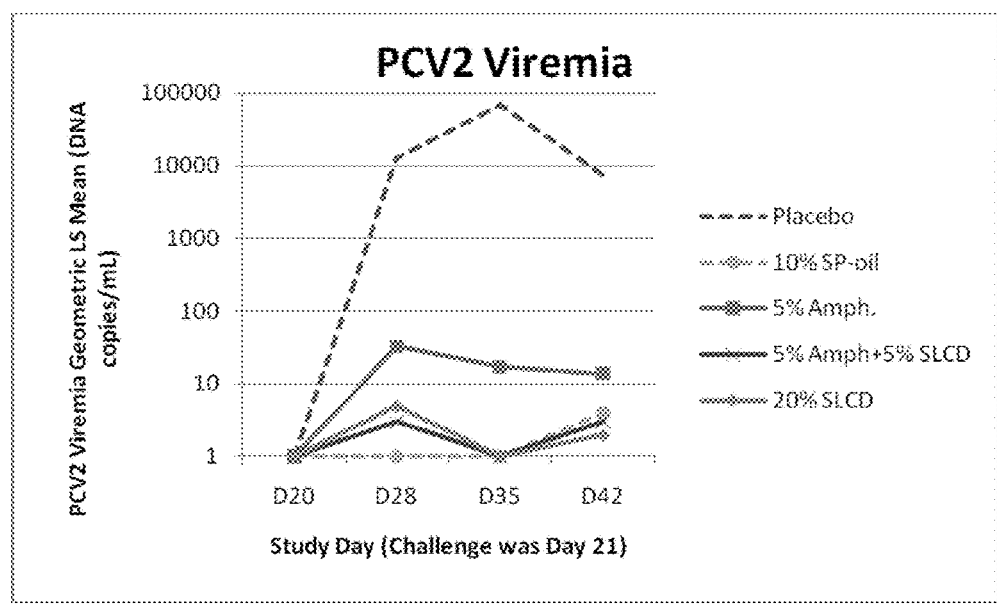
FIG. 3 is a graph showing the PCV2 viremia results (PCV2 Quantitative PCR) observed with PCV/M.hyo vaccine formulations employing different adjuvant platforms.

FIG. 3 is a graph showing the PCV2 viremia results (PCV2 Quantitative PCR) observed with the different adjuvant platforms. It is noted that PCV2 viremia was used as the primary efficacy variable. The PCV2 viremia results are presented as DNA copies/ml. As shown in FIG. 3, all treatments had significantly less viremia compared to the placebo on days 28, 35 and 42 (challenge was day 21).The 10% SP-oil adjuvant had significantly less viremia compared to 5% Amphigen at Days 28 and 35. The 5% Amphigen plus 5% SLCD adjuvant had significantly less viremia compared to 5% Amphigen at Days 28 and 35. The 20% SLCD adjuvant platform had significantly less viremia compared to 5% Amphigen at Days 28, 35 and 42.

PCV2 Serology, PCV2 fecal shed, PCV2 nasal shed, Cell Mediated Immune (CMI) responses, lymphoid depletion, and Immunohistochemistry (IHC) were also monitored as secondary efficacy variables. These results will now be described below.

Figure 4:
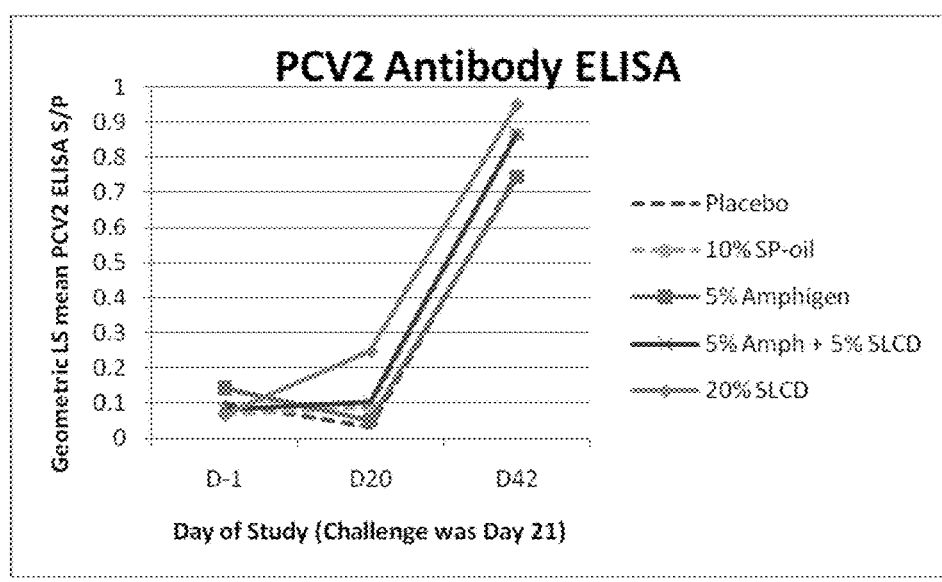
FIG. 4 is a graph showing the PCV2 antibody ELISA (S/P) serological results observed with PCV/M.hyo vaccine formulations employing different adjuvant platforms on days 1, 20, and 42 of challenge.

FIG. 4 is a graph showing the PCV2 ELISA results on days 1, 20 and 42 of the study (challenge was day 21). The status of each sample was expressed as a sample to positive ratio (S/P). As shown in FIG. 4, 20% SLCD was the only treatment which was significantly different from the placebo (T01) at both day 20 and day 42. Also, 5% Amphigen was the only treatment not significantly different from the placebo at day 20.

Figure 5:
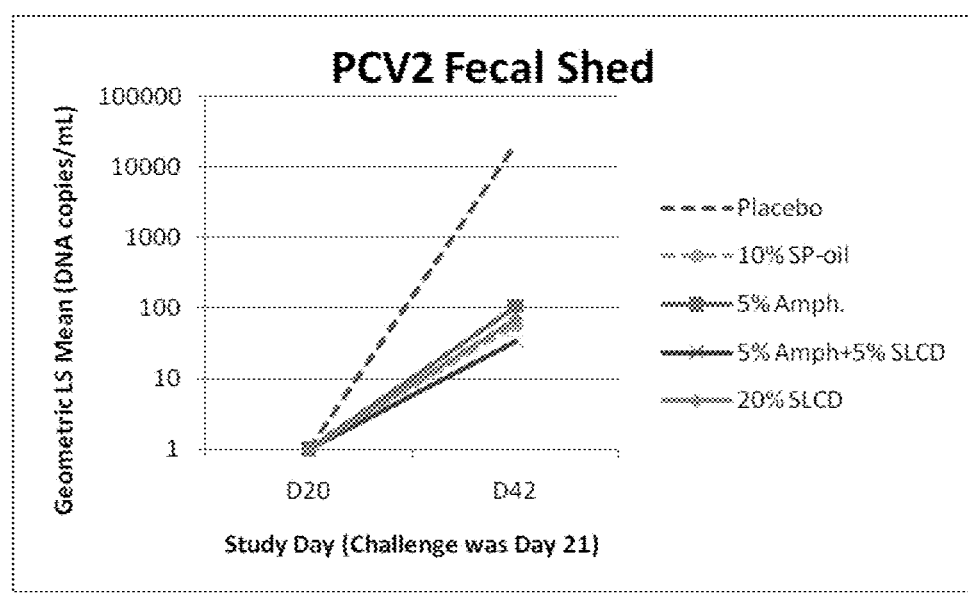
FIG. 5 is a graph showing the PCV2 fecal shed obtained with the T02-T04 treatments described in Example 7 vs. a placebo (T01). The results are expressed as PCV2 DNA copies/ml.

FIG. 5 is a graph showing the PCV2 fecal shed obtained with the T02-T04 treatments vs. the placebo (T01). These results are expressed as PCV2 DNA copies/ml. The results in FIG. 5 indicate that all treatments had significantly less fecal shed when compared to the placebo at day 42. In addition, 5% Amphigen & 5% SLCD (T04) had significantly less fecal shed as compared to 5% Amphigen (T03) at day 42. No other treatment differences were noted.

Figure 6:
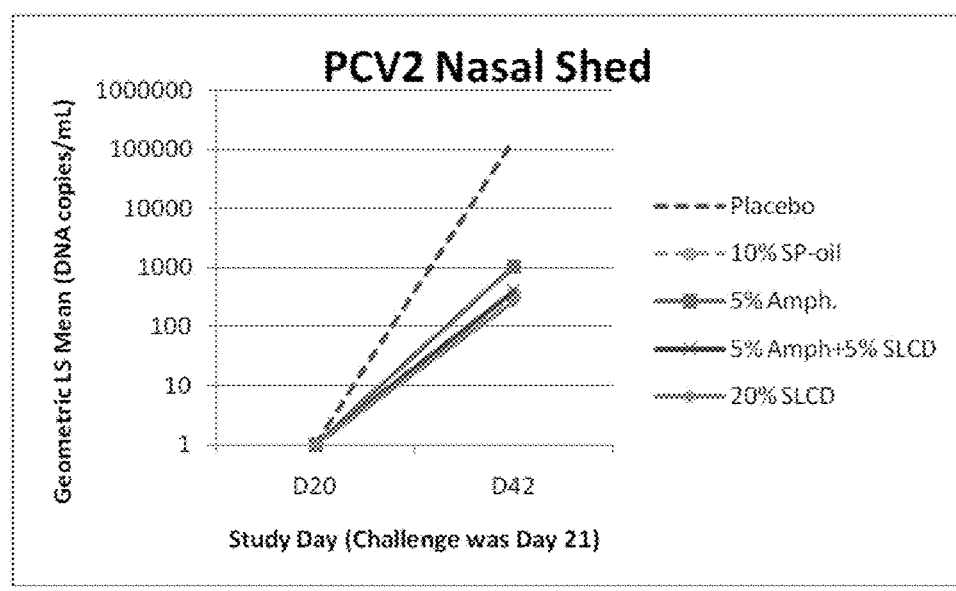
FIG. 6 is a graph showing the PCV2 nasal shed obtained with the T02-T04 treatments described in Example 7 vs. the placebo (T01). The results are expressed as PCV2 DNA copies/ml.

FIG. 6 is a graph showing the PCV2 nasal shed obtained with the T02-T04 treatments vs. the placebo (T01). These results are expressed as PCV2 DNA copies/ml. The results in FIG. 6 indicate that all treatments had significantly less nasal shed when compared to the placebo at day 42. In addition, 20% SLCD (T05) had significantly less nasal shed compared to 5% Amphigen (T03) at day 42. No other treatment differences were noted.

Figure 7A:
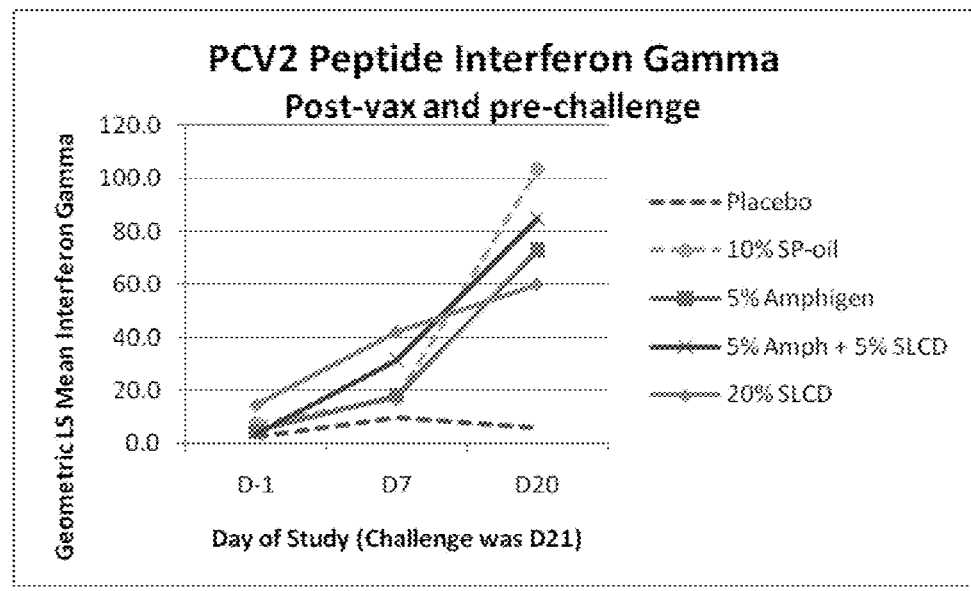
FIG. 7A and FIG. 7B are graphs showing the results of an interferon-gamma (IFN-γ) test that measures PCV2-specific cellular mediated immune (CMI) responses. The results of pos-vaccination/pre-challenge are presented in FIG. 7A, and the results of post-vaccination/post-challenge are presented in FIG. 7B. Stimulation of $5 \times 10^6$ cells was considered significant.
Figure 7B:
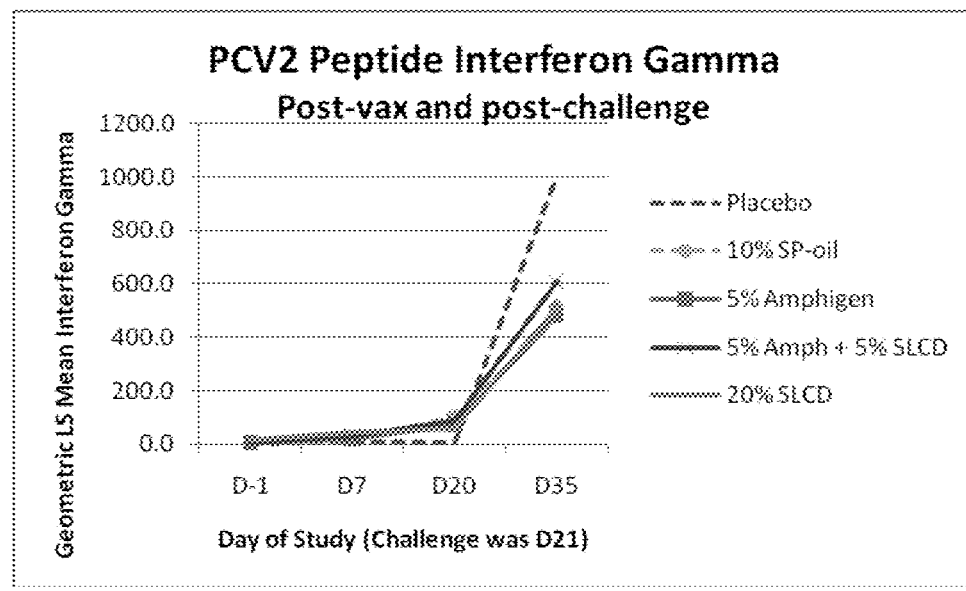

FIG. 7A and FIG. 7B are graphs showing the results of an interferon-gamma (IFN-γ) test that measures PCV2-specific cellular mediated immune (CMI) responses. The CMI results are shown post-vaccination/pre-challenge (FIG. 7A), and post-vaccination/post-challenge (FIG. 7B). In these graphs, stimulation of $5 \times 10^6$ cells was considered significant ( . . . ). All PCV2/M.hyo experiment vaccines gave a detectable IFN-γ response post-vaccination. The 10% SP-oil (T02) drove the strongest IFN-γ response post-vaccination. The 20% SLCD (T05) induced an earlier response, but the lowest response at day 20. There was a large post-challenge response, especially seen in the placebo group. Additionally, the post-challenge response was lower in the vaccinated pig treatment groups as compared to the placebo group.

Table 7 below shows the lymphoid depletion obtained with the experimental treatments contrasted to the placebo.

TABLE 7

PCV2 Histopathology (Lymphoid Depletion)

| | Lymphoid Depletion | | | Contrasted to Placebo | |
|---|---|---|---|---|---|
| Treatment | Positive | Negative | % Ever Pos. | P-value | Significant |
| Placebo | 9 | 7 | 56% | NA | NA |
| 10% SP-oil | 1 | 15 | 6% | 0.0059 | Yes |
| 5% Amphigen | 1 | 15 | 6% | 0.0059 | Yes |
| 5% Amph + 5% SLCD | 0 | 16 | 0% | 0.0008 | Yes |
| 20% SLCD | 1 | 15 | 6% | 0.0059 | Yes |

The results presented in Table 7 above show that all vaccines afforded strong protection against lymphoid depletion. Also, no statistically significant vaccine treatment contrasts were observed. Table 8 below shows the immunohistochemistry obtained with the experimental treatments contrasted to the placebo.

TABLE 8

PCV2 Histopathology (Immunohistochemistry)

| | Immunohistochemistry | | | Contrasted to Placebo | |
|---|---|---|---|---|---|
| Treatment | Positive | Negative | % Ever Pos. | P-value | Significant |
| Placebo | 12 | 4 | 75% | NA | NA |
| 10% SP-oil | 0 | 16 | 0% | 0.0001 | Yes |

TABLE 8-continued

PCV2 Histopathology (Immunohistochemistry)

| | Immunohistochemistry | | | Contrasted to Placebo | |
|---|---|---|---|---|---|
| | | | % Ever | | |
| Treatment | Positive | Negative | Pos. | P-value | Significant |
| 5% Amphigen | 1 | 15 | 6% | 0.0002 | Yes |
| 5% Amph + 5% SLCD | 0 | 16 | 0% | 0.0001 | Yes |
| 20% SLCD | 0 | 16 | 6% | 0.0001 | Yes |

The results presented in Table 8 above show that all vaccines afforded strong protection against PCV2 colonization as evidenced by immunohistochemistry. Also, no statistically significant vaccine treatment contrasts were observed.

In conclusion, the results presented in this example demonstrate that the M.hyo soluble antigen preparation does not interfere with PCV2 efficacy. The results also show that all the PCV/M.hyo experimental vaccine formulations provide efficacy against PCV2 challenge. Additionally, the results indicate that there are some statistical and numerical differences obtained with the different adjuvant formulations, with 10% SP-oil yielding the strongest efficacy.

Example 8

Evaluation of M.hyo Efficacy of a 1-Bottle PCV2/M.hyo Combination Vaccine in with Different Adjuvant formulations This study was designed to evaluate the M.hyo efficacy of a 1-bottle PCV2/M.hyo combination vaccine with different adjuvant formulations. The M.hyo antigen was combined with Porcine Circovirus (Type 1-Type 2 Chimera, or PCV1-2, killed virus) in one bottle.

Processing of Fluids:

Inactivated M.hyo fermentation fluid (described above in Example 1) was treated for each indicated group as follows.

T02-T04: These treatments were the same as those described for treatment groups T02-T04 in Example 7 above.

T05: This was formulated with inactivated M.hyo cells (M.hyo bacterin) as described in Example 1 above under the heading "Fermentation and Inactivation".

All experimental PCV2/M.hyo vaccines were formulated with different adjuvant formulations. The experimental vaccine formulations were prepared with M.hyo antigens processed according to treatments T02-T04. In addition, Treatment T01 corresponded to a placebo (sterile saline). Treatment T05 is a positive control corresponding to an expired RespiSure® vaccine, which is an M.hyo bacterin-based vaccine (Pfizer Animal Health).

These experimental formulations are described in Table 9 below, wherein the symbol * indicates the M hyo antigen from global M hyo seed, Protein A treated supernatant and the symbol ** indicates Investigational Veterinary Product (IVP) serial.

TABLE 9

PCV2/M.hyo Experimental Vaccine Formulations Used for M.hyo Efficacy Study in Different Adjuvant Formulations

| Treatment | IVP Serial ** | PCV1-2 Ag | M Hyo* Ag | Adjuvant | Other |
|---|---|---|---|---|---|
| T01 | 87-244-DK (Placebo) | | NA | | Sterile Saline |
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | A827870 | | Expired "RespiSure" vaccine | | |

Pigs at 3 weeks of age were intramuscularly inoculated with a single dose of the different vaccine formulations described in Table 9 above. Fourteen animals were included in both the placebo and 10% SP-oil groups, thirteen animals were included in the positive control group, and sixteen animals were included in both the 5% Amphigen and 5% Amphigen+5% SLCD groups.

Animals were challenged 21 days after vaccination with a virulent M.hyo field isolate. Animals were necropsied 28 days after challenge and the lungs were removed and scored for consolidation consistent with M.hyo infection. Table 10 below contains the lung lesion scores for the respective treatment groups. Statistical significance was determined by a Mixed Model Analysis of lung scores for each group.

TABLE 10

M.hyo Lung Lesions

| Treatment | # Animal | LS Mean Lung Lesion | Range % Lung Lesion |
|---|---|---|---|
| Placebo (T01) | 14 | 13.1% | 0.1-50.5 |
| 10% SP-oil (T02) | 14 | 4.3% | 0.0-50.8 |
| 5% Amphigen (T03) | 16 | 4.7% | 0.0-38.5 |
| 5% Amph + 5% SLCD (T04) | 16 | 12.0% | 0.1-55.8 |
| Expired RSO (T05) | 13 | 2.28% | 0.0-34.5 |

As indicated in Table 10 above, the placebo group had a mean lung lesion score of 13.1%, as compared to the 10% SP-oil and 5% Amphigen treatment groups which had mean lung scores of 4.3% and 4.7%, respectively. Both the 10% SP-oil and 5% Amphigen formulations reduced and/or prevented lung lesions. Thus, the experimental PCV/M.hyo vaccines formulated with 10% SP-oil or 5% Amphigen were considered efficacious. The PCV2 antigen did not appear to interfere with the M.hyo efficacy of these formulations.

In contrast, the 5% Amphigen+5% SLCD group had a mean lung lesion score of 12.0%. which was an unacceptable result in that it was not different as compared to the placebo. Consequently, the experiment PCV/M.hyo vaccine formulated with 5% Amphigen+5% SLCD was not considered as efficacious.

It is noted that due to the reduced animal number and high variability in lung lesion scoring, no statistical treatment effect could be conclusively demonstrated in this study. For this reason, it was decided that another study would be designed to test the M.hyo efficacy of the PCV/M.hyo experimental formulations in 10% SP-oil. This repeat study is presented in Example 9 below.

Example 9

Evaluation of M.hyo Efficacy of a 1-Bottle PCV2/M.hyo Combination Vaccine in 10% SP-Oil This study is a proof of concept designed to evaluate the M.hyo fraction efficacy of four experimental PCV2/M.hyo vaccines (Serials L0711RK11, L0711RK12, L0711RK13 and L0711RK14 in Table 11 below) prepared by different M.hyo manufacturing processes which utilize Protein A for IgG removal compared to control vaccines prepared with the standard M.hyo manufacturing process. Each of these four experimental PCV2/M.hyo vaccines included 10% SP-oil as the adjuvant.

Processing of Fluids:

T02: Inactivated *M. hyopneumoniae* antigen as described under "Fermentation and Inactivation" in Example 1 above.

T03 and T04: Formulated with inactivated *M. hyopneumoniae* cells as described under "Fermentation and Inactivation" in Example 1 above.

T05: Protein A treatment of medium used to grow *M. hyopneumoniae*. PPLO (porcine heart derived) was made per manufacturer's directions (i.e., 21 g/L) and yeast extract solution was made at 21 g/L in USP. Yeast extract solution was added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. Antibodies in the complete PPLO media were removed by treatment with protein A. Briefly, one liter of rProtein A Sepharose (part number 17-5199-03 GE Healthcare) was packed into a glass column (10×11.5 cm). After removal of storage buffer, the column was treated with 2 column volumes of 1M acetic acid. The resin was equilibrated with 5 column volumes of 50 mM NaPO4, 1M NaCl buffer (pH 7.0). Fifteen liters of complete PPLO medium was loaded onto the resin at a linear flow rate of 140 cm/hour. The column flow through was collected and filter sterilized through a 0.2 micron filter (Sartorius). The treated medium was used propagate *M. hyopneumoniae* cells as described under "Fermentation and Inactivation" above. Whole inactivated culture (including cells) was formulated into the final vaccine.

T06: Inactivated *M. hyopneumoniae* cells were prepared as described under "Fermentation and Inactivation" in Example 1 above. The inactivated fermentation fluid was centrifuged at ~20,000×g (Sorvall RCSB) for 30 min. and the supernatant was sterilized via 0.2 uM filtration. One hundred fifteen mls of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 1.2 liters of the clarified/filtered *M. hyopneumoniae* antigen containing fluids were passed through the resin at a flow rate of 120 cm/hr. The flow through was collected and sterilized via 0.2 µM filter.

T07: Inactivated *M. hyopneumoniae* cells were prepared as described under "Fermentation and Inactivation" in Example 1 above. The inactivated fermentation fluid was clarified by via tangential flow filtration. Briefly, a polyether sulfone filter (GE HealthCare, part number 56-4102-71) with nominal pore size of 0.2 µM was sanitized with 0.5 N sodium hydroxide solution followed by extensive rinsing with sterile USP water. Inactivated *mycoplasma* culture fluid was introduced to the apparatus at a recirculation rate targeted to 14.6 L/minute and a transmembrane pressure of 2-3.4 PSI. Clarification was performed at room temperature. Filter permeate was collected and stored at 2-8C until further processing. One hundred fifteen mls of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 2.3 liters of the clarified/filtered *M. hyopneumoniae* antigen containing fluids were passed through the resin at a flow rate of 120 cm/hr. The flow through was collected and sterilized via 0.2 µM filter.

T08: Inactivated *M. hyopneumoniae* cells were prepared as described under "Fermentation and Inactivation" above. The inactivated fermentation fluid was centrifuged at ~20,000×g (Sorvall RCSB) for 30 min. and the supernatant was sterilized via 0.2 uM filtration. One hundred fifteen mls of rProtein A Sepharose (part number 17-5199-03 GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 1.2 liters of the clarified/filtered *M. hyopneumoniae* antigen containing fluids were passed through the resin at a flow rate of 120 cm/hr. The flow through was collected and sterilized via 0.2 uM filter.

The experimental vaccine formulations were prepared with M.hyo antigens processed according to treatments T02-T08 above. T02, T03 and T04 corresponded to positive controls. In addition, Treatment T01 corresponded to a placebo (sterile saline).

These experimental formulations are described in Table 11 below. The M.hyo antigen corresponds to the M.hyo antigen from global M.hyo seed, Protein A treated supernatant. The information in the "Protein A Treatment" column indicates whether the M.hyo supernatant was treated with Protein A either before or after fermentation.

TABLE 11

PCV2/M. hyo Experimental Vaccine Formulations Used for M. hyo Efficacy Study in SP-Oil Adjuvant

| Treatment | Serial No. | PCV1-2 Ag | M. hyo Ag | Protein A Treatment | Supernatant Clarification Method | Protein A Brand | Adjuvant | Other |
|---|---|---|---|---|---|---|---|---|
| T01 | L0311AS11 | | | | NA | | | Sterile Saline |
| T02 | A828718 | NA | 13 | | Expired RespiSure One | | Amphigen | NA |
| T03 | L0711RK09 | 1.5 RP | 7.5 RP | M. hyo without Protein A treatment and with PCV-2 | | | 10% SP Oil | |
| T04 | L0711RK10 | NA | | M. hyo without Protein A treatment and without PCV-2 | | | | |

TABLE 11-continued

PCV2/M. hyo Experimental Vaccine Formulations Used for M. hyo Efficacy Study in SP-Oil Adjuvant

| Treatment | Serial No. | PCV1-2 Ag | M. hyo Ag | Protein A Treatment | Supernatant Clarification Method | Protein A Brand | Adjuvant | Other |
|---|---|---|---|---|---|---|---|---|
| T05 | L0711RK11 | 1.5 RP | | Before | NA | Sepharose | | |
| T06 | L0711RK12 | | | After | Centrifuge | MAbSelect | | |
| T07 | L0711RK13 | | | After | Filter | MAbSelect | | |
| T08 | L0711RK14 | | | After | Centrifuge | Sepharose | | |

Figures 8A, 8B:
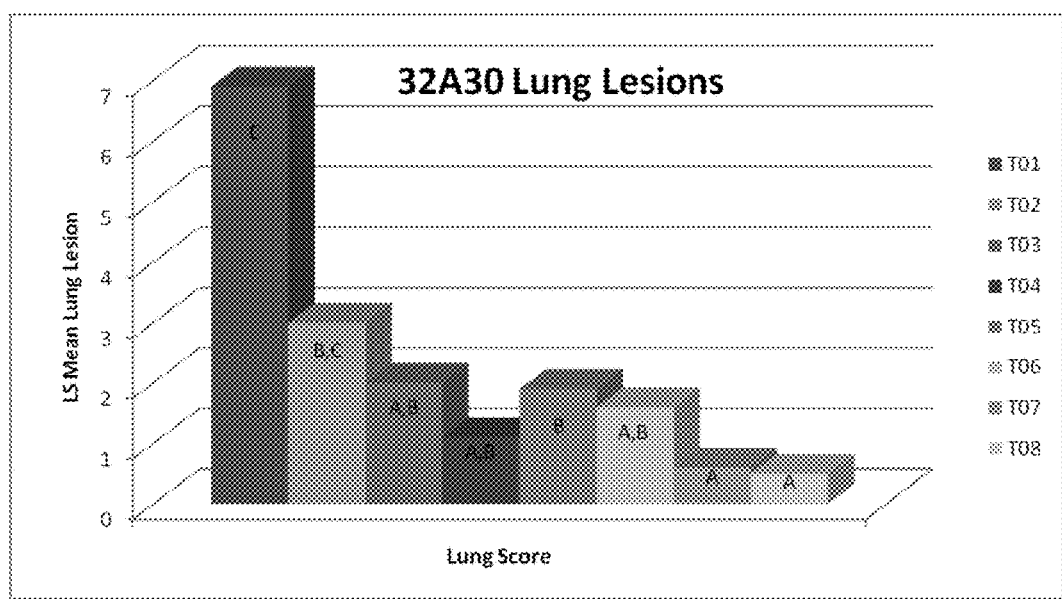
FIGS. 8A and 8B depict the M.hyo efficacy of the PCV2/M.hyo experimental vaccine formulations in SP-oil. The lung scores for formulations employing M.hyo treatments T02-T08 vs. a placebo (T01) are depicted graphically in FIG. 8A. The table in FIG. 8B depicts the contrast of treatments T02-T08 with the placebo.

Pigs at 3 weeks of age were intramuscularly inoculated with a single dose of the different vaccine formulations described in Table 11 above. There were 18 pigs included in each treatment group. Animals were challenged 21 days after vaccination with a virulent M.hyo field isolate. Animals were necropsied 28 days after challenge and the lungs were removed and scored for consolidation consistent with M.hyo infection. FIGS. 8A and 8B show the lung lesion scores for the respective treatment groups. Statistical significance was determined by a Mixed Model Analysis of lung scores for each group.

The lung lesion results depicted in FIGS. 8A and 8B indicate that of all the treatments, only two (T07 and T08) had 100% of pigs in the <5% lung lesion category. It is noted that strong statistical difference were observed in this study.

The results in the present example demonstrate significant M.hyo efficacy in a 1-bottle PCV2/M.hyo experimental formulation employing the Protein A-treated M.hyo supernatant and utilizing SP-oil as the adjuvant. Additionally, Example 7 above demonstrated PCV2 efficacy in a 1-bottle PCV2/M.hyo formulation employing the Protein A-treated M.hyo supernatant and utilizing SP-oil as the adjuvant. Taken together, both M.hyo and PCV2 efficacy have been demonstrated in the 1-bottle PCV2/M.hyo combinations employing Protein A-treated M.hyo supernatant.

Example 10

In Vivo Safety of Experimental PCV2/M.hyo Experimental Vaccines

This study was conducted to evaluate in vivo safety of experimental PCV2-M.hyo vaccines formulated at maximum antigen dose in various adjuvant formulations in the host animal when given at the youngest age (3 weeks of age). Different adjuvant platforms were evaluated in order to determine which of these platforms provided an acceptable safety profile based on temperature, injection site reactions and clinical observations. A 20% SLCD/10% SP-oil formulation was used as a positive ("unsafe") control due to historic issues with injection site reactions observed by this investigative group and others.

Processing of Fluids:

All vaccines were prepared with inactivated *M. hyopneumoniae* antigen as described under "Fermentation and Inactivation" in Example 1. M.hyo whole bulk antigen was used since it was known to contain soluble and insoluble M.hyo antigens, in addition to the immunoglobulins and immunocomplexes that would be removed upon protein A treatment. It is reasonable to conclude that removal of insoluble cell debris and immunuoglobulins and immunocomplexes will only further enhance the safety of the vaccine formulations. The intention of this study was to stringently test the safety of the various adjuvant formulations containing PCV2 antigen and M.hyo antigen. The PCV2 and M.hyo antigens were formulated at maximum release levels to further assess safety. These experimental formulations are described in Table 12 below. IVP indicates Investigational Veterinary Product (IVP).

TABLE 12

PCV2/M.hyo Experimental Vaccine Formulations Used for Safety Study

| IVP Serial | PCV1-2 Ag | M Hyo* Ag | Adjuvant | Other | Minimum Vaccine Vol. (mL) |
|---|---|---|---|---|---|
| 87-244-DK (Placebo) | | NA | | Sterile Saline | NA |
| L0411RK15 | 7.8 RP | 13 RP | 10% SP Oil | NA | 200 |
| L0411RK16 | | | 5% Amphigen | | 200 |
| L0611RK05 | | | 5% Amphigen + 5% SLCD | | 200 |
| L0611RK06 | | | 20% SLCD + 10% SP Oil | | 200 |

*M hyo antigen = from global M hyo seed (whole bulk antigen).

The safety parameters employed in this study were rectal temperature profile and injection site reaction. The results of this study indicated that all candidate adjuvant platforms provided an acceptable safety profile in terms of rectal temperature profile and clinical observations (results not shown). Only the 20% SLCD+10% SP-oil (i.e., positive control) was significantly different than the placebo vaccine and had a number of severe injection site reactions (results not shown).

Example 11

Preparation of Protein A Treated M.hyo Antigen for Pivotal Studies

Figure 9:
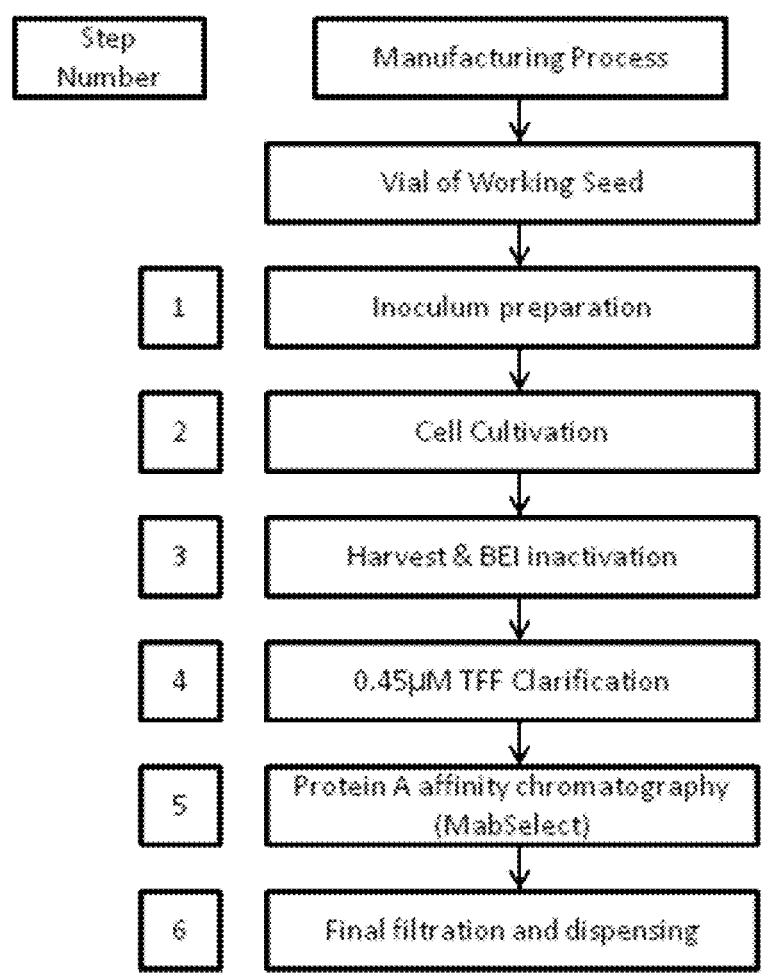
FIG. 9 is a flowchart which shows one embodiment of a manufacturing process used to prepare PCV2-compatible Protein-A treated M.hyo antigen.

FIG. 9 is a flowchart which shows one embodiment of a manufacturing process used to prepare PCV2 compatible Protein-A treated M.hyo antigen. Inactivated whole cultures of M.hyo were clarified of cells via tangential flow filtration. Briefly, a polyether sulfone filter (GE Healthcare, part number 56-4102-49) with nominal pore size of 0.45 µM was sanitized with 0.5 N sodium hydroxide solution followed by extensive rinsing with sterile USP water. Inactivated *mycoplasma* culture fluid was introduced to the apparatus at a recirculation rate targeted to 11.0 L/minute and a transmembrane pressure of ~5 PSI. Clarification was performed at room temperature. Filter permeate was collected and stored at 2-8° C. until further processing.

Following clarification, antigen containing fluids were treated with protein A resin to reduce antibody levels. Briefly, MAbSelect protein A resin (GE Healthcare) was packed into a glass column to a height of 12 cm. The resin was equilibrated with 5 column volumes of 50 mM sodium phosphate, 250 mM NaCl buffer (pH 7.0). Antigen containing fluid, equivalent to 10 column volumes, was loaded onto the resin at a linear flow rate of 100 cm/hour. The column flow through was collected and filter sterilized through a 0.2 micron filter. Regeneration of the column was achieved by flowing 3 column volumes of 25 mM acetate solution at pH 3.7 followed by 4 column volumes of 1M acetic acid solution. Anti-PCV2 antibodies and *M. hyopneumoniae* antigen levels were measured in the final antigen fluid via PCV2 specific antibody ELISA and p46 antigen quantification ELISA, respectively.

T03: Experimental preparation (L1211RK15) of high passage PCVType1-Type2 chimera, killed virus (0.688%-Medium) and M.hyo antigen (9.4%-Medium).

T04: Experimental preparation (L0112RK03) of high passage PCVType1-Type2 chimera, killed virus (0.344%-Low) and M.hyo antigen (4.7%-Low).

T05: Experimental preparation (L1211RK17) of high passage PCVType1-Type2 chimera, killed virus (0.172%-Very Low) and M.hyo antigen (2.32%-Very Low).

TABLE 13

Experimental Design

| | | | | Vaccination | | | |
|---|---|---|---|---|---|---|---|
| Group | N | CP or IVP[1] | Serial/ Lot No. | Antigen Dose (PCV2/M hyo) | Adjuvant | Dose | Route |
| T01 | 24 | Placebo | L1211RK11 | None/High | 10% SP Oil | 2 mL | IM, Right neck |
| T02 | 24 | PCV2-M hyo | L1211RK09 | High/High | | | |
| T03 | 24 | PCV2-M hyo | L1211RK15 | Medium/Medium | | | |
| T04 | 24 | PCV2-M hyo | L0112RK03 | Low/Low | | | |
| T05 | 24 | PCV2-M hyo | L1211RK17 | Very low/ Very low | | | |

[1]IVP = Porcine Circovirus Type 1 - Type 2 Chimera (PCV2), Killed Virus vaccine- *Mycoplasma Hyopneumoniae* (M hyo) Bacterial Extract
CP = *Mycoplasma Hyopneumoniae* bacterial extract adjuvanted with SP-oil 10% (without Porcine Circovirus Type 1 - Type 2 Chimera fraction)
IM = Intramuscularly Example 12

Efficacy of the PCV1-2 Chimeric Fraction Following Intramuscular Administration of a 1-Bottle PCV2/M.hyo Combination Vaccine in 10% SP-Oil The study presented in this example was designed to evaluate the efficacy of the PCV1-2 chimera, killed virus fraction of an experimental 1-Bottle PCV2/M.hyo combination vaccine, administered once to pigs of 21±3 days of age and challenged with a virulent PCV2 isolate at approximately 6 weeks of age.

Four experimental bivalent PCV1-2/M.hyo vaccines at different, but balanced, antigen dose levels and one experimental monovalent M.hyo (negative control) vaccine were formulated with the highest passage antigen. The M.hyo antigen control lot was prepared as described in Example 11 above. The PCV2 antigen was a killed cPCV1-2 antigen prepared as described in Example 2 above. Prior to inactivation of the chimeric virus, the PCV2 antigen lot was concentrated 20× and the concentrates were washed with a balanced salt solution. The final experimental vaccine formulations were adjuvanted using 10% SP oil. These experimental formulations are described below and in Table 13, wherein the antigen dose (% of the PCV2 and M.hyo antigen lots) is provided.

T01: Experimental preparation (L1211RK11) of M.hyo antigen (14.1%-High) without PCVType1-Type2 chimera, killed virus fraction (0%). This corresponds to a negative control (monovalent M.hyo).

T02: Experimental preparation (L1211RK09) of high passage PCVType1-Type2 chimera, killed virus (1.375%-High) and M.hyo antigen (14.1%-High).

On Day 0 (3 weeks of age) a single 2 mL dose of the assigned vaccine was administered by IM injection in the right neck of each pig enrolled in the study. No adverse events were observed post vaccination. A serum sample was collected from all pigs weekly prior to challenge. Any pig detected with PCV2 viremia prior to challenge was removed from the study. On the day prior to challenge fecal swabs and serum samples were collected. The pigs were subsequently challenged with a PCV2a challenge virus. Challenge was conducted around 3 weeks after the vaccination (Day 21). Each pig was inoculated with a total 3 mL of PCV2a challenge virus (Isolate #40895, pre-diluted to 5.10 $\log_{10}$ FAID$_{50}$/mL) with 2 mL intranasally and 1 mL intramuscularly in the left neck. A reserved aliquot of the challenge virus was titrated following the challenge to confirm the actual challenge dose. The undiluted bulk was prediluted 2-fold and the back-titer results achieved a 5.10 $\log_{10}$ FAID$_{50}$/mL challenge level. Prior to necropsy, serum and fecal swabs were collected weekly during the three-week challenge phase. At three weeks post challenge all pigs were euthanized and necropsied. Serum samples and fecal swabs were collected, along with 4 different lymphoid tissues. During necropsy, sections of three lymph nodes (tracheobronchial, mesenteric, inguinal), and tonsil were collected for each pig and individually identified and fixed in 10% buffered formalin solution. The results of testing are provided below.

Vaccine Potency Testing

The L1211RK15 PCV/M.hyo vaccine serial described above was considered to be the reference candidate. Consequently, relative potency for both the M.hyo fraction and the PCV2 fraction were determined versus this candidate reference. These results are presented in Table 14 below. Serial L1211RK11 corresponds to the placebo (no PCV2 fraction).

TABLE 14

Potency Results

Reference L1211RK15

| Serial | M. hyo Potency | PCV Potency |
|---|---|---|
| L1211RK11 | 1.57 | 0.00 |
| L1211RK09 |  | 2.08 |
| L1211RK15 |  | 1.05 |
| L0112RK03 |  | 0.56 |
| L1211RK17 |  | 0.27 |

Results shown for each serial are averages of all replicates tested.

PCV2 Viremia

Following challenge, when compared to the placebo group, all vaccinated groups had a significant reduction in the percent of viremic pigs [$P \leq 0.05$], and throughout the study at least 47% of pigs in the treated groups (T02-T05) stayed negative for PCV2 viremia (Table 15 below). Similarly, all vaccine groups had significantly lower (P=0.0001) PCV2 DNA copy numbers than the placebo group post challenge (data not shown).

TABLE 15 qPCR Qualitative Serum Viremia - Percent Ever Positive and Estimate of Prevented Fraction

| | | Ever Positive? | | | Total | |
|---|---|---|---|---|---|---|
| | | Pos | | Neg | Observations | |
| Trt | Vaccine | # | % | # | % | Number | P-Value |
| T01 | L1211RK11 | 23 | 95.8 | 1 | 4.2 | 24 | |
| T02 | L1211RK09 | 2 | 8.3 | 22 | 91.7 | 24 | <0.0001 |
| T03 | L1211RK15 | 7 | 31.8 | 15 | 68.2 | 22 | 0.0006 |
| T04 | L0112RK03 | 12 | 52.2 | 11 | 47.8 | 23 | 0.0063 |
| T05 | L1211RK17 | 7 | 29.2 | 17 | 70.8 | 24 | 0.0004 |

PCV2 Fecal Shedding

Post-challenge fecal swabs revealed 83.3% of the placebo group pigs (T01) were positive for PCV2 fecal shedding. In contrast, all vaccine groups (T02-T05) had a significant reduction in the percent of pigs shedding PCR detectable PCV2 DNA ($P \leq 0.0061$). These results are presented in Table 16 below. Similarly, all vaccine groups had significantly lower PCV2 DNA copy numbers than the placebo group post challenge (data not shown).

TABLE 16

Fecal Shedding Ever Present after Challenge (Day >21)

| | | Fecal Ever Present? | | | Total | |
|---|---|---|---|---|---|---|
| | | Pos | | Neg | Observations | |
| Trt | Vaccines | # | % | # | % | Number | P-Value |
| T01 | L1211RK11 | 20 | 83.3 | 4 | 16.7 | 24 | |
| T02 | L1211RK09 | 6 | 25.0 | 18 | 75.0 | 24 | 0.0002 |
| T03 | L1211RK15 | 9 | 40.9 | 13 | 59.1 | 22 | 0.0049 |
| T04 | L0112RK03 | 10 | 43.5 | 13 | 56.5 | 23 | 0.0061 |
| T05 | L1211RK17 | 6 | 25.0 | 18 | 75.0 | 24 | 0.0002 |

Serum Antibody Response

All pigs were PCV2 seronegative prior to vaccination. Pigs in the Placebo group remained seronegative prior to challenge. In contrast, pigs in all vaccine groups except for the T05 group showed significant increases ($P \leq 0.0287$) of PCV2 antibody titer on Day 20 post vaccination when compared to placebo, indicating the active immune response to PCV2 following vaccination. PCV2 ELISA antibody titers are summarized in Table 17 below. Pre-challenge titers indicated a significant difference ($P \leq 0.0393$) in the T02 and T03 groups from the T01 group on Days 7-20 and between the T01 and T04 groups on Day 20 ($P \leq 0.0287$). On Days 28 through 42, all vaccine groups had significantly higher titers than T01 ($P \leq 0.0129$; Table 17 below).

TABLE 17

PCV2 ELISA S/P Titers Treatment Comparison by Study Day

| Contrast | Day −1 | Day 07 | Day 14 | Day 20 | Day 28 |
|---|---|---|---|---|---|
| T01 vs T02 | ns | 0.0229 | 0.0005 | 0.0001 | <0.0001 |
| T01 vs T03 | ns | 0.0302 | 0.0393 | 0.0060 | <0.0001 |
| T01 vs T04 | ns | ns | ns | 0.0287 | <0.0001 |
| T01 vs T05 | ns | ns | ns | ns | <0.0001 |

| Contrast | Day 35 | Day 42 |
|---|---|---|
| T01 vs T02 | <0.0001 | 0.0056 |
| T01 vs T03 | <0.0001 | 0.0024 |
| T01 vs T04 | <0.0001 | 0.0114 |
| T01 vs T05 | <0.0001 | 0.0129 |

*When contrast is significant ($\leq 0.05$) a P-value is reported, P-values >0.05 are designated as ns (not significant)

Lymphoid Lesions and Colonization

At the time of necropsy, when compared to the placebo group, all vaccinated groups had a significant reduction in total amount of PCV2 antigen detected in tissues. The data concerning PCV2 infection in Lymphoid Tissues (IHC scores) are summarized in Table 18 below. As shown in Table 18, all vaccine groups had significantly lower IHC scores than the T01 placebo group.

TABLE 18

PCV2 IHC Scores: If lymphoid or tonsil tissues ever abnormal

| Treatment | LSM | Compared to L12111RK11 P-value |
|---|---|---|
| L1211RK11 | 0.75 | |
| L1211RK09 | 0.15 | 0.0003 |
| L1211RK15 | 0.30 | 0.0055 |
| L0112RK03 | 0.34 | 0.0106 |
| L1211RK17 | 0.41 | 0.0273 |

* Animal was considered abnormal if score was >0 in any lymphoid tissue or tonsil sample.

All vaccinated groups also saw a significant reduction in PCV2 Lymphoid Depletion as shown in Table 19 below.

TABLE 19

PCV2 Lymphoid Depletion: If lymphoid or tonsil tissues ever abnormal

| Treatment | LSM | Compared to L12111RK11 P-value |
|---|---|---|
| L1211RK11 | 0.48 | |
| L1211RK09 | 0.04 | 0.0053 |
| L1211RK15 | 0.13 | 0.0181 |
| L0112RK03 | 0.08 | 0.0069 |
| L1211RK17 | 0.11 | 0.0116 |

* Animal was considered abnormal if score was >0 in any lymphoid tissue or tonsil sample.

Additionally, all vaccinated groups saw a significant reduction in Histiocytic Replacement as shown in Table 20 below.

TABLE 20

PCV2 Histiocytic
Replacement: if lymphoid or tonsil tissues ever abnormal

| Treatment | LSM** | Compared to L12111RK11 P-value |
|---|---|---|
| L1211RK11 | ND | |
| L1211RK09 | ND | 0.0006 |
| L1211RK15 | ND | 0.0098 |
| L0112RK03 | ND | 0.0098 |
| L1211RK17 | ND | 0.0173 |

* Animal was considered abnormal if score was >0 in any lymphoid tissue or tonsil sample.
** Fisher exact test was used due to non-convergence, therefore least square means were not determined (ND).

The data presented in this Example indicates that the vaccine groups:

Significantly protected and aided in the prevention of PCV2 viremia post-challenge;

Significantly aided in the prevention of fecal shedding of PCV2 post-challenge in all vaccinated animals;

Elicited a statistically significant serological response 28 days post vaccination in groups T02-T05. In addition, T02 and T03 demonstrated a statistically significant response as early as 7 days post-vaccination when compared to T01;

Significantly reduced microscopic lesions (Lymphoid Depletion and Histiocytic replacement) in all vaccinated animals; and All vaccines proved to be efficacious and vaccine serial L1211RK15 was selected as a reference candidate.

Example 13

Efficacy of the M.hyo Fraction Following Intramuscular Administration of a 1-Bottle PCV2/M.hyo Combination Vaccine in 10% SP-Oil The objective of the study presented in this example was to evaluate efficacy of the *Mycoplasma hyopneumoniae* (*M. hyopneumoniae*) fraction of an experimental Porcine Circovirus (PCV) Type 1-Type 2 Chimera, Killed Virus-*Mycoplasma Hyopneumoniae* (M hyo) Bacterial Extract, administered intramuscularly once to pigs of 21±3 days of age and challenged with a virulent lung homogenate of *M. hyopneumoniae* at 7 weeks after vaccination.

Four experimental bivalent PCV1-2/M.hyo vaccines at different, but balanced, antigen dose levels and one experimental monovalent PCV2 (negative control) vaccine were formulated. The M.hyo antigen control lot was prepared as described in Example 11 above. The PCV2 antigen was a killed cPCV1-2 antigen prepared as described in Example 2 above. Prior to inactivation of the chimeric virus, the PCV2 antigen lot was concentrated 20× and the concentrates were washed with a balanced salt solution. The final experimental vaccine formulations were adjuvanted using 10% SP oil. These experimental formulations are described below and in Table 21 below, wherein the antigen dose (% of the PCV2 and M.hyo antigen lots) is provided.

T01: Experimental preparation (L1211RK10) of high passage PCVType1-Type2 chimera, killed virus (1.375%-High) without M.hyo fraction (0%). This corresponds to a negative control (monovalent PCV2).

T02: Experimental preparation (L1211RK09) of high passage PCVType1-Type2 chimera, killed virus (1.375%-High) and M.hyo antigen (14.1%-High).

T03: Experimental preparation (L1211RK15) of high passage PCVType1-Type2 chimera, killed virus (0.688%-Medium) and M.hyo antigen (9.4%-Medium).

TABLE 21

Experimental Design

| Group | N | CP or IVP[1] | Serial/Lot No. | Antigen dose RP (PCV2/M hyo) | Adjuvant | Dose | Route |
|---|---|---|---|---|---|---|---|
| NTX | 9 | Sentinel | NA | | No Vaccination | | |
| T01 | 38 | Placebo - PCV2 | L1211RK10 | High/None | 10% SP Oil | 2 mL | IM, Left neck |
| T02 | 38 | PCV2-M hyo | L1211RK09 | High/High | | | |
| T03 | 38 | PCV2-M hyo | L1211RK15 | Medium/Medium | | | |

[1]IVP = Investigational Veterinary Product = Porcine Circovirus Type 1 - Type 2 Chimera (PCV2), Killed Virus vaccine- *Mycoplasma Hyopneumoniae* (M hyo) Bacterial Extract
CP = Control Product = Killed Chimeric PCV1-2 fraction adjuvanted with SP-oil 10% adjuvanted (without *M. hyopneumoniae* fraction)
IM = Intramuscularly On Day 0, 123 clinically healthy, susceptible pigs were enrolled in this study at three weeks of age. Pigs were blocked by litter and randomly assigned to a sentinel (NTX) group or one of the three treatment groups (T01-T03); administered intramuscularly 2 mL of either an experimental PCV1-2/*M. hyopneumoniae* vaccine at the minimum immunizing dose (MID), an experimental PCV1-2/*M. hyopneumoniae* vaccine at a dose slightly higher than MID or a placebo containing PCV1-2 only at MID. Seven weeks after vaccination the sentinel pigs were euthanized and necropsied to confirm absence of *M. hyopneumoniae* and all treated pigs were challenged twice (on two successive days) with a live, virulent *M. hyopneumoniae* lung homogenate. All remaining pigs were euthanized and necropsied four weeks after challenge. At necropsy lungs were scored for lesions typical of *M. hyopneumoniae*. Post-challenge lung lesions are the primary outcome variable. Vaccination is considered effective if the lower 95% confidence interval of the mitigated fraction is >0.

Vaccine Potency Testing

The L1211RK15 PCV/M.hyo vaccine serial described above was considered to be the reference candidate. Consequently, relative potency for both the M.hyo fraction and the PCV2 fraction used in this M.hyo efficacy study were determined versus this candidate reference. These results are presented in Table 22 below. Serial L1211RK10 corresponds to the placebo (no M.hyo fraction).

TABLE 22

Potency Results

| | Reference L1211RK15 | |
|---|---|---|
| Serial | M. hyo[1] Potency | PCV Potency[2] |
| L1211RK10 | 0.00 | 2.33 |
| L1211RK09 | 1.48 | 2.20 |
| L1211RK15 | 1.00 | 1.07 |

Results shown for each serial are averages of all replicates tested.
[1]*M. hyopneumoniae* potency tested in five replicates.
[2]PCV potency tested in one replicate (L1211RK10), or five (L1211RK09, L1211RK15) replicates.

Serology

M.hyo antibody titers indicated that all pigs were serologically *M. hyopneumoniae* negative on Day 0 and remained negative prior to challenge. At all time points post vaccination (Days 21, 47 and 75) T02 and T03 had significantly higher ($P \leq 0.0004$) geometric least squares mean *M. hyopneumoniae* antibody titers compared to T01 (serology data not shown).

Percentage of Total Lung with Lesions

Frequency distributions of lung lesion scores for each lung lobe were calculated by treatment. Percentage of total lung with lesions was calculated using the following formula: Percentage of total lung with lesions={(0.10×left cranial)+(0.10×left middle)+(0.25×left caudal)+(0.10×right cranial)+(0.10×right middle)+(0.25×right caudal)+(0.10× accessory)}. The arcsine square root transformation was applied to the percentage of total lung with lesions prior to analysis. Percentage of Total Lung with Lesions was analyzed using a mixed linear model. Pair-wise comparisons were made between treatment groups if the treatment effect was significant. Back transformed least squares means of percentage of total lung with lesions, and their 95% confidence intervals were calculated as well as the minimums and maximums. Lung lesions were summarized with the stratified mitigated fraction and 95% confidence limits. The lung lesion results are presented in Table 23 below.

TABLE 23

Analysis of Percent of Total Lung with Lesion
Summary of Least Squares Means

| Group | Serial | N | % Lung with Lesion[1] | Range | | |
|---|---|---|---|---|---|---|
| NTX | | 9 | 0.1 | 0.0 to 0.8 | Mitigated Fraction | |

| Group | Serial | N | % Lung with Lesion[1] | Range | Contrast vs T01 | 95% CI[4] |
|---|---|---|---|---|---|---|
| T01 | L1211RK10 | 36 | 6.1[b] | 0.0 to 32.3 | | |
| T02 | L1211RK09 | 36 | 2.7[a] | 0.0 to 23.5 | 40.9 | 13.3 to 61.8 |
| T03 | L1211RK15 | 38 | 2.6[a] | 0.0 to 49.0 | 46.9 | 18.2 to 68.3 |

[1]Back Transformed Least Squares Mean
[4]Confidence Interval
Treatment groups with the same letter are not significantly different at P-value 0.05.

A few low percentage lung lesions were observed in the NTX pig lungs which were attributed to a known incidence of *Bordetella* in this herd. Bacterial culture on lung tissue swabs confirmed several pigs were *B. bronchiseptica* culture positive and *M. hyopneumoniae* culture confirmed all NTX pigs were *M. hyopneumoniae* culture negative prior to challenge administration.

The protocol met the validity criteria in that the LS mean lung lesions for T01 were >4%. The LS Mean lung lesions for T02 and T03 were significantly ($P \leq 0.05$) lower than T01 and both met the mitigated fraction criteria that the lower 95% confidence interval was >0. The validity requirements of this study were met in that there was no evidence of pre-challenge exposure to *M. hyopneumoniae*. The challenge was valid in that the back-transformed mean lung lesion scores in placebo pigs (T01) was >4%.

Compared to the negative control group (T01), treatment groups T02 and T03 demonstrated a significant reduction ($P \leq 0.05$) in percent lung with lesion compared to T01. The mitigated fractions for T02 and T03 compared to T01 met the protocol criteria for efficacy.

Under the conditions of this study, both vaccines (T02 & T03) helped to mitigate lung lesions, the primary variable for efficacy. The results in the present example demonstrate significant M.hyo efficacy in a 1-bottle PCV2/M.hyo experimental formulation.

Example 14

Evaluation of Virucidal Activity Against PRRS Virus

The studies presented in this example were designed to evaluate the various adjuvant platforms for virucidal activity against PRRS virus. Initial experiments focused on adjuvant alone (i.e., the formulations did not contain PCV or M.hyo antigens). The adjuvant evaluation for PRRS virucidal activity is presented in FIG. 10. Preliminary virucidal assessment indicated that 10% SP-oil, 0.2% Carbopol and 2.5% Amphigen are non-virucidal to PRRS virus. In contrast, the 20% SLCD adjuvant appeared to be virucidal to PRRS virus.

Further studies were performed to evaluate whether the PCV/M.hyo formulations adjuvanted with the different adjuvant platforms were non-virucidal to PRRS virus. These results are presented in Table 24 below, wherein the symbol * indicates those vaccine serials which were virucidal to PRRS virus.

TABLE 24

Results of PRRS Virucidal Assay with Different Formulations

| Study | Vaccine Serial Used in Studies of Examples 7, 8, 10 Description | Serial # | Potency p46 RP (ru/ds) | PCV2 NVSL RP | PRRS Virucidal A | PRRS Virucidal B |
|---|---|---|---|---|---|---|
| Examples 7, 8, 10 | Sterile Saline (0.9% Sodium chloride) | 87-244-DK (Placebo) | | | | |
| Examples 7, 8 | cPCV (RP 1.6) + M Hyo Prot A treated (RP 7.5) in 10% SP Oil | L0411RK08 | 7.1 | 1.29 | −0.10 | −0.13 |
| Examples 7, 8 | cPCV (RP 1.6) + M Hyo Prot A treated (RP 7.5) in 5% Amphigen | L0411RK09 | 7.3 | 1.33 | −0.10 | +0.14 |
| Examples 7, 8 | cPCV (RP 1.6) + M Hyo Prot A treated (RP 7.5) in 5% Amph + 5% SLCD | L0611RK03 | 6.9 | 1.15 | −0.36 | −0.33 |
| Example 7 | cPCV (RP 1.6) monovalent in 20% SLCD | L0611RK04 | | 1.50 | −1.86* | −0.50 |
| Example 8 | Expired RespiSure One serial | A827870 | 12.6 | | | |
| Example 10 | cPCV (RP 7.8) + M Hyo Whole Bulk (RP 13.3) in 10% SP Oil | L0411RK15 | 14 | 1.03 | −0.32 | −0.03 |
| Example 10 | cPCV (RP 7.8) + M Hyo Whole Bulk (RP 13.3) in 5% Amphigen | L0411RK16 | 15.5 | 1.12 | −0.36 | −0.53 |
| Example 10 | cPCV (RP 7.8) + M Hyo Whole Bulk (RP 13.3) in 5% Amph + 5% SLCD | L0611RK05 | 17.5 | 1.50 | -0.54 | −0.33 |
| Example 10 | cPCV (RP 7.8) + M Hyo Whole Bulk (RP 13.3) in 20% SLCD + 10% SP Oil | L0611RK06 | 15.9 | 1.13 | −1.93* | −0.99* |

*Indicates Virucidal (>0.7 log loss)
A—Virucidal assay control GMT ~5.53 log/mL
B—Virucidal assay control GMT ~6.42 log/mL The results presented in Table 24 above indicate that 10% SP-oil is non-virucidal to PRRS virus. Further PCV/M.hyo vaccine serials were prepared using 10% SP-oil as the adjuvant (Table 25). The antigenic potency of these vaccine serials was compared to a Reference PCV/M.hyo vaccine serial (L1211RK15) described above. The results shown in Table 25 below further indicate that 10% SP-oil is non-virucidal to PRRS virus. The test sample values in Table 25 were each higher (+sign) than the virucidal assay control, which had a geometric mean titer (GMT) of about 5.9±0.5 log/ml.

TABLE 25

Results of Virucidal Assay with Different PCV/M.hyo Formulations Adjuvanted with 10% SP-oil

| Vaccine Serial Used Description | Serial # | Potency p46 RP (ru/ds) Reference L1211RK15 | PCV2 NVSL Reference L1211RK15 | PRRS Virucidal log10 TCID50/mL |
|---|---|---|---|---|
| Sterile Diluent (sterile water) | 1949122 | na | na | |
| cPCV + M Hyo Prot A treated in 10% SP Oil | L0912RK12 | 1.62 | 2.60 | +0.58 |
| cPCV + M Hyo Prot A treated in 10% SP Oil | L0912RK10 | 0.88 | 1.23 | +0.58 |
| cPCV + M Hyo Prot A treated in 10% SP Oil | L0912RK11 | 1.24 | 2.62 | +0.58 |
| cPCV + M Hyo Prot A treated in 10% SP Oil | L0912RK08 | 1.08 | 1.03 | +0.91 |
| cPCV + M Hyo Prot A treated in 10% SP Oil | L0912RK09 | 1.65 | 2.06 | +0.50 |

Virucidal Assay control GMT~5.9 ± 0.5 log/ml

The results presented in this example demonstrate that 10% SP-oil is non-virucidal to PRRS virus. The results presented in this example further demonstrate that the PCV/M.hyo formulation adjuvanted with 10% SP-oil was among those vaccine serials which were considered non-virucidal to PRRS virus (Table 24 and Table 25). In conclusion, the PCV/M.hyo formulation adjuvanted with 10% SP-oil was considered an effective platform on which to base a trivalent combination including PCV, M.hyo, and PRRS virus.

Example 15

Preparation of a PCV/M.hyo/PRRS Combination Vaccine

A PCV/M.hyo formulation adjuvanted with an adjuvant platform which is non-virucidal to PRRS virus (see Tables 24 and 25 above), is provided as a ready-to-use in one-bottle liquid composition. This 1-bottle PCV/M.hyo formulation employs Protein A-treated M.hyo supernatant. Both M.hyo and PCV2 efficacy have been demonstrated in such PCV2/M.hyo formulations employing M.hyo Protein A-treated supernatant (see Examples 7-9). In the present example, this divalent PCV2/M.hyo formulation is combined with a monovalent PRRS virus antigen.

In one embodiment, a PCV/M.hyo combination in 10% SP-oil and corresponding to one of the vaccine serials L0711RK11, L0711RK12, L0711RK13 and L0711RK14 in Table 11 above or L1211RK09, L1211RK15, L0112RK03 and L1211RK17 in Table 13 above is provided as a ready-to-use in one bottle liquid composition. The results presented in Example 14 above demonstrated that 10% SP-oil is non-virucidal to PRRS virus. Example 14 also demonstrated that PCV2/M.hyo formulations adjuvanted with 10% SP-oil were among those vaccine serials which were considered non-virucidal to PRRS virus. In the present example, such a 1-bottle PCV2/M.hyo liquid composition is used to re-hydrate a lyophilized genetically modified live PRRS virus composition contained in a second bottle, such that all antigens are contained in a single bottle prior to being administered to a pig of a suitable age (e.g., at 3 weeks of age or older).

In one embodiment, the PRRS virus has the genomic sequence corresponding to SEQ ID NO: 16 or a variant thereof. In another embodiment, the PRRS virus employed in the trivalent composition is the PRRS virus isolate designated ISU-55, which was deposited in the ATCC under the accession number VR 2430. Suitable amounts of the respective antigens are described herein. Desirably, all antigens are administered in a single dose to the pig.

What is claimed is:

1. A multivalent immunogenic composition comprising a soluble portion of a *Mycoplasma hyopneumoniae* (M.hyo) whole cell preparation; a porcine circovirus type 2 (PCV2) antigen; and a *Lawsonia intracellularis* antigen, wherein the soluble portion of the M.hyo preparation comprises M.hyo-specific soluble protein antigens and is separated from insoluble cellular material and substantially free of both (i) IgG and (ii) immunocomplexes comprised of antigen bound to immunoglobulin.

2. The composition of claim 1, wherein the soluble portion of the M.hyo preparation has been treated with protein-A or protein-G prior to being added to the immunogenic composition.

3. The composition of claim 1, wherein the composition elicits a protective immune response in a pig against M.hyo, PCV2 and *Lawsonia intracellularis*.

4. The composition of claim 1, wherein the PCV2 antigen is in the form of a chimeric type-1-type 2 circovirus, said chimeric virus comprising an inactivated recombinant porcine circovirus type 1 expressing the porcine circovirus type 2 ORF2 protein.

5. The composition of claim 1, wherein the PCV2 antigen is in the form of a recombinant ORF2 protein.

6. The composition of claim 5, wherein the recombinant ORF2 protein is expressed from a baculovirus vector.

7. The composition of claim 1, further comprising at least one additional antigen that is protective against a microorganism that can cause disease in pigs.

8. The composition of claim 7, wherein the microorganism comprises bacteria, viruses, or protozoans.

9. The composition of claim 8, wherein the microorganism is selected from the group consisting of porcine reproductive and respiratory syndrome virus (PRRSV), porcine parvovirus (PPV), *Haemophilus parasuis*, *Pasteurella multocida*, *Streptococcum suis*, *Staphylococcus hyicus*, *Actinobacilllus pleuropneumoniae*, *Bordetella bronchiseptica*, *Salmonella choleraesuis*, *Salmonella enteritidis*, *Erysipelothrix rhusiopathiae*, *Mycoplasma hyorhinis*, *Mycoplasma hyosynoviae*, *leptospira* bacteria, swine influenza virus (SIV), *Escherichia coli* antigen, *Brachyspira hyodysenteriae*, porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) virus, a pathogen causative of Swine Transmissable Gastroenteritis, and combinations thereof.

10. The composition of claim 1, wherein the composition further comprises an adjuvant.

11. The composition of claim 10, wherein the adjuvant is selected from the group consisting of an oil-in-water adjuvant, a polymer and water adjuvant, a water-in-oil adjuvant, an aluminum hydroxide adjuvant, a vitamin E adjuvant and combinations thereof.

12. The composition of claim 1, wherein the composition further comprises a pharmaceutically acceptable carrier.

13. The composition of claim 1, wherein the composition elicits a protective immune response against M.hyo, PCV2, and *Lawsonia intracellularis* when administered as a single dose administration.

14. A method of immunizing a pig against *Mycoplasma hyopneumoniae* (M.hyo), PCV2, and *Lawsonia intracellularis* which comprises administering to the pig the composition of claim 1.

15. The method of claim 14, wherein said composition is administered intramuscularly, intradermally, transdermally, or subcutaneously.

16. The method of claim 14, wherein said composition is administered in a single dose or in multiple doses.

17. The method of claim 14, wherein the composition is administered in conjunction with at least one additional antigen that is protective against a microorganism that is known to infect pigs.

18. The method of claim 17, wherein said microorganism is selected from the group consisting of porcine reproductive and respiratory syndrome virus (PRRSV), porcine parvovirus (PPV), *Haemophilus parasuis*, *Pasteurella multocida*, *Streptococcum suis*, *Staphylococcus hyicus*, *Actinobacilllus pleuropneumoniae*, *Bordetella bronchiseptica*, *Salmonella choleraesuis*, *Salmonella enteritidis*, *Erysipelothrix rhusiopathiae*, *Mycoplasma hyorhinis*, *Mycoplasma hyosynoviae*, *leptospira* bacteria, swine influenza virus (SIV), *Escherichia coli* antigen, *Brachyspira hyodysenteriae*, porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) virus, a pathogen causative of Swine Transmissable Gastroenteritis, and combinations thereof.

19. The method of claim 14, wherein the composition is administered to pigs having maternally derived antibodies against at least one of M.hyo and PCV2.

20. The method of claim 14, wherein the composition is administered to pigs at 3 weeks of age or older.

21. A kit comprising: a bottle comprising an immunogenic composition including the soluble portion of a *Mycoplasma hyopneumoniae* (M.hyo) whole cell preparation, a PCV2 antigen, and a *Lawsonia intracellularis* antigen, wherein the soluble portion of the M.hyo preparation comprises M.hyo-specific soluble protein antigens and is separated from insoluble cellular material and substantially free of both (i) IgG and (ii) antigen/immunoglobulin immunocomplexes.

22. A method for preparing an immunogenic composition, the method comprising:
  i) culturing M.hyo in a suitable media over periods ranging from 18-144 hours;
  ii) subsequently inactivating the M.hyo culture;
  iii) harvesting the inactivated culture fluid, wherein the inactivated culture fluid comprises an M.hyo whole cell preparation comprising both a soluble liquid fraction and insoluble cellular material;
  iv) separating the soluble liquid fraction from the insoluble cellular material;
  v) substantially removing both IgG and antigen/immunoglobulin immunocomplexes from the separated soluble liquid fraction to form a soluble portion of the M.hyo whole cell preparation; and
  vi) subsequently combining the soluble portion of the M.hyo whole cell preparation with a PCV2 antigen and a *Lawsonia intracellularis* antigen.

* * * * *